United States Patent
Hong et al.

(10) Patent No.: US 6,849,733 B1
(45) Date of Patent: Feb. 1, 2005

(54) NEUROPEPTIDE-Y LIGANDS

(75) Inventors: Yufeng Hong, San Diego, CA (US); Vlad Edward Gregor, Del Mar, CA (US); Anthony Lai Ling, San Diego, CA (US); Eileen Valenzuela Tompkins, San Diego, CA (US)

(73) Assignee: Agouron Pharmaceuticals, Inc., San Diego, CA (US)

(*) Notice: Subject to any disclaimer, the term of this patent is extended or adjusted under 35 U.S.C. 154(b) by 0 days.

(21) Appl. No.: 08/916,527

(22) Filed: Aug. 22, 1997

Related U.S. Application Data

(60) Provisional application No. 60/025,791, filed on Aug. 23, 1996.

(51) Int. Cl.⁷ .............. C07D 413/00; C07D 211/72; C07D 205/00; C07D 319/12; C07C 279/00

(52) U.S. Cl. .............. 544/111; 544/145; 544/147; 544/162; 544/164; 544/165; 544/224; 546/304; 546/304.4; 546/307.4; 546/557; 546/953; 549/59; 549/63; 549/69; 549/378; 549/379; 549/380; 549/424; 549/475; 549/476; 549/480; 549/546; 564/64; 564/225; 564/237; 564/238

(58) Field of Search .............. 564/64, 725, 237, 564/238, 225; 549/59, 63, 69, 378, 379, 380, 424, 475, 476, 480, 546; 546/304, 304.4, 307.4, 557, 953; 544/111, 145, 147, 162, 164, 165, 224

(56) References Cited

U.S. PATENT DOCUMENTS

| | | | | |
|---|---|---|---|---|
| 4,486,439 A | * | 12/1984 | Studt et al. | 424/263 |
| 4,562,209 A | * | 12/1985 | Chou | 424/18 |
| 5,380,945 A | * | 1/1995 | Murad et al. | 564/108 |
| 5,482,947 A | | 1/1996 | Talley et al. | 514/311 |
| 5,504,094 A | | 4/1996 | Bruns, Jr. et al. | 514/324 |
| 5,506,258 A | | 4/1996 | Christophe et al. | 514/423 |
| 5,583,238 A | | 12/1996 | Ng et al. | |

FOREIGN PATENT DOCUMENTS

| | | |
|---|---|---|
| WO | WO 96/12489 | 5/1996 |
| WO | WO 96/14307 | 5/1996 |

OTHER PUBLICATIONS

El–Kerdawy et al, Pharmazie (1975), 30(12), 768–70, CA abstract vol. 84, No. 74194, 1975.*

Csuros et al, Acta Chimica Academiae Scientiarum Hungaricae (1973), 78(4), 409–17, CA abstract vol. 80, No. 3471, 1973.*

Chemical Abstract vol. 84 No. 74194, El–Kerdawy et al, "Synthesis of morpholinobiguanide derivatives" 1975.*

* cited by examiner

*Primary Examiner*—Rita Desai
*Assistant Examiner*—Raymond Covington
(74) *Attorney, Agent, or Firm*—Peter C. Richardson; Bryan C. Zielinski; Wendy L. Hsu

(57) ABSTRACT

There are disclosed novel neuropeptide Y ligands having the general formula I

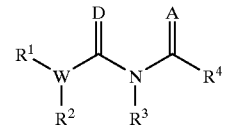

Figure 1D:
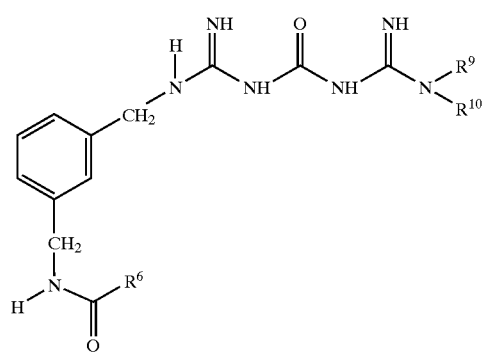
Figure 1E:
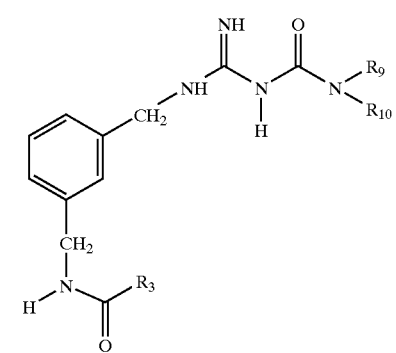
Figure 1E:
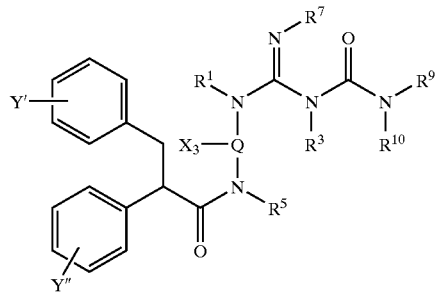
Figure 1E:
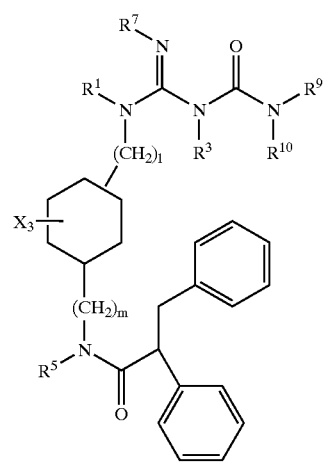
Figure 1E:
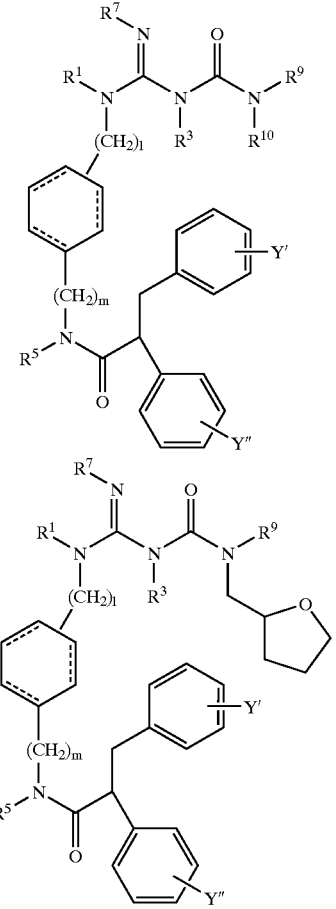
Figure 1E:
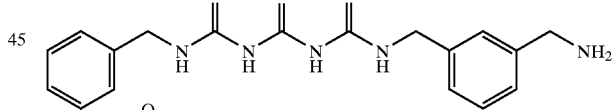
Figure 1E:
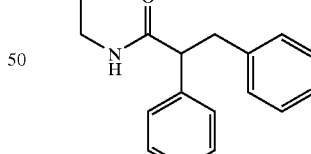
Figure 1E:
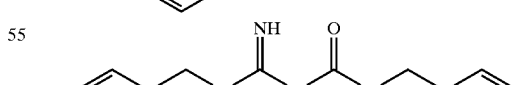
Figure 1E:
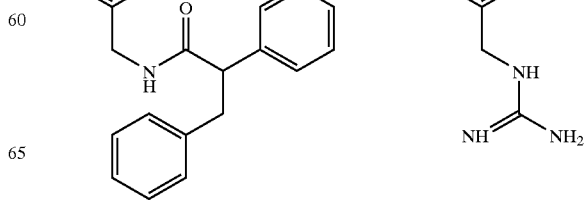

Wherein the symbols W, A, D, $R^1$, $R^2$, $R^3$, $R^4$ are further defined in the description. Compounds of formula I are agonists and antagonists of neuropeptide Y, and are therefore useful as regulators.

14 Claims, No Drawings

NEUROPEPTIDE-Y LIGANDS

This application claims the benefit under Title 35, United States Codes § 119 (e) of U.S. provisional Application No. 60/025,791, filed Aug. 23, 1996.

The invention relates to compounds that modulate the activity of neuroendocrine hormones. It relates particularly to neuroendocrine receptor ligands and methods for their use.

BACKGROUND OF THE INVENTION

Cells of the neuroendocrine system secrete neuropeptide hormones that modulate a diverse array of physiological activities. In addition to neurotransmission, neuropeptides regulate secretory functions of adenohypophysial and pancreatic cells as well as cells of the adrenal cortex and the digestive system. The hormone termed neuropeptide Y is co-released with norepinephrine from postganglionic neurons and participates along with that hormone in regulating vascular smooth muscle tone and maintaining blood pressure. Agonists and antagonists of neuropeptide-Y are therefor useful in treating clinical disorders relating to both hypotension and hypertension.

Receptor binding ligands are typically polypeptides, for example, neuropeptide-Y, a 36 amino acid polypeptide sequence whose composition is known. Receptor activity can be inhibited by competitive binding of an antagonist of the neuropeptide to the Y-receptor. Several synthetic antagonist species of neuropeptide-Y have been developed. Among these are corresponding amino acid sequences wherein some of the native L-amino acids are replaced by corresponding D-amino acids (U.S. Pat. No. 5,328,899).

Neurons bind neuropeptide-Y through several distinct Y-receptors; receptors Y1, Y2, Y3, Y4, Y5 are known. The neuroendocrine Y1 receptor is one of those believed to be particularly associated with appetite, and synthetic neuropeptide ligands that selectively bind to the Y1 receptor and have antagonistic activity to neuropeptide-Y are believed to be anorectic agents useful in treating obesity.

Other non-peptide neuropeptide-Y antagonist species have been developed for pharmacologic use. Among these are benzylamine derivatives of molecular systems comprising phenyl, thienyl, pyridyl or pyrimidine groups (Peterson, J M et al. WO9614307); sulfanilyl derivatives of quinoline (Downing, D M et al. 211th Amer. Chem. Soc. Meeting, March 1996); phenylsulfonyl derivatives of aniline-based compounds (Wright, J L et al., 211 Amer. Chem. Soc. Meeting, March, 1996); raloxiphene, and a benzothiophene derivative of pyrrolidine or piperidino groups having antiestrogen properties (U.S. Pat. No. 5,504,094 to Bruns et al.). Also described are sulfamyl derivatives of phenylalanine-amidine-containing compounds (U.S. Pat. No. 5,506,258 to Christophe et al.); and bicyclic neuropeptide-Y receptor antagonists comprising substituted benzofurans, benzothiophenes, or indoles (WO96/12489 to Eli Lilly).

SUMMARY OF THE INVENTION

The present invention relates to novel compounds represented by the general formula

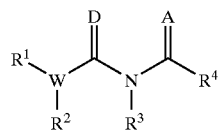

And all pharmaceutically acceptable salts thereof.
The compounds of the invention have a general core amidino-urea or diaminourea structure:

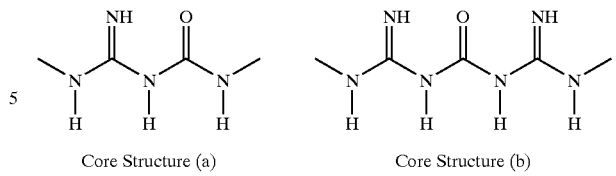

Core Structure (a)         Core Structure (b)

Wherein A is O, S or N—R, wherein R is lower alkyl $(C_1\text{-}C_8)$;

D is O, S or N—$R^7$:

W is N, CH or C—$R^8$; or W is absent;

$R_1$ and $R_3$ are substituted or unsubstituted alkyl groups;

$R_2$ is

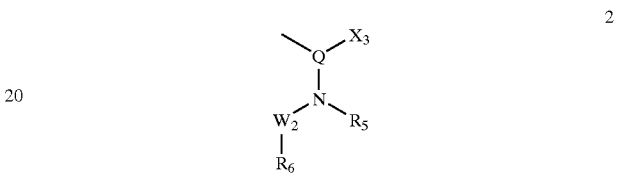

wherein Q is either a $(-CH_2-)_z$ group where z is 1 to 12; a carbocyclic or heterocyclic ring of the formula $(-CH_2-)_x$; or a carbocyclic or heterocyclic aromatic ring. The Q moiety can be substituted as set forth in the description of the invention;

$X^3$ is a substituent on Q which can be H, lower alkyl, lower alkoxy, aryl, hydroxy, trifluoromethyl, or other common ring substituents. $R^5$ and $R^6$ are substituted or unsubstituted alkyl, aryl or heteroaryl groups. $R^4$ has either of the structures

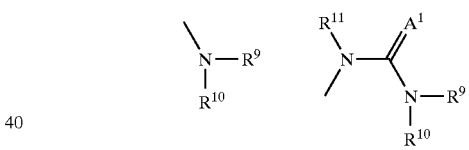

wherein $R^9$ is defined as for $R^5$ and $R^6$; and $R^{10}$ is a substituted or unsubstituted linear, branched alkyl group or a substituted or unsubstituted aryl group. The substituents for Q, $X^3$, $R^5$, $R^6$, $R^9$ and $R^{10}$, $R^2$ and $R^4$ are fully set forth in the description below.

Another aspect of the invention are pharmaceutical formulations containing the novel compounds of the invention.

Another aspect of the invention is a method of treatment for disorders related to abnormal neuropeptide Y activity.

DETAILED DESCRIPTION OF THE PREFERRED EMBODIMENT

The term "alkyl" used herein refers to a monovalent straight or branched chain radical of from one to ten carbon atoms, including, but not limited to, methyl, ethyl, n-propyl, isopropyl, n-butyl, isobutyl, tert-butyl, n-hexyl, and the like. The term "aryl" when used alone, denotes a homocyclic aromatic radical whether or not fused, such as phenyl, biphenyl, and the like. The term "arylalkyl" means one or more aryl groups appended to an alkyl group, for example, the benzyl group.

Groups of derivatized compounds having a general core amidino-urea or diamidino-urea structure have been found to be highly potent interactive compounds which bind to the neuropeptide-Y receptor and may stimulate, not stimulate or partially stimulate a response pathway associated with that receptor thus acting as agonists, partial agonists, antagonists, or mixed agonists h; antagonists of neuropeptide-Y. These compounds have the general formula I

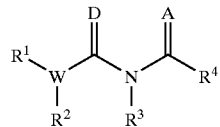

wherein
A is O, S or N—R, wherein R is lower alkyl ($C_1$-$C_8$);
D is O, S or N—$R^7$:
W is N, CH or C—$R^8$;
$R^1$ and $R^3$ are independently H, straight or branched, cyclic or acyclic, saturated or unsaturated $C_1$-$C_{14}$ alkyl radicals, optionally substituted by hydroxy, lower alkoxy, alkylthio, aryloxy or arylthio groups, wherein said aryl-bearing groups are optionally substituted by halogen, lower alkoxy, alkylthio, lower alkyl, trifluoromethoxy, trifluoroethoxy or trifluoromethyl groups, and optionally said alkyl groups are substituted by cyclic structures selected from the group consisting of rings having a ring size of from 3 to 10 atoms, such as cyclohexyl or cyclopentyl, or said alkyl groups are substituted by aromatic or heteroaromatic moieties, said aryl or heteroaryl groups optionally containing substituents on the aryl ring selected from the group consisting of lower alkyl, alkoxy, amino, lower alkylamino, lower acylamino, halogens, and trifluoromethyl or trifluoromethoxy groups;
$R^2$ is

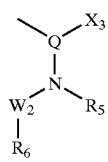

Wherein
$W_2$ is C=O, $SO_2$, C(O)NH; SO; or is absent;
Q is
(a) a substituted or unsubstituted (—$CH_2$—)$_z$ wherein z=1 to 12, and when —$CH_2$— is substituted, the substituting groups are lower alkyl, aryl or heteroaryl; and when z>1, at least one —$CH_2$— group is optionally replaced by a heteroatom selected from the group consisting of O, S, or a substituted or unsubstituted N, wherein the substituting moiety is selected from the group consisting of lower alkyl, aryl, heteroarylalkyl and hydrogen;
(b) a saturated carbocyclic or heterocyclic ring of the formula (—$CH_2$—)$_x$

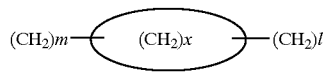

wherein 1 and m are 0–5, and wherein x=3–12, preferably 3–8, and optionally, one or more —$CH_2$— groups are substituted by a radical selected from the group consisting of saturated or unsaturated lower alkyl, cycloalkyl, aryl and heteroaryl; and optionally at least one of the —$CH_2$— groups is replaced by a heteroatom selected from the group consisting of O, S, Se and substituted or unsubstituted N, and when N is substituted, the substituting group is selected from the group consisting of lower alkyl, aryl, heteroaryl and hydrogen;
(c) a carbocyclic or heterocyclic aromatic ring of the formula (—CH=CH—)$_y$:

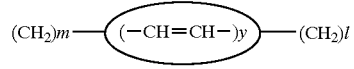

wherein 1 and m are 0–5, and wherein y≧2 and optionally at least one of the —CH— groups is substituted by $X^1$, $X^2$ or both $X^1$ and $X^2$ wherein X is any ring substituent, for example saturated or unsaturated, linear or branched alkyl groups, lower alkoxy groups or halogens, and optionally, at least one of the —CH— groups is replaced by N, or alternatively, one of the —CH=CH— groups is replaced by a heteroatom selected from the group consisting of O, S, Se and N—$R^{11}$; also optionally, at least one of the —CH=CH— groups is a junction to which another ring structure, either saturated or unsaturated can be fused, thus forming condensed aromatic or heteroaromatic systems selected, for example, from the group consisting of naphthalene, indole, benzofuran, quinoline, quinazoline and benzodioxane classes;
$X^3$ is a substituent on Q which can be H, lower alkyl, aryl, lower alkoxy, hydroxy, trifluoromethyl, and similar common ring substituents.
$R^4$ is selected from the group consisting of the following general formulas:

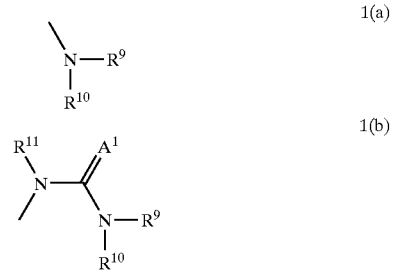

wherein $A^1$ is O, S, NH or N-lower alkyl or aryl;
$R^5$ to $R^{9,}$ $R^{11}$ and $R^{12}$ are independently selected from the group consisting of H, linear or branched, saturated or unsaturated, cyclic or acyclic, substituted or unsubstituted $C_1$ to $C_{14}$ alkyl radicals, or aryl or heteroaryl radicals, and when any one of $R^5$ to $R^9$, $R^{11}$ or $R^{12}$ is a substituted aryl or heteroaryl radical, the substituting group is selected from members of the group consisting of halogen, lower alkoxy, alkylthio, lower alkyl, trifluoromethoxy and trifluoromethyl, and when any one of $R^5$ to $R^9$, $R^{11}$ or $R^{12}$ is a substituted alkyl radical, the substituting moiety is selected from the group consisting of non-aromatic cyclic systems having from 3 to 14 ring atoms, and aromatic and heteroaromatic systems and heterocyclic rings having from 4–12 ring members, and said aromatic and heteroaromatic rings optionally are substituted by radicals selected from the group consisting of lower alkyl, alkoxy, amino, lower alkylamino, lower acylamido, halogens, perfluoroalkyl, and perfluoro-lower alkoxy; or
$R^6$ is H, $C_1$ to $C_{14}$ alkyl, straight or branched, cyclic or acyclic, saturated or unsaturated; aryl; heteroaryl; aryl-lower alkyl; heteroaryl-lower alkyl; condensed aryl-lower alkyl; condensed heteroaryl-lower alkyl; diaryl-lower alkyl; bis-heteroaryl-lower alkyl; or heteroaryl-lower alkyl-aryl; or partially or fully saturated derivatives thereof; or $R^6$ can be $R^{6'}$ which is $R^6$—NH or $R^6$—N-lower alkyl;

$R^{10}$ is hydrogen, $C_1$–$C_{12}$ alkyl, straight or branched, saturated or unsaturated, cyclic or acyclic groups, optionally containing double or triple bonds; aryl, optionally substituted with groups such as halogen, lower alkyl, alkoxy, aminoalkyl, di-(lower alkyl)-amino-lower alkyl, hydroxy; arylalkyl; aryloxyalkyl; 2-tetrahydrofurfuryl; 3-tetrahydrofuryl; terminal hydroxyalkyl with $C_2$–$C_{10}$ hydrocarbon chains and amidoalkyl such as 2-acetamidoethyl; or $R^9$ and $R^{10}$ can optionally form a 3 to 10- membered ring, preferably 4 to 8-membered, for example, piperidine, pyrrolidine, morpholine, piperazine, 4-methyl piperazine or tetrahydroisoquinoline.

The compounds of the present invention may have one or more asymmetric centers and it is intended that stereoisomers, as separated, pure, or partially separated stereoisomers or racemic mixtures thereof are included within the scope of the invention. Lower alkyl is defined to mean having from 1 to 8 carbon atoms.

The compounds of this invention are generally utilized as the free base or as a pharmaceutically acceptable derivative thereof. One example is an acid addition salt having the utility of the free base. Such salts are prepared in a conventional manner by treating a solution or suspension of the free base of formula I with one or more chemical equivalents of a pharmaceutically acceptable acid, for example, organic and inorganic acids, for example: maleic, fumaric, benzoic, ascorbic, pamoic, succinic, bismethylene salicylic, methanesulfonic, ethanedisulfonic, acetic, oxalic, propionic, tartaric, salicylic, citric, gluconic, lactic, malic, mandelic, cinnamic, citraconic, aspartic, stearic, palmitic, glycolic, p-aminobenzoic, glutamic, benzenesulfonic, hydrochloric, hydrobromic, sulfuric, phosphoric or nitric acids. Physiologically acceptable salts of a compound with an hydroxy group include the anion of said compound in combination with a suitable cation such as sodium or ammonium ion. "Physiologically acceptable" means non-injurious to the subject.

The compounds of the invention are of two general types containing either an amidino-urea group or diamidino-urea group as a core structure:

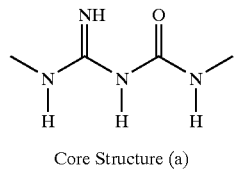

Core Structure (a)

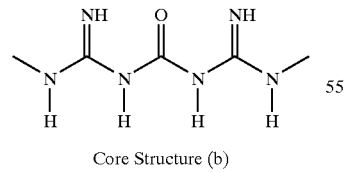

Core Structure (b)

said groups being derivatized with various aliphatic and aromatic moieties.

Core structure (a) comprises an amidino-substituted urea moiety and core structure (b) comprises a bis-amidino-substituted urea moiety. In each core structure, any of the imino N can optionally be further substituted as shown below by substitution according to the general formula I:

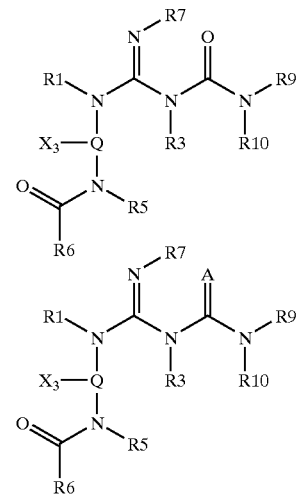

wherein $R^1$, $R^3$, $R^5$—$R^7$, $R^9$, $R^{10}$, $X^3$, an A are as defined above.

Preferred compounds have the structures

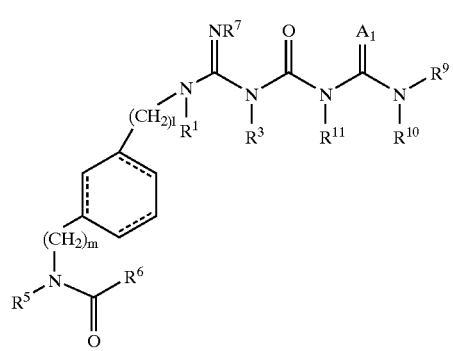

Figure 1a

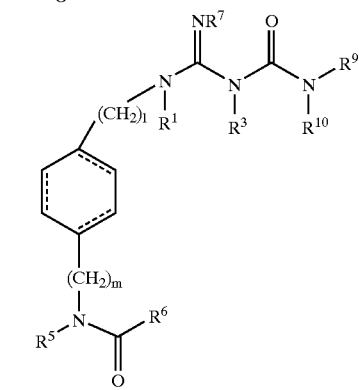

Figure 1b

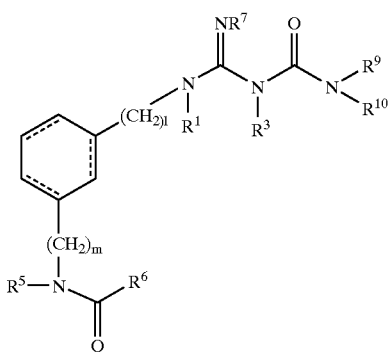

Figure 1c

Particularly preferred compounds have the structures

Wherein Y' and Y" are independent and can be H, lower alkyl, O-lower alkyl, halogen, CN, NO$_2$, OH, or other common aromatic ring substitutions.

Representative compounds of the present invention also include the following:

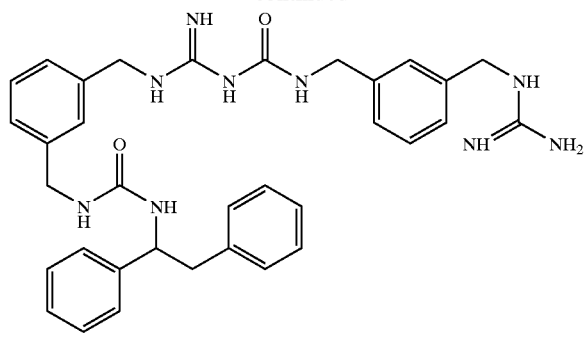
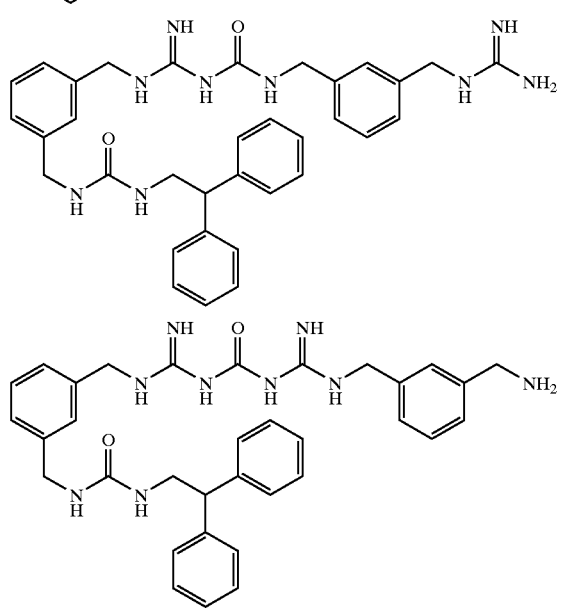
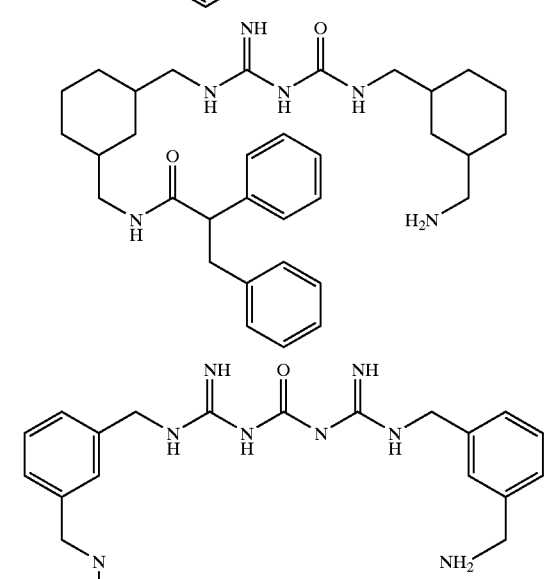
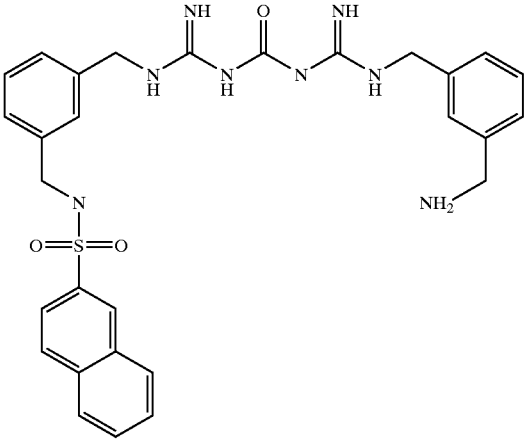
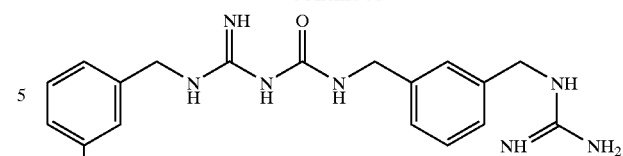
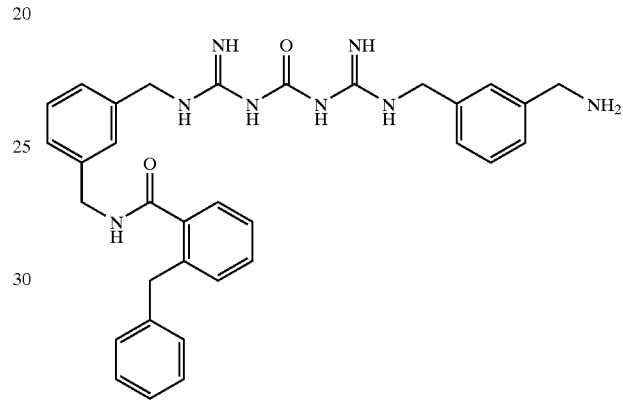
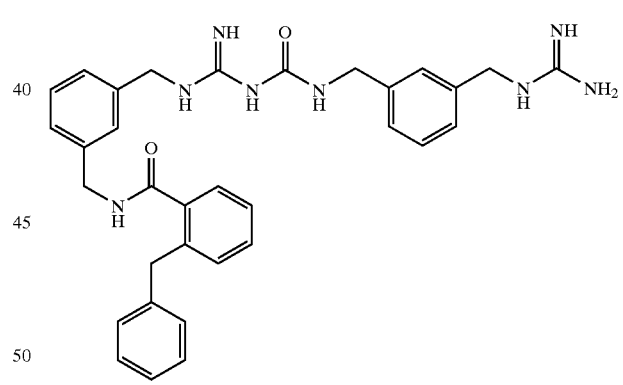
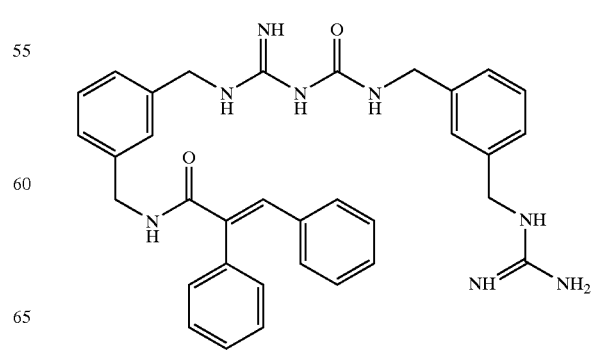

11
-continued
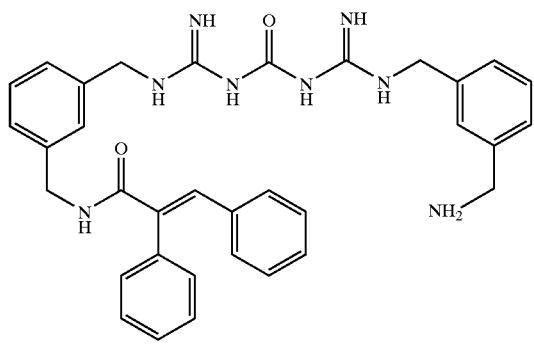
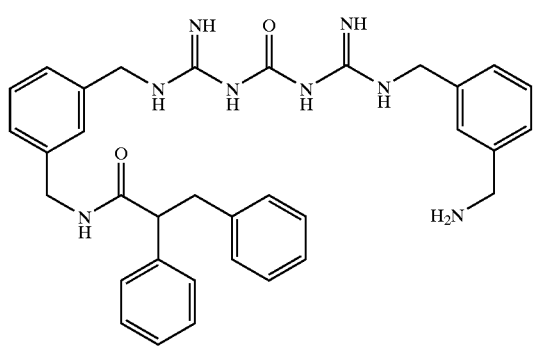
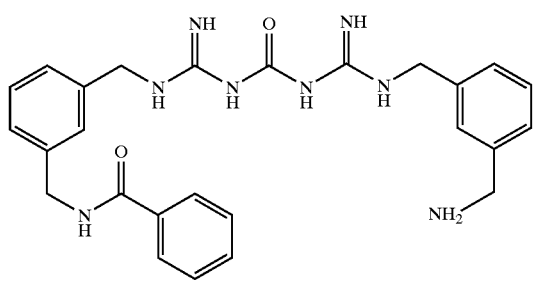
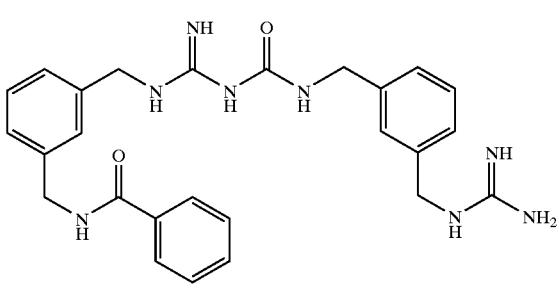
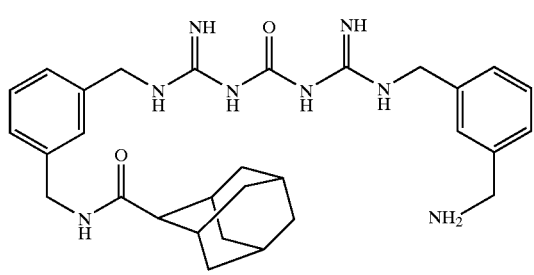
12
-continued
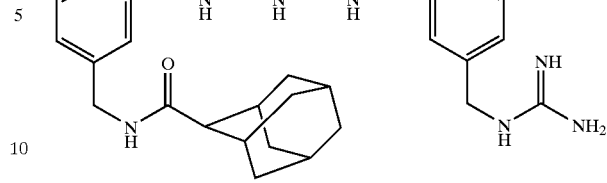
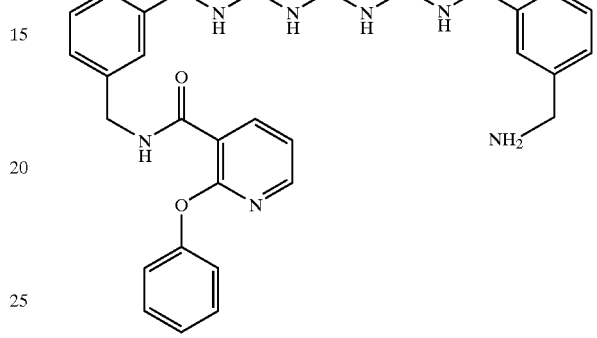
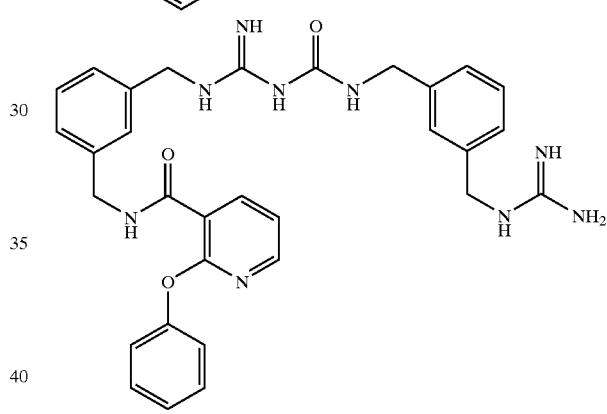
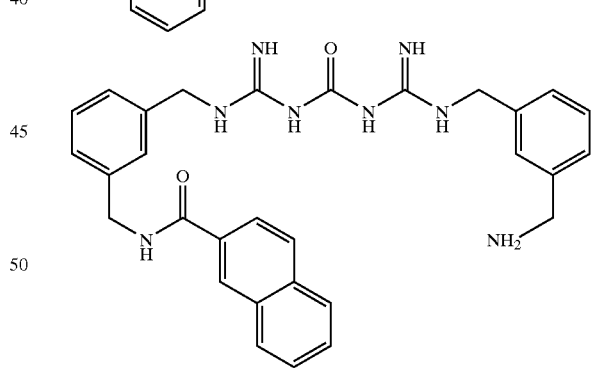
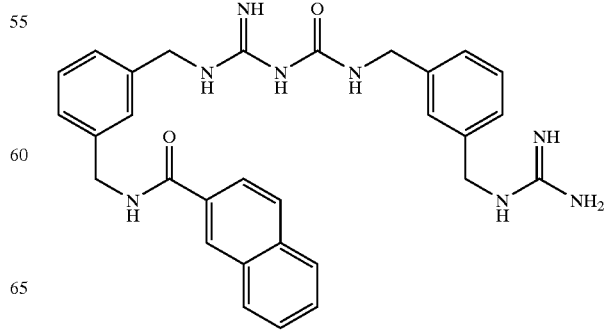

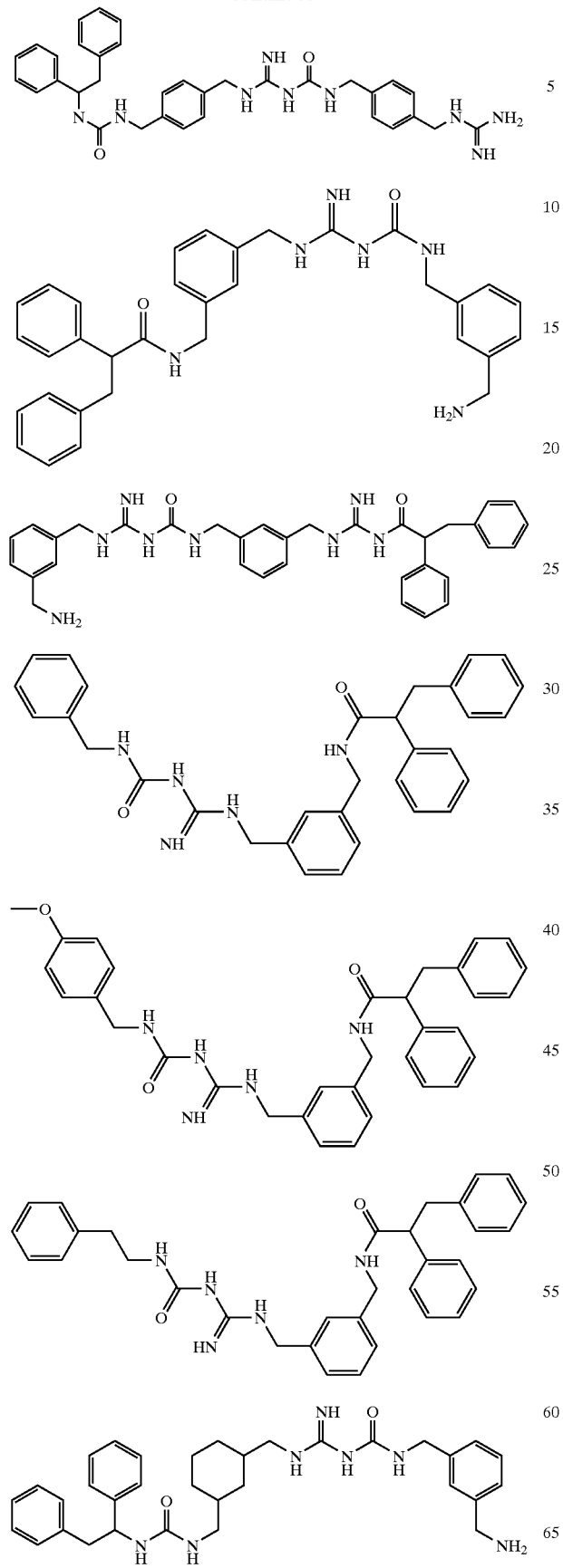
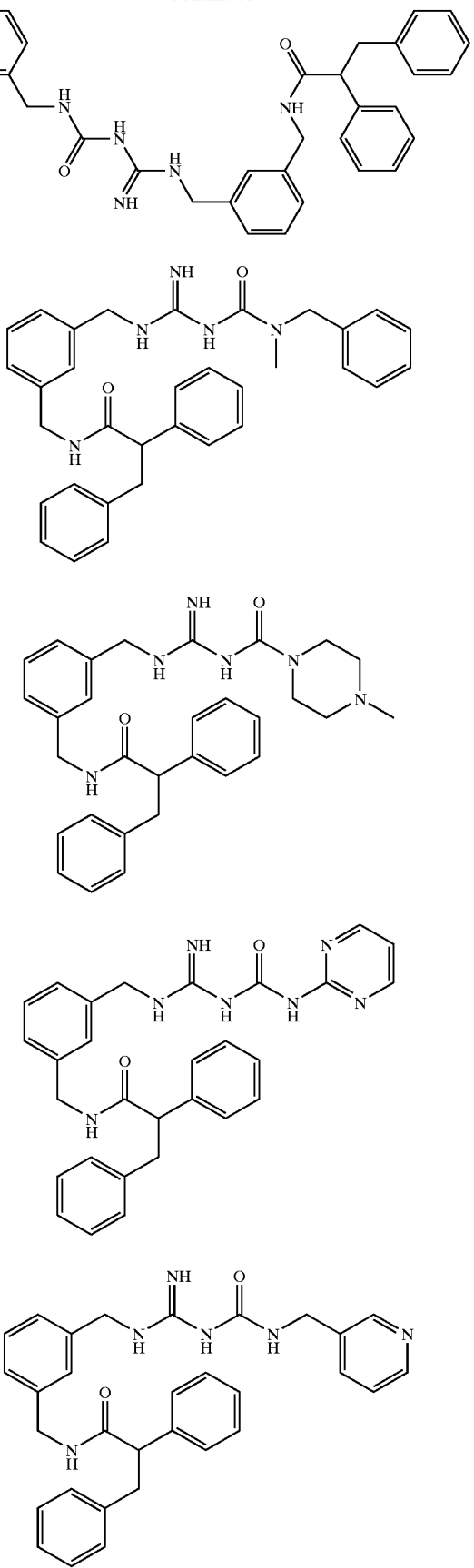

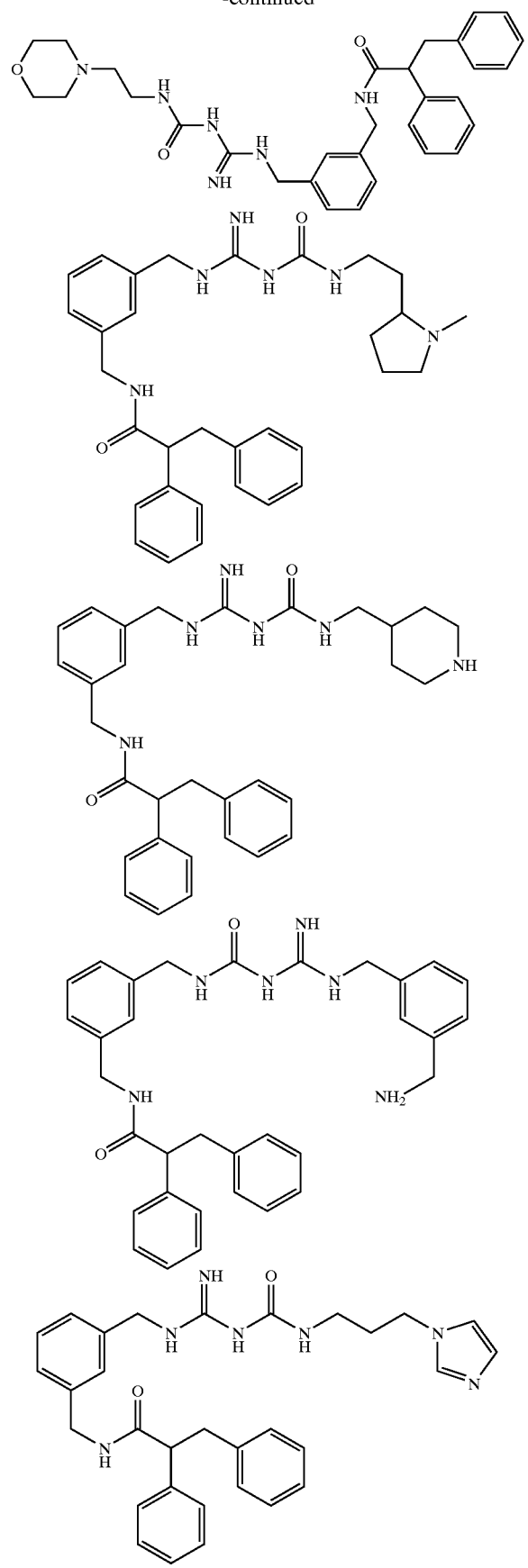
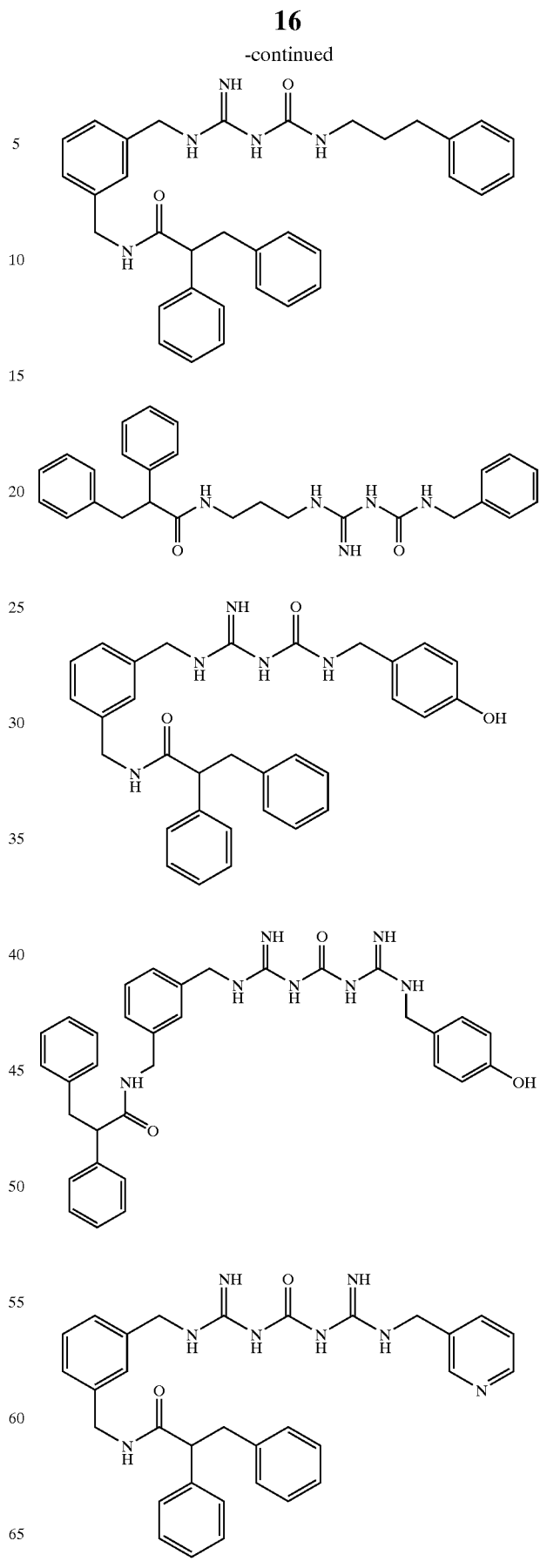

17
-continued
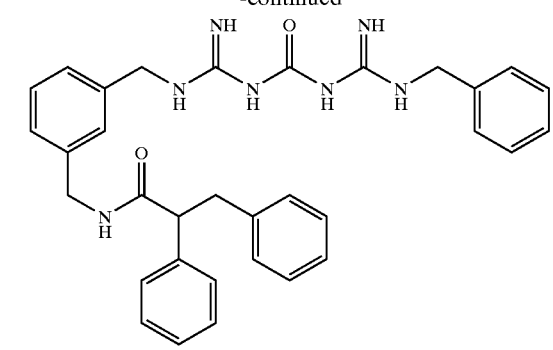
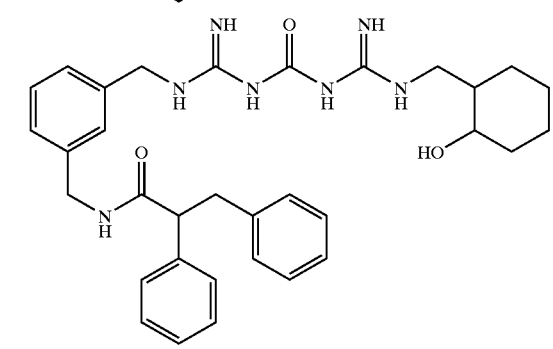
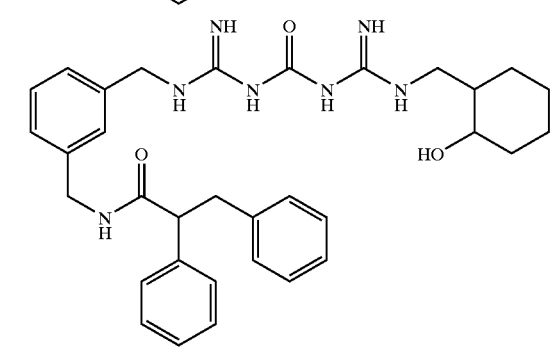
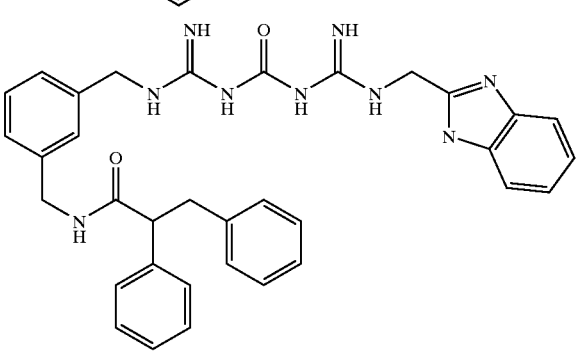
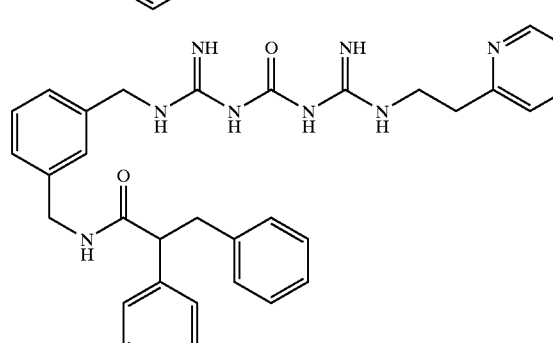
18
-continued
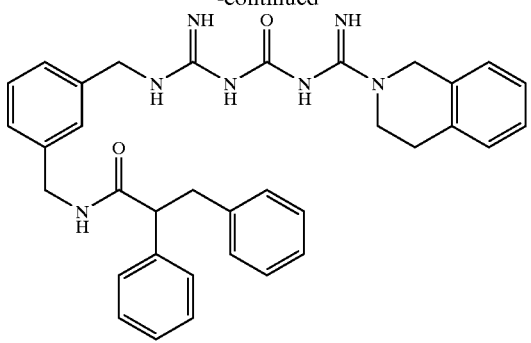
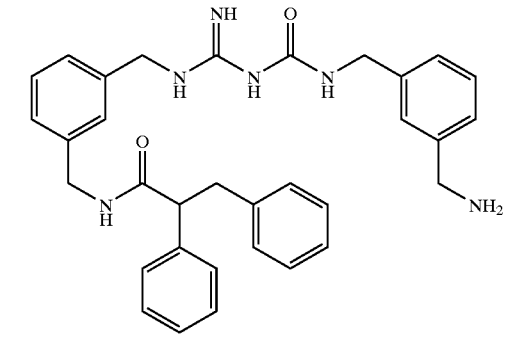
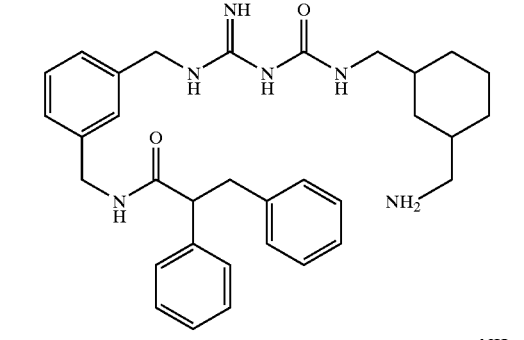
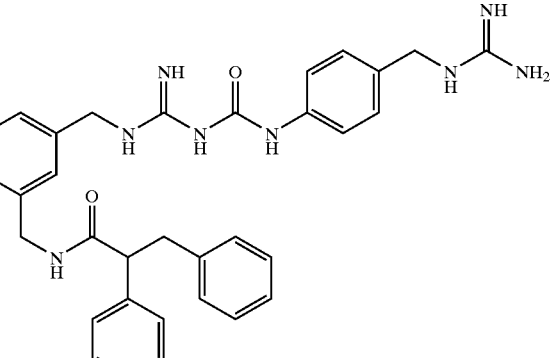
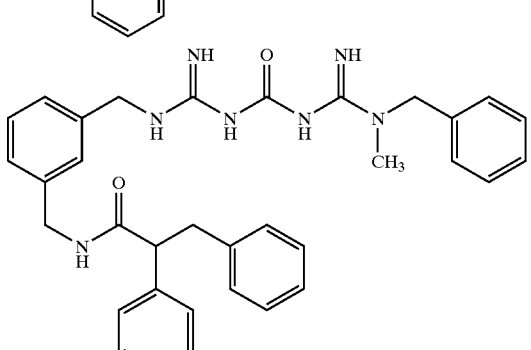

-continued
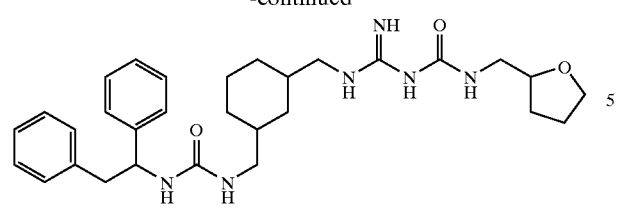
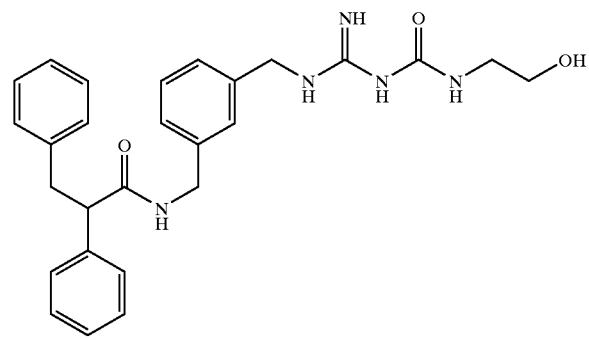
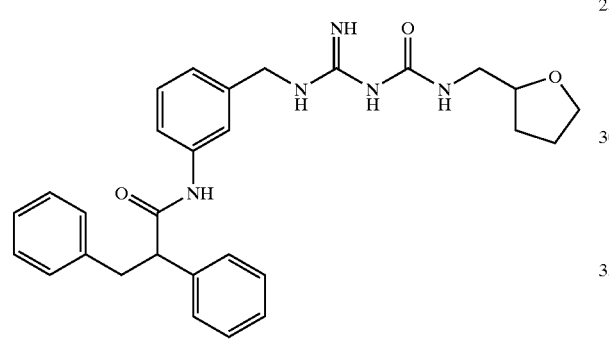
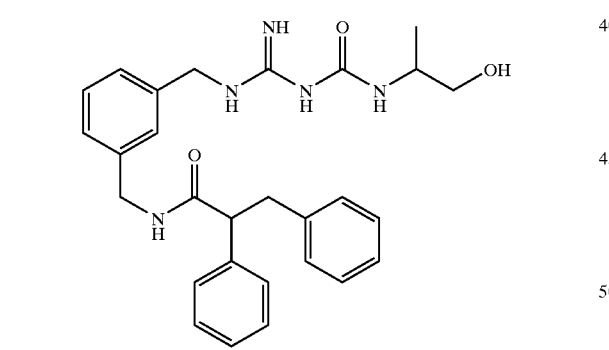
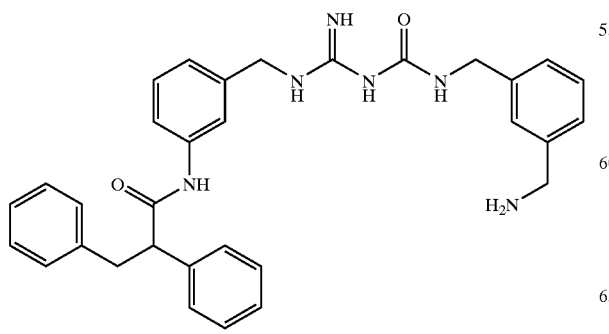
-continued
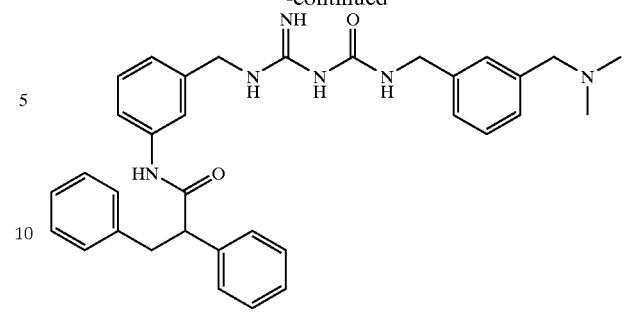
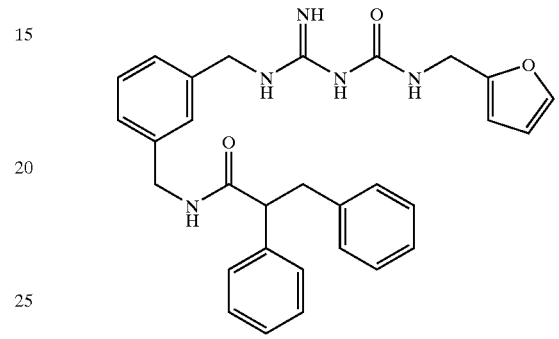
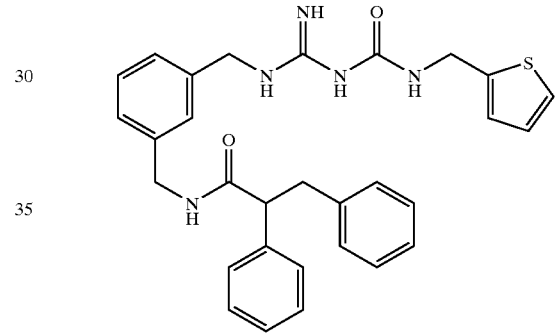
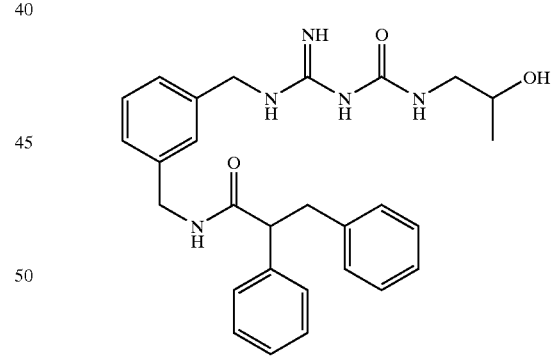
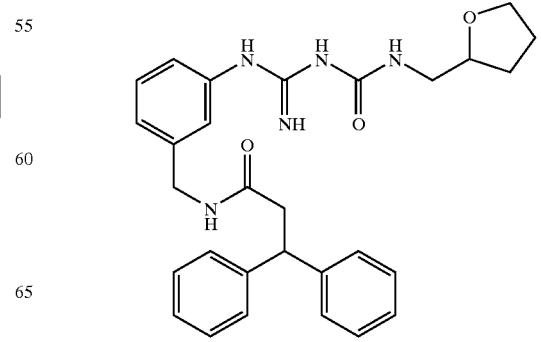

21
-continued
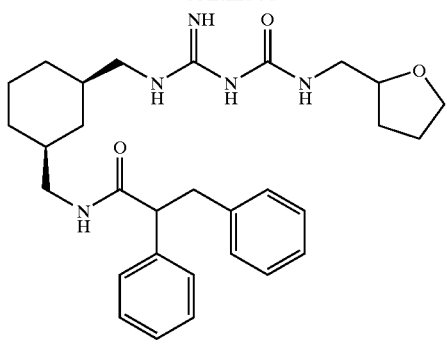
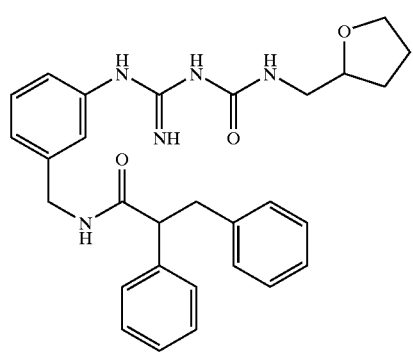
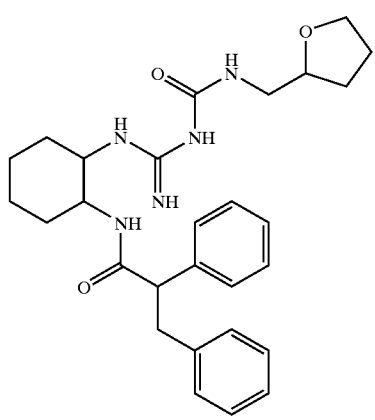
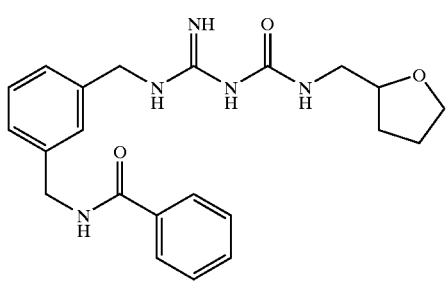
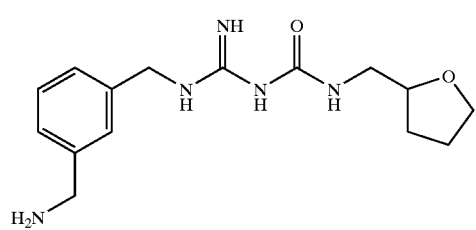
22
-continued
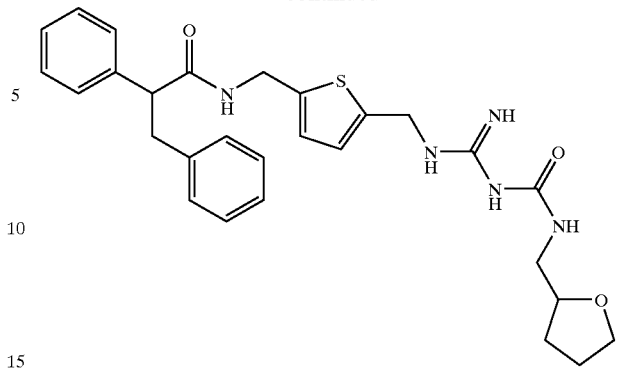
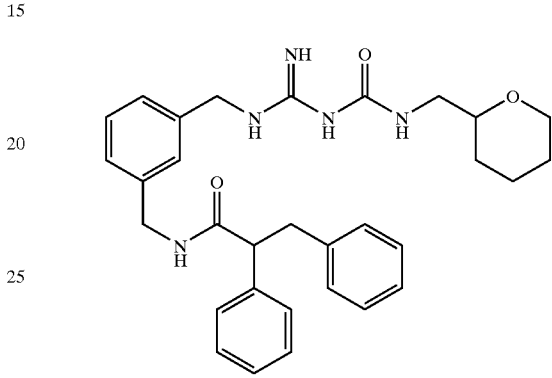
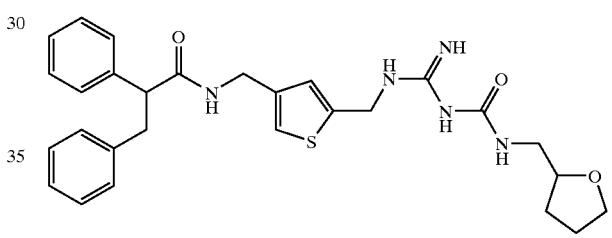
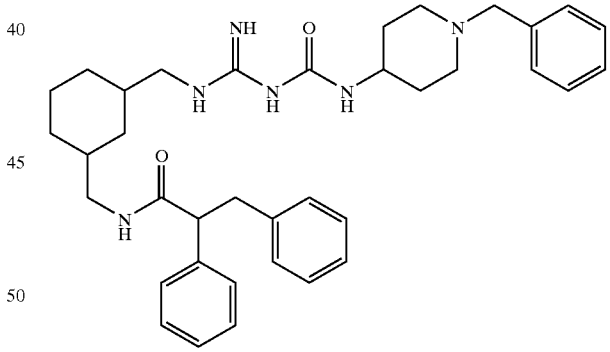

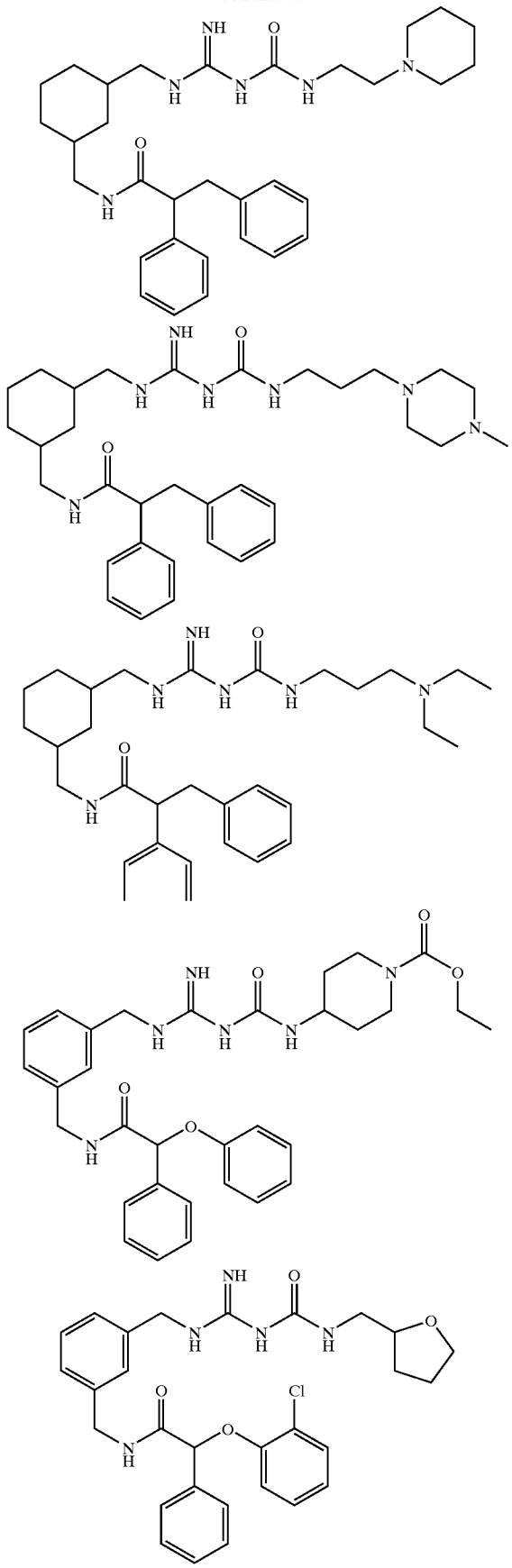

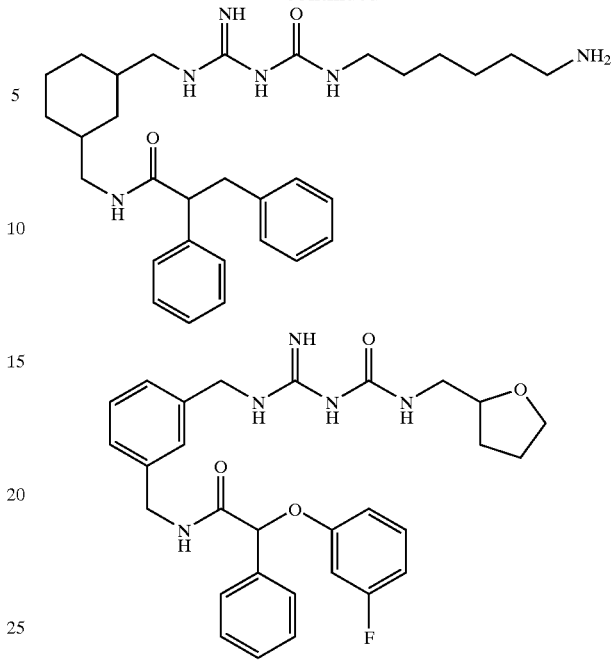

Depending on the varied structural features incorporated therein, the compounds of the invention either act peripherally without significant penetration of the blood-brain barrier to beneficially affect various physiological processes, or act centrally to beneficially affect various aspects of mammalian, including human, neurological disorders and behavior.

These compounds are specifically designed and are herein disclosed as pharmacological agents, useful for, but not limited to, the treatment of the following conditions: septic shock, anxiety. (anxiolytics), infertility, hypertension, congestive heart failure, obesity, type II diabetes, genitourinary dysfunction and other pathological conditions. These compounds are accordingly intended for specific use as feeding stimulants, fertility stimulants, bronchodilators, vasodilating agents to beneficially affect the reperfusion of ischemic organs and also as feeding suppressants, depending on the manner in which the particular compound interacts with the neuropeptide-Y receptor. The compounds of the invention, their stereoisomers, enantiomers, or mixtures and the use thereof in pharmaceutical formulations for the treatment of disease is within the scope of the invention. A marked difference in potency has been observed among enantiomers of the same compounds, and advantageous use of these structurally based differences is contemplated.

The compounds according to the invention, which may also be referred to as active ingredients, may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the condition to be treated, and the chosen active ingredient.

In general, a dose will be in the range of 0.01 to 200 mg per kilogram body weight of the recipient per day, more particularly, in the range of 0.1 to 120 mg/kg, preferably 1 to 90 mg/kg and most preferably 10 mg/kg/day. The desired dose is preferably presented as two, three or more subdoses administered in unit dosage forms, for example, containing 5 to 1500 mg, preferably 10 to 250 mg and most preferably 100 mg of active ingredient in unit dosage form.

For parenteral routes, such as intravenous, intrathecal, intramuscular and similar administration, typically doses are on the order of from about ½ to about one order of magnitude lower than the dose employed for oral administration.

The compounds may be administered alone or in combination with pharmaceutically acceptable carriers, in either single or multiple doses. Pharmaceutical preparations containing the compounds of the invention in combination with various carriers are produced by conventional dissolving and lyophilizing processes to contain from approximately 0.1% to 100%, preferably from approximately 1% to 50% of the active ingredient. They can be prepared as ointments, salves, tablets, capsules, powders or sprays, together with effective excipients, vehicles, diluents, fragrances or flavor to make palatable or pleasing to use.

For parenteral administration, solutions of the novel compounds of formula I in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art. Suitable pharmaceutical carriers include inert solid diluents or fillers, sterile aqueous solution and various organic solvents. The pharmaceutical compositions formed by combining the novel compounds of formula I and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient in the form of powder or granules, as a solution or suspension in an aqueous or nonaqueous liquid, or as an oil-in-water or water in oil liquid emulsion.

Tablets or other non-liquid oral compositions may contain acceptable excipients, known to the art for the manufacture of pharmaceutical compositions, comprising diluents, Do such as lactose or calcium carbonate; binding agents such as gelatin or starch; and one or more agents selected from the group consisting of sweetening agents, flavoring agents, coloring or preserving agents to provide a palatable preparation. Moreover, such oral preparations may be coated by known techniques to further delay disintegration and absorption in the intestinal tract.

Aqueous suspensions may contain the active ingredient in admixture with pharmacologically acceptable excipients, comprising suspending agents, such as methyl cellulose; and wetting agents, such as lecithin or long-chain fatty alcohols. The said aqueous suspensions may also contain preservatives, coloring agents, flavoring agents and sweetening agents in accordance with industry standards.

Preparations for topical and local application comprise aerosol sprays, lotions, gels and ointments in pharmaceutically appropriate vehicles which may comprise lower aliphatic alcohols, polyglycols such as glycerol, polyethylene glycol, esters of fatty acids, oils and fats, and silicones. The preparations may further comprise antioxidants, such as ascorbic acid or tocopherol, and preservatives, such as p-hydroxybenzoic acid esters.

Parenteral preparations comprise particularly sterile or sterilized products. Injectable compositions may be provided containing the active compound and any of the well known injectable carriers. These may contain salts for regulating the osmotic pressure. Suitable pharmaceutical carriers include inert solid diluents or fillers, sterile aqueous solution and various organic solvents. The pharmaceutical compositions formed by combining the novel compounds of formula I and the pharmaceutically acceptable carriers are then readily administered in a variety of dosage forms suitable for the disclosed routes of administration. The formulations may conveniently be presented in unit dosage form by methods known in the art of pharmacy.

The compounds of the invention are prepared as described below and are screened for receptor-binding efficacy using the neuropeptide-Y receptor binding assay of Example 7.

Synthesis of amidino-urea and diamidino-urea derivatives of the Invention: The invention is also directed to processes for preparing such compounds as well as to pharmaceutical compositions containing them and methods of use.

The compounds of the invention are of two general types each having one of the core structures of the formula below:

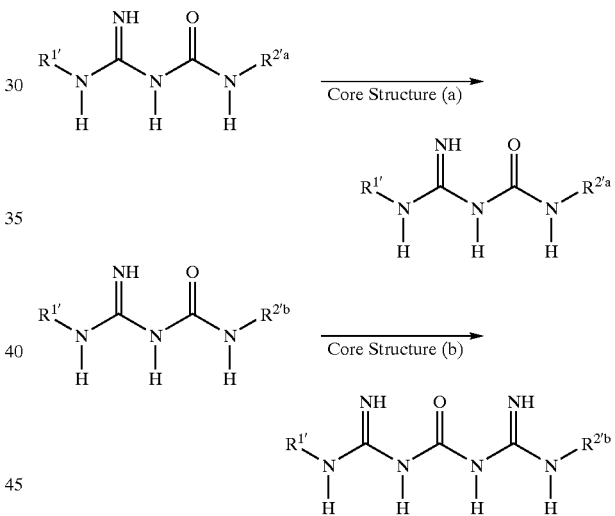

Core structure (a) comprises an amidino-substituted urea moiety and core structure (b) comprises a bis-amidino-substituted urea moiety. In each core structure, any of the imino N can optionally be further substituted as shown in the general formula I.

To form the compounds of the invention, derivatives of the core structures are prepared by substitutions $R^{1'}$ and $R^{2'}$ at each terminal amine of the core structures as disclosed below.

General Scheme of Synthesis

The compounds of formulas 1(a) and 1l(b) shown above, which are useful in the synthesis of the derivative compounds of the invention, can be synthesized by reacting intermediates 2 and 3 as shown in Schemes I and II:

Scheme I:

Step 1:

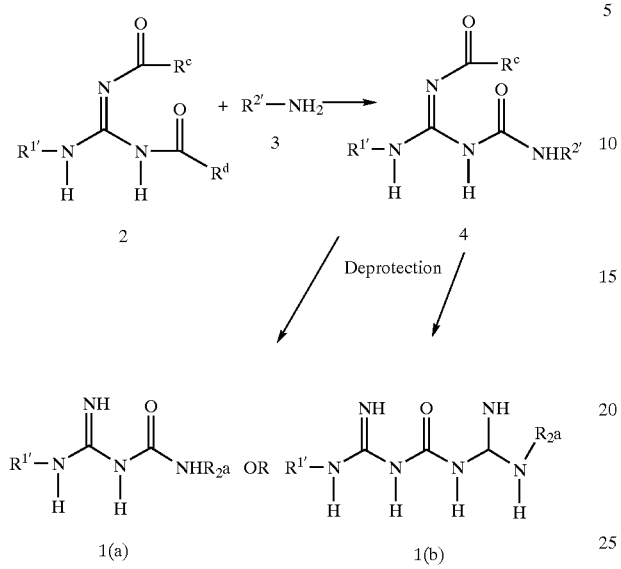

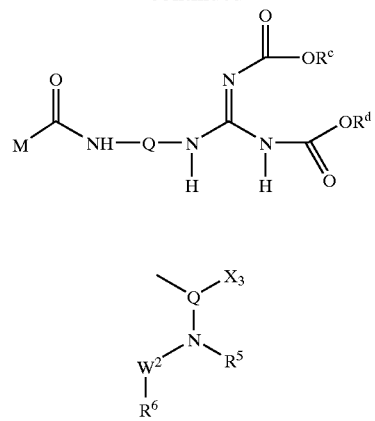

and wherein $W^2$, $R^5$, $R^6$ and $X^3$ are as previously defined. $R^c$ and $R^d$ are independent and can be lower alkyl or aryl, for example, methyl, ethyl, tert-butyl or phenyl; and M is $R^6$ as previously defined.

Scheme I demonstrates the preparation of R1', R2'-substituted core structures 1 (a) and 1(b) by:

(1) Amidation of blocked intermediate 2 using $R^{2'}$—$NH_2$; and
(2) Deblocking of the imino group of intermediate 4 by hydrolysis of $OR^c$ group thereof, followed by spontaneous decarboxylation.

To produce 1, the substituted (or unsubstituted, blocked) guanidine carbamates 2 are reacted with compounds 3 according to Scheme I. The reactions are performed by stirring or otherwise agitating the components at various temperatures ranging from or about 0° C. to from and about 40° C., preferably 10° C. to from and about 80° C., preferably in an inert atmosphere, for example, nitrogen or argon, in polar or nonpolar, aprotic, protic or aqueous solvents which include but are not limited to: ethers such as tetrahydrofuran, ethylene glycol methyl ester (glyme), diglyme, dioxane, diethyl ether, dibutyl ether, methyl tert-butyl ether, anisole and the like; esters, exemplified by ethyl acetate or butyl acetate; hydrocarbons, exemplified by hexane, heptane, toluene, xylene and the like; water or mixtures of water and any organic solvents, both water miscible, and water-immiscible; dimethylformamide, dimethylacetamide, tetramethylurea; halogenated organic solvents, for example, chloroform, dichloromethane, trichloroethylene, chlorobenzene and dichlorobenzenes; alcohols, for example, methanol, ethanol, isopropyl alcohol, tert-butyl alcohol, phenol, ethylene glycol, and monoethers of ethylene glycol, also known as carbitols.

The reaction of 2 with 3 can also be performed neat (without solvent) by stirring or otherwise agitating the components at temperatures ranging from or about 0° C. to from and about 140° C., preferably from and about 110° C. to and about 80° C. The reactions can be performed in the absence of a catalyst or presence of various catalysts in various amounts ranging from or about 0.01 mol equivalent to 10 mol equivalent, preferentially from and about 0.1 to and about 2 mol equivalent. These include organic bases, for example, triethylamine, diisopropylethylamine and pyridine; or inorganic bases, for example, alkali metal hydrides such as sodium hydride, alkali metal alkoxides such as potassium tert-butoxide, alkali metal fluorides such as cesium or potassium fluoride, alkaline earth hydrides such as calcium hydride; or tetraalkyl ammonium alkoxides such as benzyl trimethylammonium methoxide.

Scheme II: Method A (1) guanidination

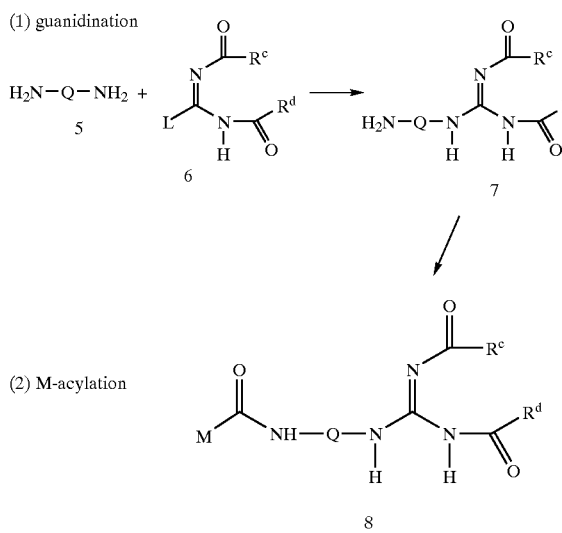

(2) M-acylation

Scheme II: Method B (1) M-acylation

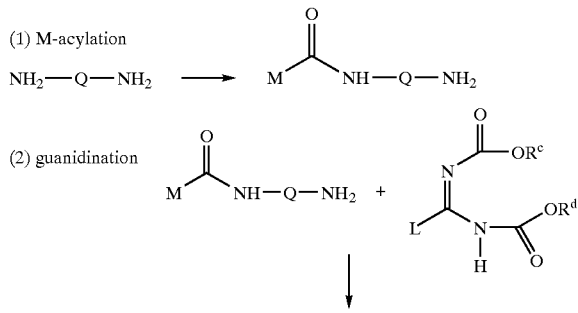

(2) guanidination

The reaction products 4 are freed of the solvent, if necessary, by distillation of the solvent out of the mixture, either at atmospheric pressure or in vacuum. The products are then purified (if necessary) by any of the purification methods known to those skilled in the art, or can be used directly without purification for the next step. The methods useful for the purification include but are not limited to: chromatography on normal phase silica gel, alumina, kieselguhr, Celite, Florisil, microcrystalline cellulose, and similar adsorbents with various solvents used as eluents, either alone or in mixtures; for example, toluene, hexane, ethyl acetate or dichloromethane; or a mixture of solvents such as hexane-ethyl acetate.

Other chromatographic methods useful for the purification of the product 4 include reverse-phase chromatography on C-18 or analogous solid supports, using solvents such as water-acetonitrile, water-methanol, optionally containing various buffers or other additives, such as trifluoroacetic acid or phosphate buffer. Other methods useful for the purification include extraction of the reaction product and partitioning into various heterogeneous solvent mixtures such as water-ethyl acetate, water-dichloromethane, water-toluene and the like. Other purification methods include recrystallization of crystalline products from various solvents exemplified by ethyl acetate, hexane, isopropyl alcohol and the like; or precipitation (dissolution of the crude product in a solvent the reaction product 4 is soluble in and gradually adding a solvent (precipitant) which precipitates the desired material in purified form (which is then recovered by filtration), or precipitates impurities which are filtered off and the solution is concentrated to obtain the purified 4 material. Examples of solvents used for dissolving the reaction product 4 include ethyl acetate or dichloromethane, an example of the precipitant solvent includes hexane.

The product 4 is usually obtained as a light yellowish foam or a glassy material. The next step consists of removal of the NH blocking groups from the above intermediate 4. When $R^3$ is tert-butoxycarbonyl (t-BOC), the above product is treated with an acidic reagent in a solvent such as water, dioxane, diethyl ether, dichloromethane, toluene, ethyl acetate and the like. The acid reagent can be one of the following: trifluoroacetic acid; hydrogen chloride either as a gas or a solution in a solvent such as water (hydrochloric acid), diethyl ether or dioxane; hydrogen bromide solution in water (hydrobromic acid) or in acetic acid; formic acid; glacial acetic acid and the like. The reaction can be performed at from about −10° C. to about 60° C., preferably from about 20° C. to about 40° C.

When the reaction is complete, the solvent is removed and the residue may be purified by any of the purification methods outlined above, preferentially reverse phase chromatography, using acetonitrile-water gradient. The product as its trifluoroacetate salt is usually obtained after removal of the solvents in vacuo (e.g. by lyophilization) as a white to off-white amorphous solid. When R3 is benzyl (CBZ), the above product is treated with hydrogen gas at atmospheric pressure or under pressure of from and about 10 to and about 60 psi, or with a hydrogen transfer agent such as 1,4-cyclohexadiene in the presence of a palladium catalyst, either neat, or on various supports, such as charcoal, barium sulfate and the like, the preferred catalyst being commercial 10% palladium on carbon. The hydrogenation can be performed in the presence of various acids, such as hydrochloric acid which provide the corresponding salt counterion. The products are obtained after removal of the solvents in vacuo (e.g. by lyophilization) as a white to off-white amorphous solid. They can be further purified.

The synthesis of these substituted compounds, for example, any of the preferred compounds having the structures of 1(a)–1(n), is carried out in a manner analogous to that for the specific compounds shown in Schemes I and II.

To prepare the compound having a derivatized core structure 1(a) according to Scheme I an amine such as, for example 1,3-(bis-aminomethyl)benzene, is reacted with a guanidinating reagent (di-BOC-amidino-pyrazole) to yield the guanidinated product, for example, (N-(di-BOC-amidino)-1,3-diaminoxylene (3')). The product is then acylated, using for example, 2,3-diphenylpropionyl chloride to yield the acylated guanidinated diamine, for example, N-(di-BOC-amidino)-N'-(2,3-diphenylpropionyl)-1,3-diaminoxylene (5'). The product is again reacted with a diamine, for example 1,3-(bis-aminomethyl)benzene (1), to yield an amidated guanidine derivative.

To prepare a compound having a derivatized core structure 1(b) according to Scheme II, a procedure similar to that described above is followed, with the exception that the guanidinated, M-acylated diamine, for example, N-amidino-N'-(2,3-diphenylpropionyl)-1,3-diaminoxylene (9'), is condensed with an amidinated diamine or its derivative, for example (8'), to yield a derivatized bis-amidino urea (11').

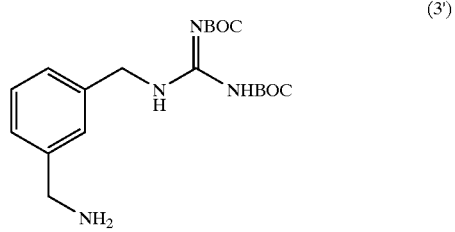

(3')

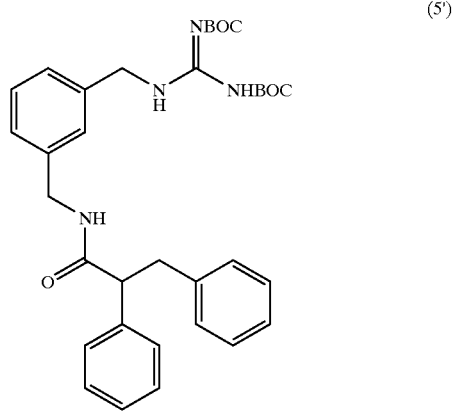

(5')

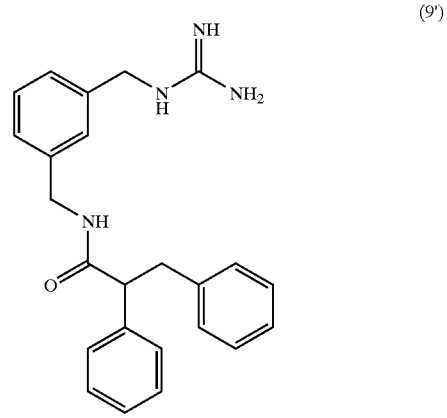

(9')

-continued (11')

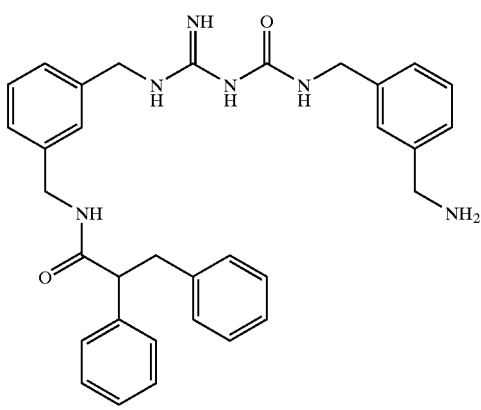

The condensed product is deblocked to yield the derivatized product having the 1(b) core structure.

Preparation of the Intermediates (3) of Scheme 1

The $R^{2'}$ group of Intermediate 3 of Scheme 1 is either $R^{2'a}$ or $R^{2'b}$. $R^{2'a}$ can be substituted or unsubstituted $C_1$ to $C_{10}$ branched or straight chain alkyl groups, carbocyclic or heterocyclic 3–12 membered rings, aryl, heteroaryl, arylalkyl, heteroarylalkyl. The substituents or the $R^{2'}$ moieties may be primary, secondary or tertiary amines, hydroxy, or lower alkoxy groups. Preferred $R^{2'a}$ groups are

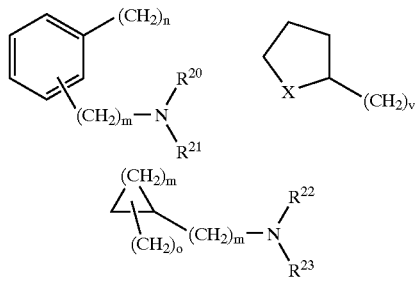

wherein n, m, and o are 0 to 6, preferably 1–3; v is 0–6, preferably 1–2; $R^{20}$ to $R^{23}$ are any substituent as defined above for $R^5$ respectively and X is O,S, NH or N-alkyl.

$R^{2'b}$ is prepared from $R^{2'a}$ by amidination thereof:

$R^{2'a}$—$NH_2$→$R^{2'a}$-amidino=($R^{2'b}$)

The compounds of general formula 3 wherein $R^{2'}$ is $R^{2'b}$ are obtained by reacting the appropriate amine $R^{2'a}$ with any of the guanidination agents known to those skilled in the art, for example, 1-amidinopyrazole, S-methylisothiourea sulfate, according to the method and the reagents shown below.

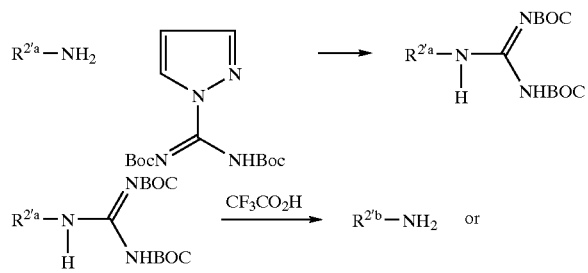

-continued

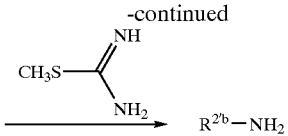

Either of the amine intermediates 3 is then utilized in the next step and reacted with 2 to form the amidated product 4 either in their crude state or are purified by any of the standard purification methods, for example, chromatography, before use in the next step.

The reagents necessary to prepare the amidinating reactants are either commercially available (Aldrich, Milwaukee, Wis.) or they can be obtained by the methods already described in the organic chemistry literature.

Using $R^{2'a}$—$NH_2$ as a reactant in the amidation step, one obtains a product having core structure (a) amidino-urea; using $R^{2'b}$—$NH_2$ as a reactant, where $R^{2'b}$ comprises an amidino moiety, one obtains a product having core structure (b), diamidino-urea.

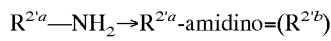

Core Structure (a)

Core Structure (b)

Preparation of Intermediates of the General Formula 8

Intermediate reactants of general formula 8 (or 2) having the formula

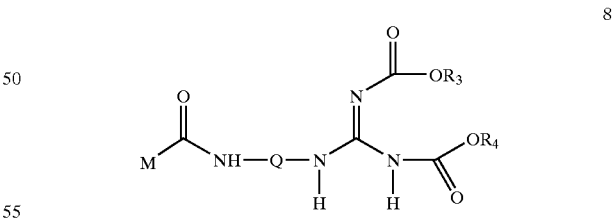

8 are prepared according to Scheme II for use in a manner similar to reactant 2 in the synthesis of Scheme I. Method A of Scheme II comprises a step of guanidinylation of a diamine comprising a Q species followed by M-acylation at the terminal amine thereof. Method B comprises, first, M-acylation of the diamine (or mono-protected diamine by a group such as BOC or CBZ, followed by deprotection), followed by guanidination.

The acylations are performed using method generally known to those skilled in the art and described in the standard works such as Houben-Wyle, Methoden de Organisch Chemie (Methods of Organic Chemistry) Georg-Threme, Verlag Stuttgart, Germany, namely under conditions which are known and suitable for the reaction considered.

The functionalities are defined as M, wherein M is $M^1$ or $M^2$, wherein $M^2$ is $M^1$—NH— and $M^1$ is, for example, straight or branched chain alkyl or ester group, aryl, arylalkyl, diarylalkyl, arylalkoxy, arylthio, heteroalkyl, heteroarylalkyl.

Preferably, M is one of the following structures

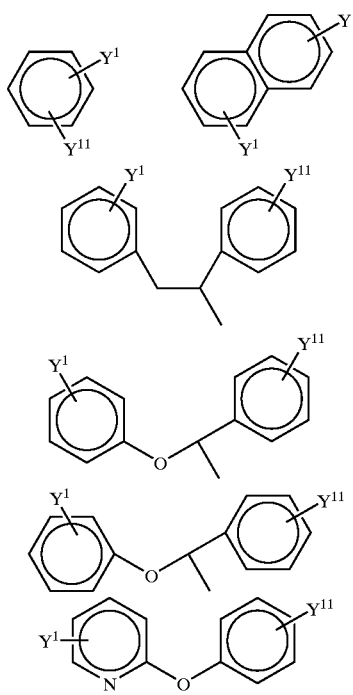

wherein all X's are common ring substitutes.
Q is preferably

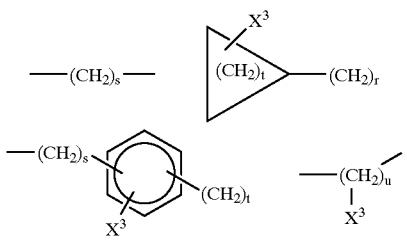

wherein $X^3$ is as defined above; r, s, t and u are 0–10, preferably 2–6; t is 1–10, preferably 2–6, and u is 0–10, preferably 2–6.

The M-acylations can be performed using standard acylating agents such as acyl halides, (esp. chlorides), imidazolides, anhydrides, isocyanates, and other conventional agents.

The reactions are performed in organic solvents such as chloroform, toluene, dichloromethane, tetrahydrofuran, and similar solvents at temperatures ranging from about −78° C. to about 80° C., preferably between about 0° C. and 30° C., optionally in the presence of organic tertiary bases such as triethylamine, pyridine, diisopropylethyl amine and similar agents. The acylations can also be performed in aqueous media under usual conditions generally known as Schotten-Baumann procedures using sodium hydroxide as a base and an acid chloride as the acylating agent.

Method A:

According to Scheme II, Method A, guanidination of the Q-species diamine using a di-blocked guanidination reagent bearing a leaving group L is followed by M-acylation at the free terminal amine group. According to Method B, the steps of the method are reversed, and acylation of a Q-species diamine is followed by guanidination at the terminal amine. The guanidination is performed in either method by reacting a reagent having a substituted or unsubstituted transferable amidino group connected to L with an appropriate primary or secondary amine in an organic solvent such as tetrahydrofuran (THF) at temperatures ranging from about 0° C. to about 110° C., preferably from about 20° C. to about 60° C. Such reagents and reactions have been previously described in the literature. The guanidination reagents can be, for example,

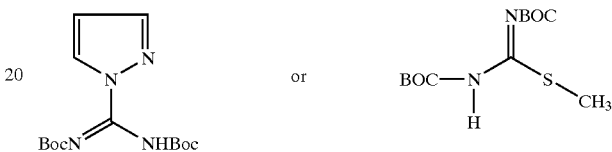

wherein the leaving group, L, is 1-pyrazolyl or $CH_3$—S, and the amino N's and imino N's are blocked with t-Boc groups. The reagent is prepared by modifications of the literature procedure (Bernatowitz, M. S. et al. (1992) J. Org. Chem 57:2497).

The reactions are performed in an organic solvent such as THF or aqueous solvent at from about 0° C. to about 80° C., optionally in the presence of a base such as sodium hydroxide, triethylamine, pyridine and the like. Amino blocking agents useful in the above methods are disclosed in Bodansky, M. *Principles of Peptide Synthesis* Springer-Verlag, Berlin (1984).

The following synthesis protocols refer to intermediate compounds and final products identified by number in Schemes I–IV. The preparation of the compounds of the present invention is described in detail using the following examples, but the chemical reactions described are disclosed in terms of their general applicability to the preparation of the NPY ligands of the invention. Occasionally, the reaction may not be applicable as described to each compound included within the disclosed scope of the invention. The compounds for which this occurs will be readily recognized by those skilled in the art. In all such cases, either the reactions can be successfully performed by conventional modifications known to those skilled in the art, that is, by appropriate protection of interfering groups, by changing to alternative conventional reagents, or by routine modification of reaction conditions. Alternatively, other reactions disclosed herein or otherwise conventional will be applicable to the preparation of the corresponding compounds of the invention. In all preparative methods, all starting materials are known or readily preparable from known starting materials; all temperatures are set forth in degrees Celsius; and, unless otherwise indicated, all parts and percentages are by weight. Positive ESI spectra were recorded on a Finnegan SSQ 7000.

It is believed that one skilled in the art can, using the preceding description, utilize the invention to its fullest extent. The following preferred embodiments are, therefore, to be construed as merely illustrative and not limitative for the remainder of the disclosure in any way whatsoever. The structural description of the compounds is to be preferred over nomenclature.

EXAMPLE 1

The Synthesis Procedures of Example 1 Proceed Through the Steps of the Following Scheme III

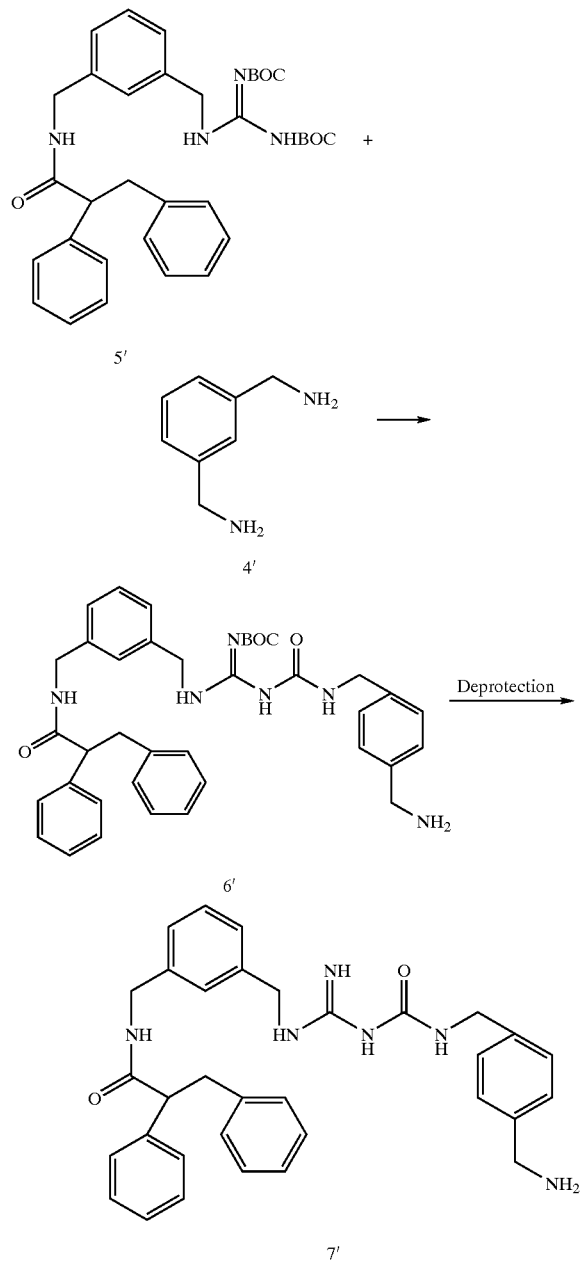

Preparation of N-[3-(1,2-diphenylpropionylamidomethyl-phenylmethyl-amidino)]-N-(3-aminomethyl-phenylmethyl) urea (7')
N-(di-BOC-amidino)-1,3-diaminoxylene (3')

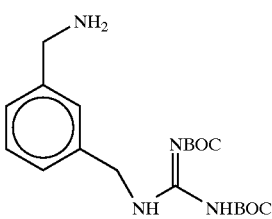

To a solution of 1,3-bis-aminomethylbenzene 1 (30.1 g, 221 mmol) in 500 mL of THF was added (N,N'-di-Boc-amidino)-pyrazole 2 (34.3 g, 110.5 mmol). The mixture was stirred for 2 hours at room temperature. The solvent was removed in vacuum under 40° C., and the resulting oily residue was purified on a silica gel column (25–50% hexane/ethyl acetate) to give 3' (41.8 g, 66%) as a pale yellow oil.
$^1$H-NMR (CDCl$_3$, 300 MHz)δ 1.48 (s, 9H), 1.52 (s, 9H), 3.05 (s (broad), 2H), 3.87 (s, 2H), 4.61 (d, J=5.2 Hz, 2H), 6.33 (t, J=2.1 Hz, 1H) 7.18–7.60(m, 4H), 8.57 (s broad, 1H), 11.5 (s broad, 1H).
MS (ESI) M/Z (relative intensity) 379 (M+100%) 337 (22%), 27.9 (10%), 179 (20%).

2,3-Diphenylpropionyl Chloride 25 g of 2,3-diphenylpropanoic acid was dissolved in 80 mL of SOCl$_2$ (10 eq.). The reaction mixture was stiffed under N$_2$ overnight at room temperature. Extra SOCl$_2$ removed by evaporation. 2,3-Diphenylpropionylchloride (28 g) was obtained as an oil and used without purification.
N-(di-BOC-Amidino)-N'-(2,3-diphenylpropionyl)-1,3-diaminoxylene (5')

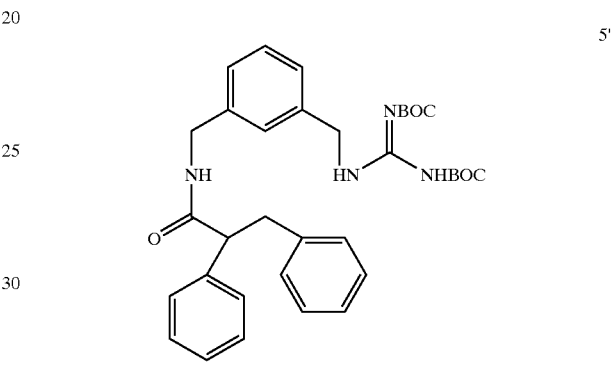

To a precooled solution (0° C.) of 3 (27.4 g, 72.3 mmol) in 300 mL of CHCl$_3$, Et$_3$N (7.3 g, 72.3 mmol) and 2,3 diphenylpropionylchloride (17.6 g, 72.3 mmol) was added. The mixture was stirred for 1 hour at room temperature. The solution was washed with water and brine and concentrated to dryness. The crude residue was dissolved in minimum amount of EtOAc and 300 mL of hexane was added. 5 (30.1 g, 71% yield) was collected as a white precipitate.
$^1$H-NMR (CDCl$_3$), 300 MHz)δ 1.46 (s, 9H), 1.49 (s, 9H), 2.99 (dd, J=6.1 Hz, J=13.1 Hz, 1H), 3.59 (dd, J=8.6 Hz, J=39 Hz, 14), 3.60 (dd, J=8.7 Hz, J=19.9 Hz, 1H), 4.09 (dd, J=5.2, J=15.1, 1H), 4.31 (dd, J=6.2, J=15.0, 1H), 4.42 (d, J=5.1 Hz, 2H), 6.11(t, J=5.6 Hz,1H), 6.81 (s, 1H), 6.84(s, 1H), 7.11–7.34(m, 12H), 8.47(t, J=5.0 Hz, 1H), 1.55(s, 1H). MS (ESI) M/Z (relative intensity) 587(M+100%), 545(12%), 487(18%), 387(30%) 345(20%).

A solution of 5' (2.5 g, 4.3 mmol) and 1,3-diaminoxylene (590 mg, 4.3 mmol) in 100 mL of THF was heated to reflux for 5 hours. The solvent was evaporated to dryness. Chromatography (CH$_2$Cl$_2$/MeOH 95:5) gave 750 mg of 6 (28% yield).
$^1$H-NMR (CDCl$_3$), 300 mHz)δ 1.46(s,9H) 3.0(dd, J=10.3 Hz, J=17.4 Hz, 1H) 3.47–3.61 (m, 2H), 3.83 (s, 2H), 4.234.42 (m, 7H), 5.27(s broad, 1H) 5.52 (s broad, 1H), 6.90 (d, J=6.1 Hz, 1H), 6.96 (s, 1H), 7.10–7.30 (m, 16H), 8.29 (s, 1H), 11.1 (s, 1H) MS (ESI) M/Z (relative intensity) 649 (M+1, 47%), 366 (100%),345 (48%).
Deblocking: Compound 6' (80 mg) was dissolved in 3 ml of a mixture of TFA/CH$_2$Cl$_2$ (50%). The solution was allowed to stay for 2 hours at room temperature. The solution was evaporated to give 52 mg of 7'.
$^1$H-NMR (DMSO, 300 MHz)δ 2.95(dd, J=5.5 Hz, J=13.5 Hz,1H) 3.37 (dd, J=9.8 Hz, J=22.2 Hz, 1H), 3.88(dd, J=5.7 Hz, J=9.5 Hz, 1H), 4.03(t, J=5.6 Hz, 2H) 4.08(dd J=5.2 Hz, J=15.9 Hz, 1H) 4.28(dd J=6.1 Hz, J=15.8 Hz, 1H), 4.33(d, J=5.5 Hz, 2H), 4.40(d, J=5.5 Hz, 2H), 6.77(d, J=7.0, 2H), 6.98(s, 1H), 7.06–7.41(m, 17 Hz), 8.19(m, 2H), 8.28 (s broad, 2H), 8.55(t, d=5.8 Hz, 1H), 8.69(s broad, 1H), 9.34(s broad, 1H), 10.80(s broad, 1H). MS (ESI)M/Z (relative intensity) 549 (M+1, 50%), 401 (100%) 359 (84%).
By application of the above methodology, the following compounds can also be prepared:
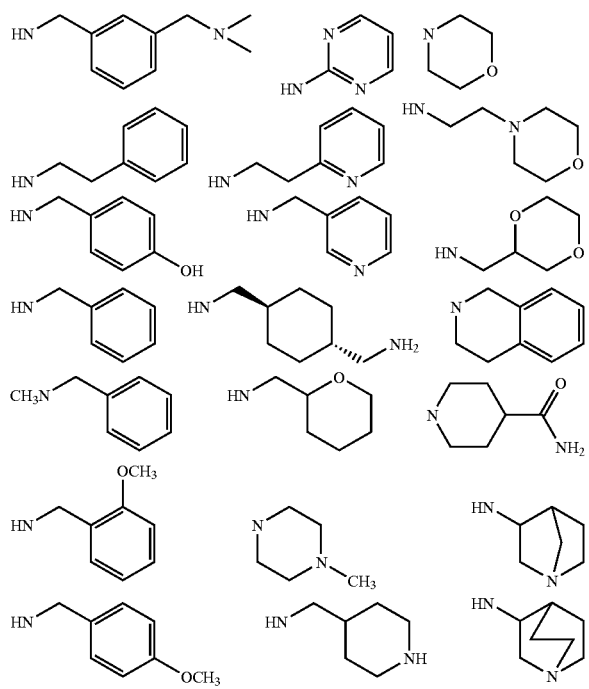
Wherein R =
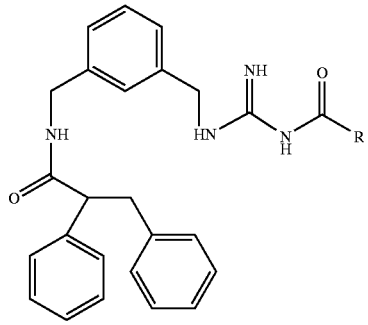
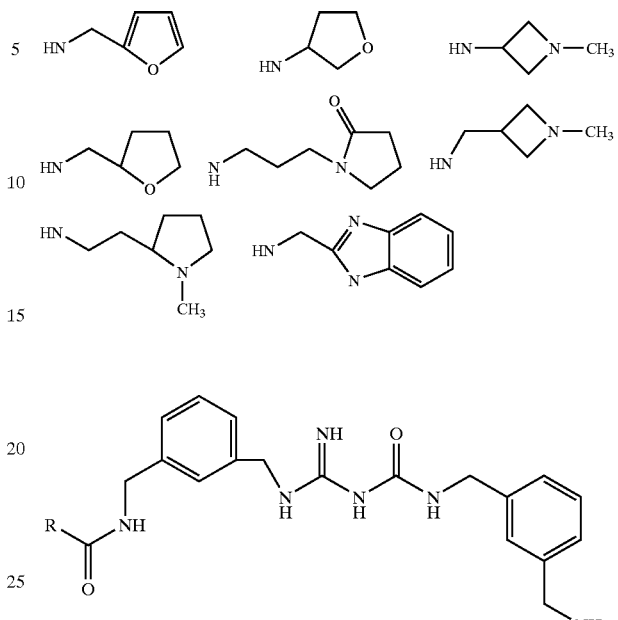
Wherein R =
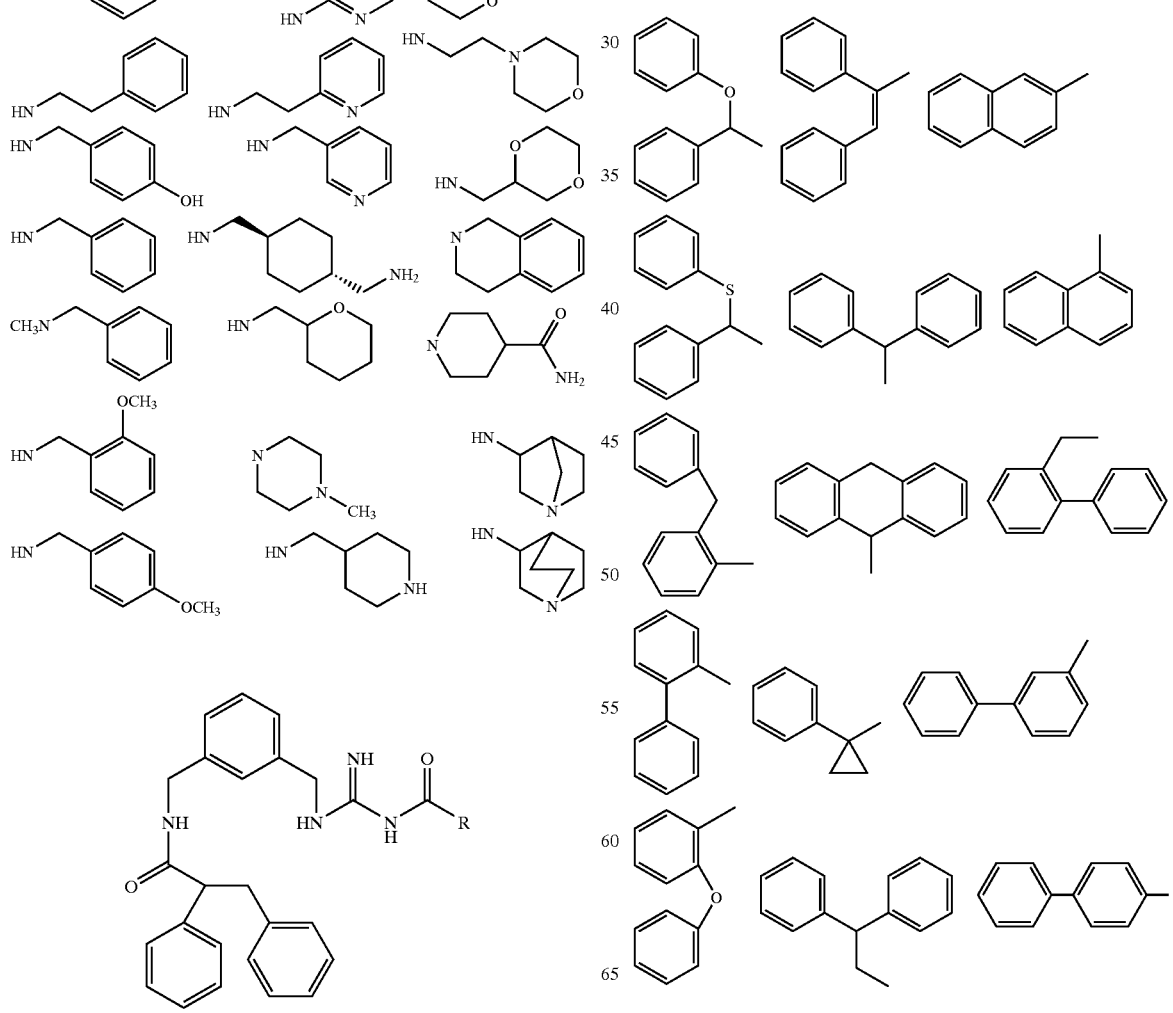

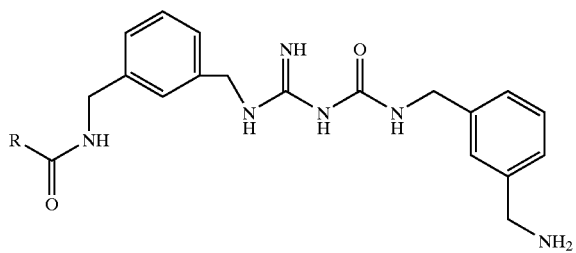

Wherein R =

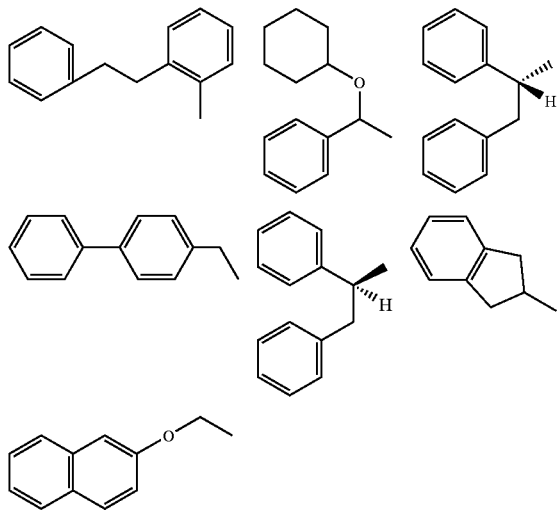

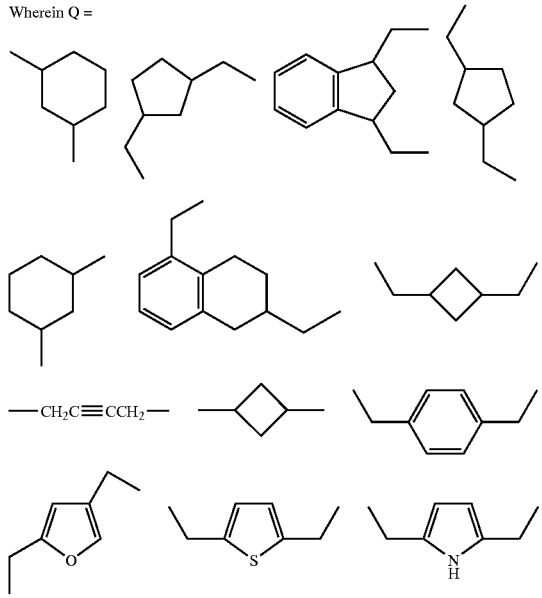

Wherein Q =

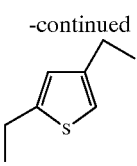

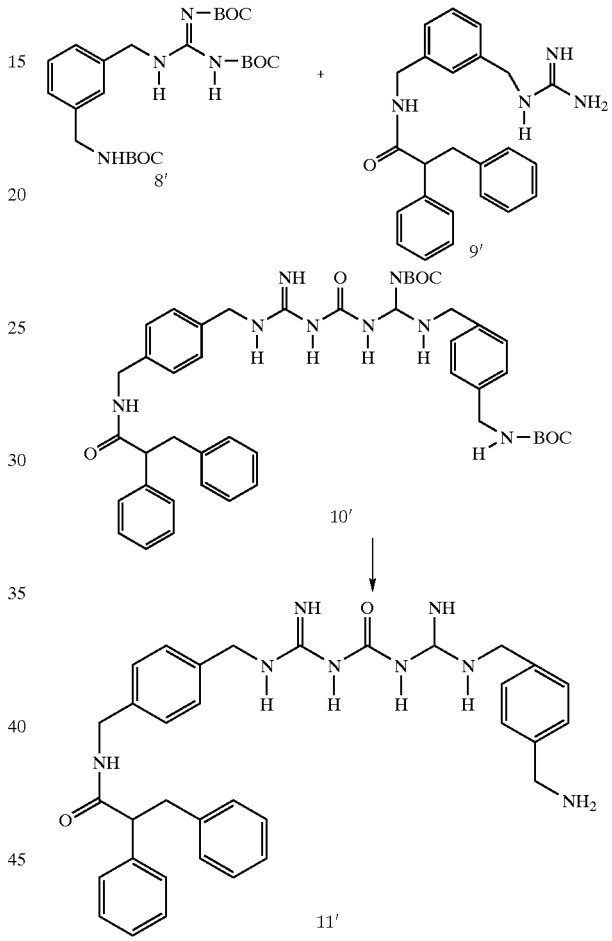

EXAMPLE 2

The synthesis procedure of Example 2 proceeds through the steps of the following Scheme N-[3(1,2-Diphenylpropionylamidomethylphenylethyl-amidino)]—N'-[(3-aminomethylphenylmethyl-amidino] urea (11')

N-(di-Boc-amidino-N'-Boc-1,3-diaminoxylene (8')

To a solution of 3' prepared as in Example 1, (1.6 g, 4.2 mmol) in 15 mL of $CH_2Cl_2$, di-t-butyldicarbonate (1.59 g) was added. The solution was stirred for 20 min at 0° C. The concentrated residue was chromatographed on a silica gel column (hexane/ethyl acetate 5:1) to give 8' (1.9 g, 95%).

$^1$H-NMR (CDCl$_3$, 300 MHz)δ 1.46(s, 9H), 1.48(s, 9H), 1.52(s, 9H), 4.30(d, J=5.7 Hz, 2H), 4.61(d, J=5.2 Hz, 2H), 7.20–7.33(m, 4H) 8.55(s broad, 1H), 11.35(s, 1H).

MS(APC1)M/Z (relative intensity) 479 (M+1, 72%), 437 (17%), 379(34%), 279(100%) 179(9%).

N-Amidino-N'-(2,3 diphenylpropionyl)-amido-1,3-diaminoxylene (9') A solution of 5', prepared as in Example 1 (5.0 g, 8.5 mmol) in 25 mL of TFA/CH$_2$Cl$_2$ (50%) was allowed to stand for 1 hour at room temperature. The reaction mixture was evaporated to dryness. The residue was dissolved in minimum volume of water and 300 mL of THF was added. To this solution potassium hydroxide (KOH) was added until it was saturated. The THF layer was collected and concentrated to leave 9' as a pale yellow solid.

Compound 10:

A mixture of 8' (3.29 g, 8.5 mmol) and 9' (3.29 g, 8.5 mmol) as shown in the above Scheme IV in 100 mL of THF was heated to reflux overnight. The solution was concentrated to dryness. The product (10') was isolated by column chromatography on silica gel (hexane/ethyl acetate 5:1 to 3:1).

$^1$H-NMR (CDCl3), 300 MHz)δ 1.45(s, 9H), 1.48(s, 9H), 2.96(dd, J=6.2 Hz, J=13.5 Hz, 1H), 3.44(dd, J=8.8 Hz, J=13.4 Hz, 1H), 3.68(m, 1H), 4.1(m, 6H), 4.51(s broad, 2H), 5.0(s broad, 1H), 6.70 (s broad, 3H) 7.07–7.28(m, 18H), 11.06(s, 1H).

$^{13}$C-NMR(CDCl$_3$, 300 MHz)δ 27.9, 28.1, 39.6, 43.1, 44.8, 55.4, 60.2, 79.2, 82.9, 126.0, 126.3, 126.7, 126.8, 127.1, 127.8, 128.1, 128.5, 128.7, 128.8, 128.9, 137.4, 138.1, 138.5, 139.5, 139.6, 139.7, 153.0, 153.1, 154.2, 155.9, 163.4, 172.4.

Deblocking: Compound 10' (3.0 g) was dissolved in 20 mL of TFA/CH$_2$Cl$_2$(50%). the solution was allowed to stand for 1 h at room temperature and concentrated by evaporation. 2.6 g of crude mixture was obtained, which was purified by preparative HPLC to give (9).

Analytical HPLC was carried out on a column C$_{18}$ (5 μ4.6×250 mm); UV-absorbance 0.1 aufs @230; Buffer A, 0.1% TFA; Buffer B, 0.1% TFA in 60% CH$_3$CN/40% H$_2$O; flow rate 1.5 ml/min; gradient 0% B to 45'to 100% B. Retention time 35.083 min.

$^1$H-NMR (DMSO, 300 MHz)δ 2.91(dd, J=5.9 Hz, J=13.6 Hz, 1H), 3.35(dd, J=9.4 Hz, J=13.5 Hz, 1H), 3.85(s broad, 2H), 3.87(dd, J=6.0 Hz, J=9.2 Hz, 1H), 4.11(dd, J=5.4 Hz, J=15.3 Hz, 1H), 4.26 (dd, J=6.0 Hz, J=15.6 Hz, 1H), 4.32(dd J=5.7 Hz, 2H) 4.36(d, J=6.1 Hz, 2H), 4.40(d, J=5.7 Hz, 1H), 4.51(d, J=5.8 Hz, 1H), 6.85(d, J=7.3 Hz, 1H), δ 7.13(s, 1H), 7.13–7.40 (m, 16H), 7.98(t, J=5.9 Hz, 1H), 8.05(t, J=5.4 Hz, 1H), 8.39(t, J=5.9 Hz, 1H), 8.60(s broad, 21H) 9.23(d, J=26.3H$_t$, 1H), 10.40(d, J=22Hz, 1H).

$^{13}$C-NMR (CD$_3$OD, 300 MHz)δ 40.4, 43.6, 44.3, 45.9, 55.8, 127.1, 127.2, 127.3, 127.4, 127.5, 127.6, 128.0, 128.2, 128.9, 129.3, 129.5, 130.1, 130.2, 130.4, 136.4, 136.9, 138.0, 140.4, 140.6, 140.9, 141.4, 155.6, 155.9, 156.0, 158.8, 175.5.

MS(ESI) M/Z (relative intensity) 591 (M+1, 21%) 516 (100%), 337(86%).

By application of the above methodology, the following compounds were prepared:

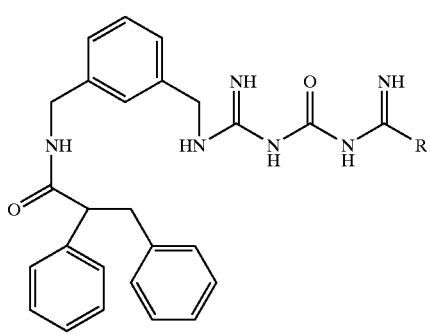

Wherein R =

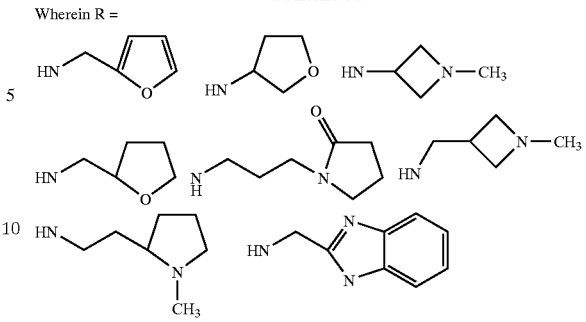

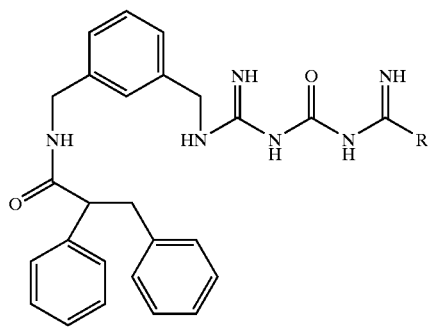

Wherein R =

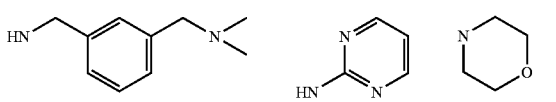

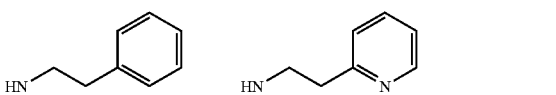

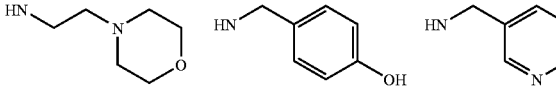

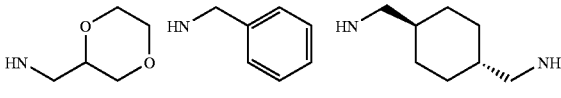

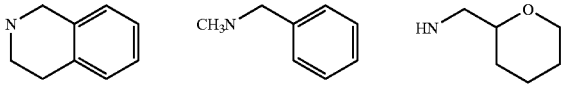

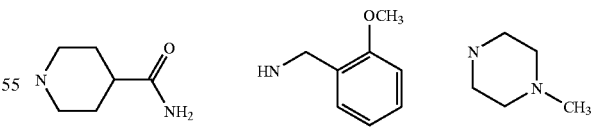

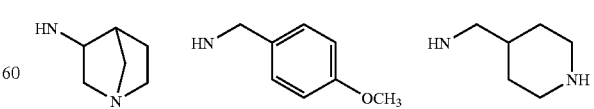

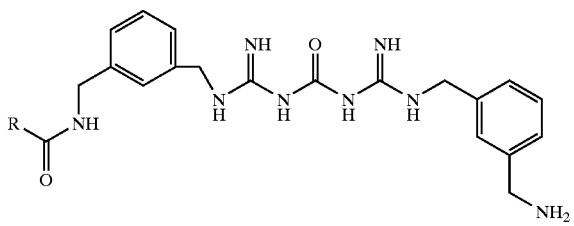

Wherein R =

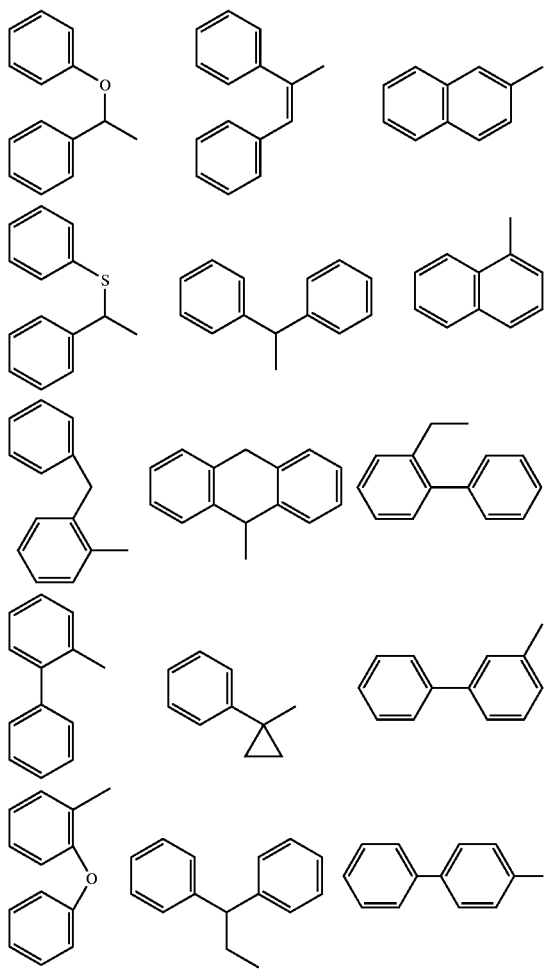

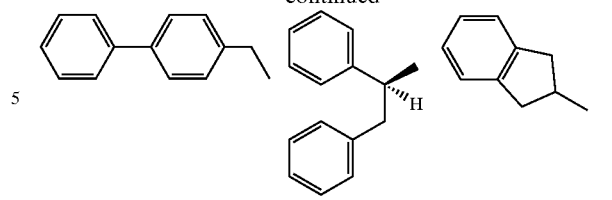

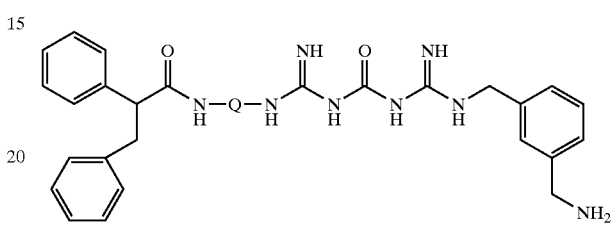

Wherein Q =

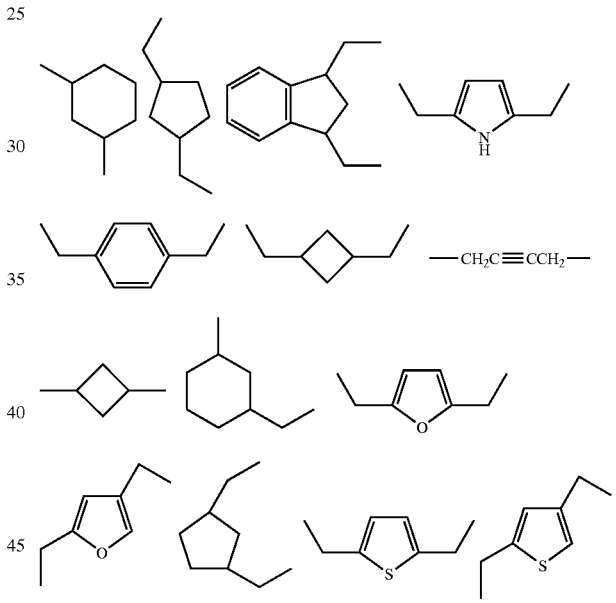

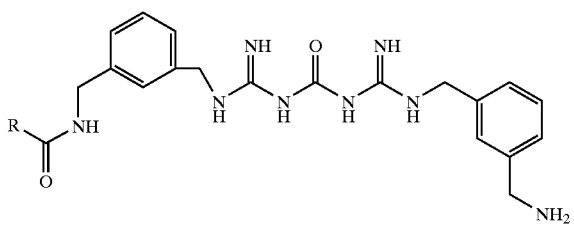

Wherein R =

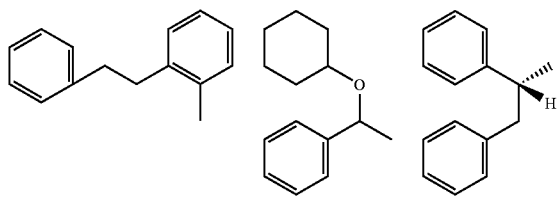

EXAMPLE 3

Method A for the preparation of $R^{2'}$—$NH_2$ precursors with general formula 2 (scheme I), according to Scheme II.

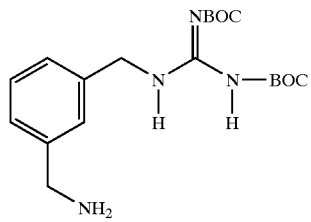

N-(N-BOC-amino-N-BOC-imino)-1,3-bis-aminomethyl-benzene

To a solution of 30.1 g (221 nmol) of 1,3-bis-(aminomethyl)benzene in 500 ml of dry tetrahydrofuran was added 34.3 g (110.5 mmol) of 1-(N,N-di-BOC-amidino)-pyrazole ((Bernatowitz, M. S. et al. (1992) J. Org. Chem 57:2497). The mixture was stirred for 2 hours at room temperature.

The solvent was removed by evaporation in vacuum at under 40° C., and the resulting oily residue was purified by chromatography on a silica gel column, using a gradient of 25 to 50% ethyl acetate in hexane to give after concentration in vacuo 41.8 g of the desired material as a yellow oil.

By application of the above methodology, the following compounds were also prepared:

N-(N-BOC-amino-N-BOC-imino)-1,4-bis-aminomethyl-benzene

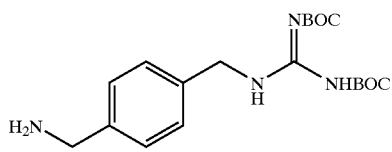

N-(N-BOC-amino-N-BOC-imino)-1,4-diaminobutane

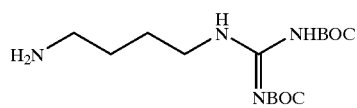

N-(N-BOC-amino-N-BOC-imino)1,5-diaminopentane

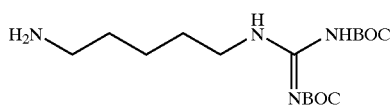

N-(N-BOC-amino-N-BOC-imino)-1,5 diaminohexane

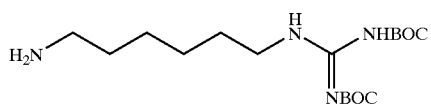

N-(N-BOC-amino-N-BOC-imino)-trans-1,3-bis-amino methyl cyclohexane

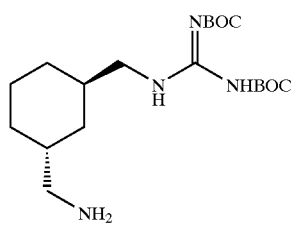

N-(N-BOC-amino-N-BOC-imino)cis-1,3-bis-aminomethyl cyclohexane

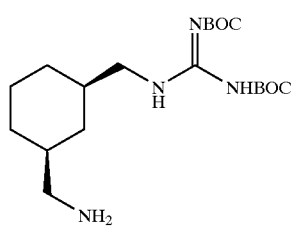

N-(N-BOC-amino-N-BOC-imino)-2,4-bis-aminomethyl-thiophene

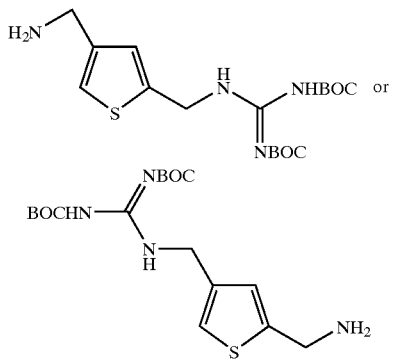

N-(N-BOC-amino-N-BOC-imino)-2,5-bis aminomethylthiophene

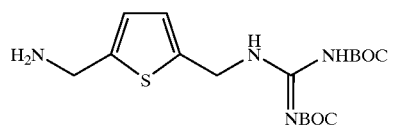

N-(N-BOC-amino-N-BOC-imino)-2,4-bis-aminomethyl-furan

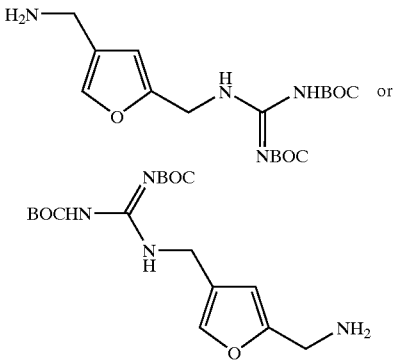

N-(N-BOC-amino-N-BOC-imino)-2,5-bis-aminomethyl-furan

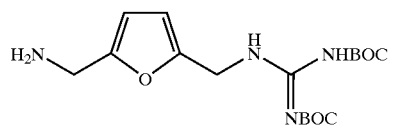

EXAMPLE 4

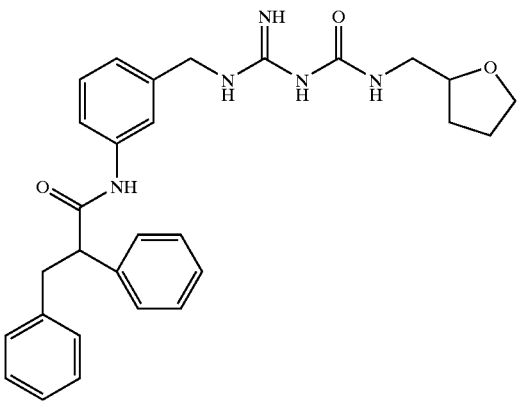

Synthetic Scheme:

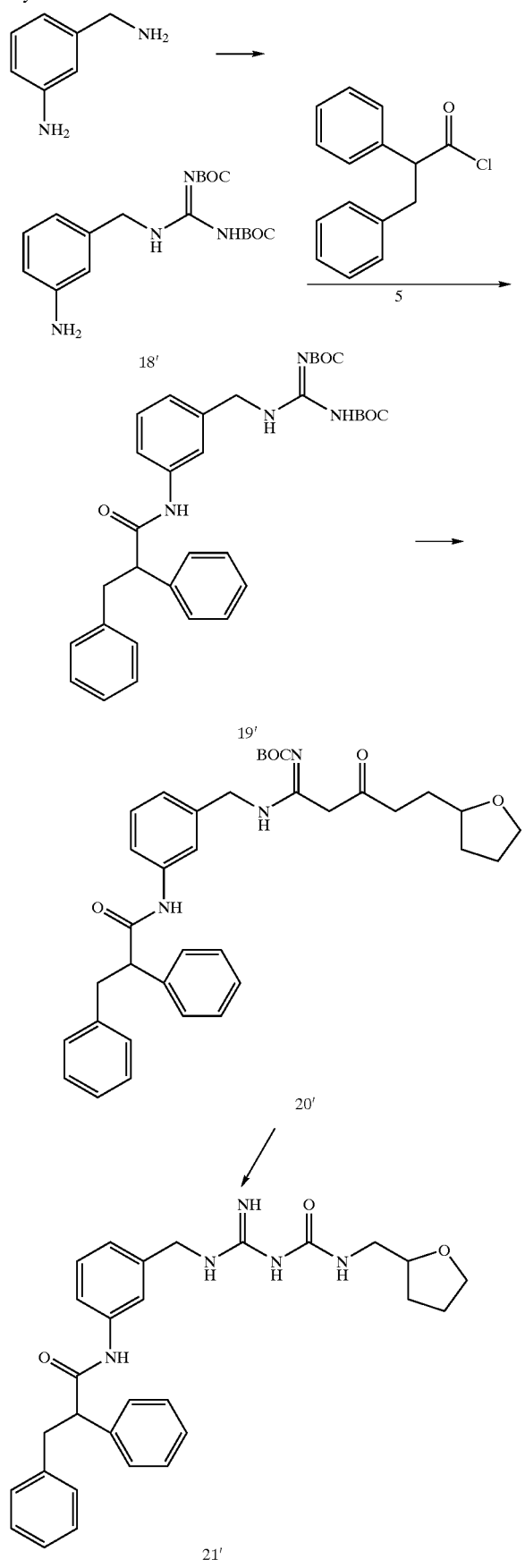

Synthesis of Compound 18'
  Same procedure as described for the synthesis of compound 3.
Synthesis of Compound 19'
  Same procedure as described for the synthesis of compound 5.
Synthesis of Compound 20'
  Same procedure as described for the synthesis of compound 6, except tetahydrofurfurylamine was used.
Synthesis of Compound 21'
  Same procedure as described for the synthesis of compound 7.
$^1$H NMR (DMSO-D$_6$)δ1.48 (m,1H), 1.82 (m,3H), 2.9 (dd, 1H), 3.14 (m, 3H), 3.50 (m, 1H), 3.61 (m, 2H), 3.74 (m, 1H), 4.00 (m, 1H), 4.45 (m, 1H), 6.94 (m, 1H), 7.22 (m, 9H), 7.33 (m,3H), 7.5 (s, 1H), 7.80 (brd s, 1H), 8.60 (brd s, 2H), 9.34 (brd s, 1H), 10.23 (brd, 2H).
By application of the above methodology the following compounds are prepared.

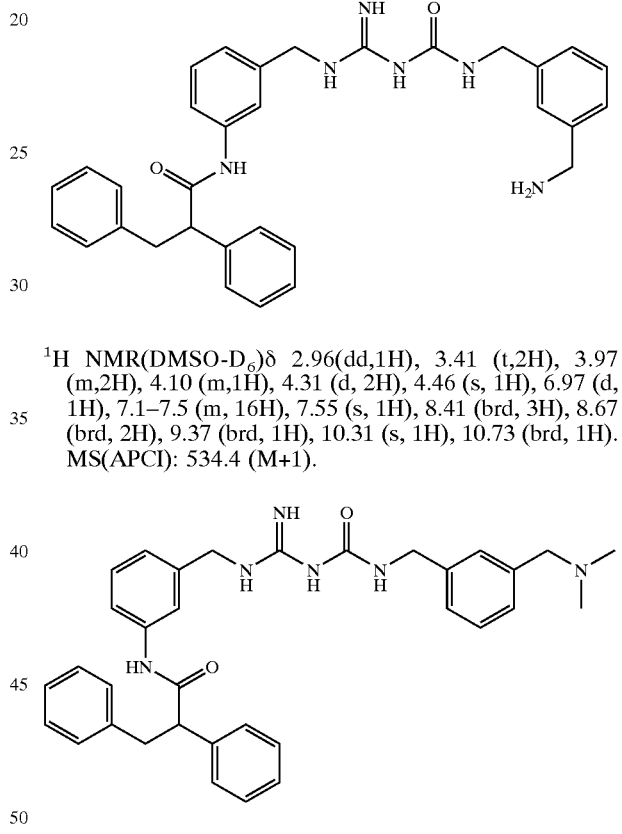

$^1$H NMR(DMSO-D$_6$)δ 2.96(dd,1H), 3.41 (t,2H), 3.97 (m,2H), 4.10 (m,1H), 4.31 (d, 2H), 4.46 (s, 1H), 6.97 (d, 1H), 7.1–7.5 (m, 16H), 7.55 (s, 1H), 8.41 (brd, 3H), 8.67 (brd, 2H), 9.37 (brd, 1H), 10.31 (s, 1H), 10.73 (brd, 1H). MS(APCI): 534.4 (M+1).

EXAMPLE 5

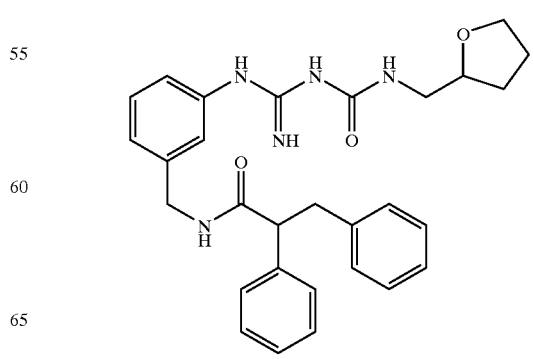

Synthetic Scheme:

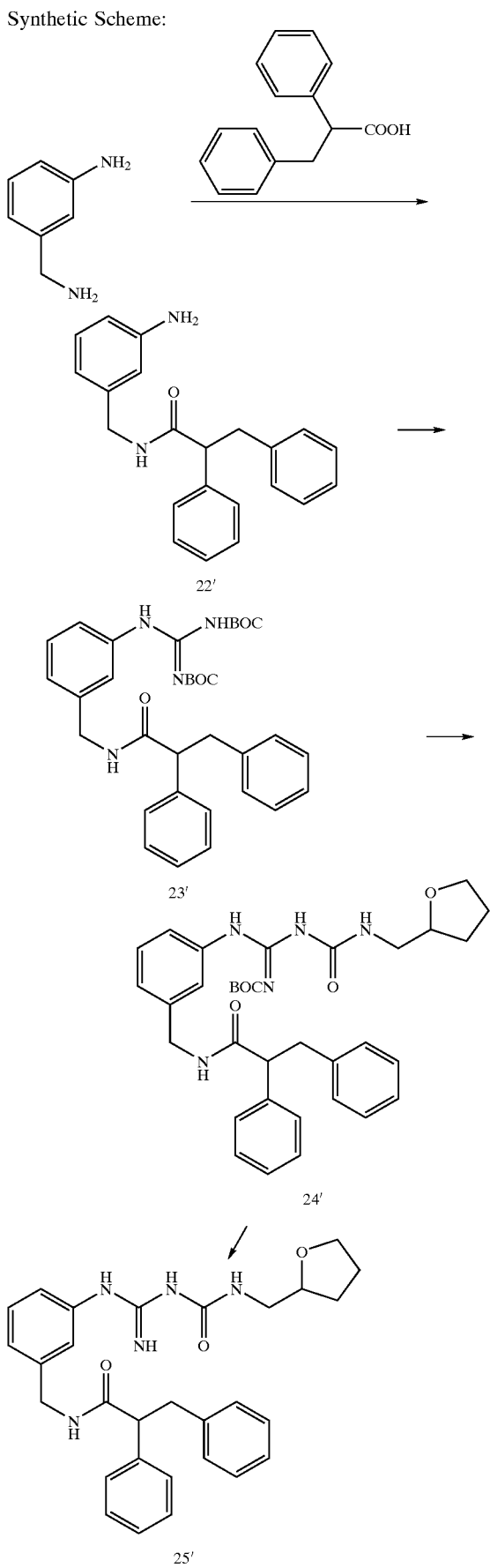

Synthesis of Compound 22'

To a solution of diphenylpropanoic acid (3.0 g, 13.3 mmol) in 20 mL of $CH_2Cl_2$ was added 2.7 g (13.3 mmol) of 1,3 dicyclohexylcarbodiimide (DCC). After being stirred for 5 minutes, 1.6 g (13.3 mmol) of 3-aminobenzylamine was added. The solution was stirred at room temperature for 2 hours. The dicyclohexylurea was removed by filtration. The filtrate was concentrated. The residue was chromatographed on silica gel, eluting with 3:1 hexane:ethyl acetate, to afford 1.9 g of N-(1,2-diphenylcarbonyl)-3-aminobenzylamide.

$^1$H NMR ($CDCl_3$)δ 2.98 (dd,1H), 3.66 (m, 2H), 4.08 (m, 1H), 4.31 (dd,1H), 5.90 (t, 1H), 6.12 (s, 1H),6.33 (d, 1H), 6.48 (d, 1H), 6.96 (t, 1H), 7.09–7.34 (m, 10H). MS (APCI): 331 (M+1)

Synthesis of Compound 23'

A solution of 190 mg (0.61 mmol) of N,N'-bis(tert-butoxycarbonyl)-1H-pyrazole-1-carbox-amidine and 200 mg (0.61 mmol) of compound 22 in toluene was heated at reflux for 5 hours. The concentrated residue was chromatographed on silica gel, eluting with 1:4 hexane:ethyl acetate to afford 67 mg of 3-[N,N'-bis(tert-butoxycarbonyl) carboxamidino]—N"-(2,3-diphenylpropanoyl)benzyl amide.

Synthesis of Compound 24'

Same procedure as described for the synthesis of compound 6, except tetrahydrofurfuryl amine was used.

$^1$H NMR ($CDCl_3$)δ1.52–1.85 (m, 4H), 1.96 (s, 9H), 2.92 (dd, 1H), 3.10 (m, 1H), 3.4 (m, 1H), 3.51–3.73 (m, 4H), 3.82 (dd, 1H), 3.90 (dd, 1H), 5.90 (s, 1H), 6.25 (s, 1H), 6.62 (d, 1H), 7.10–7.35 (m, 13H), 7.42 (d, 1H), 10.05 (s, 1H).

Synthesis of Compound 25'

Same procedure as described for the synthesis of compound 7.

$^1$NMR (DMSO-$D_6$)δ1.52 (m, 1H), 1.84 (m, 3H), 2.90 (dd, 1H), 3.16 (m, 1H),3.30 (m, 2H),3.64 (qt, 1H), 3.76 (qt. 1H), 3.90 (m, 2H),4.10 (dd, 1H), 4.31 (dd, 1H), 6.81 (s, 1H), 6.87 (d, 1H), 7.10–7.30 (m, 10H), 7.42 (d, 2H), 7.99 (t, 1H),8.42 (brd, 1H), 8.61 (t, 1H), 8.97 (brd, 1H), 10.14 (brd, 1H), 10.79 (brd,1H). MS (ESI): 499.47 (M+1).

EXAMPLE 6

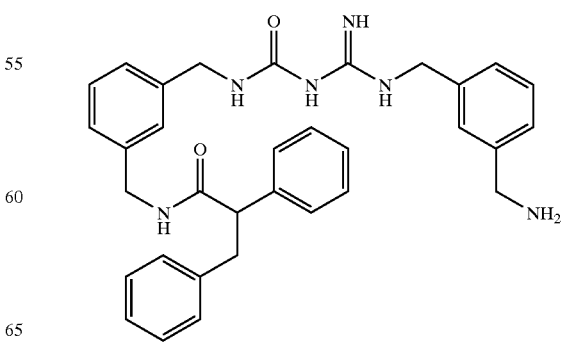

Synthetic Scheme:

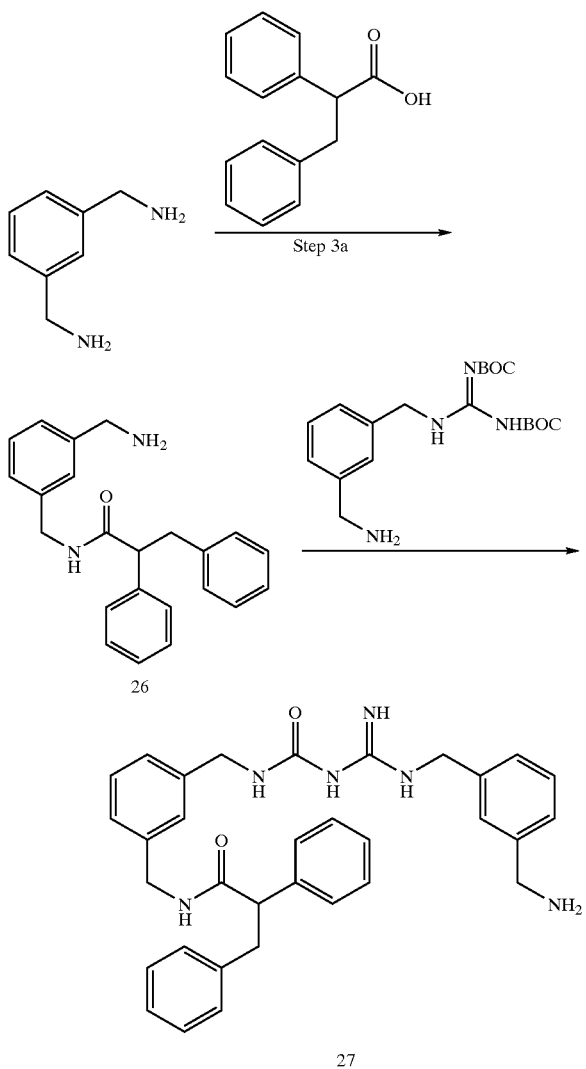

Synthesis of Compound 26
Same procedure as described for the synthesis of compound 22.

Synthesis of Compound 27
A solution of 1.0 g (3.0 mmol) of N-(1,2-diphenylpropanoyl)-1,3 diaminoxylene and 1.1 g (3.0 mmol) of N-(di-boc-amidino)-1,3-diaminoxylene in 20 mL of THF was heated at reflux for 15 hours. The solution was concentrated. To the residue was added 5 mL of 50% TFA in CH$_2$Cl$_2$. The solution was stirred at room temperature for 1 hour. The solution was concentrated to afford 380 mg of N-[3(1,2-diphenylpropanoylamidomethyl-phenyl-methyl)]—N'(3-aminomethyl-phenylmethyl-amidino)urea.
$^1$HNMR (DMSO-d$_6$)δ 2.92 (dd, 1H), 3.36 (dd,1H), 3.86 (d,2H), 3.95 (d, 2H), 4.08 (dd, 1H), 4.29 (dd, 1H), 5.08 (brd, 4H), 6.84 (d,1H), 7.10 (s, 1H), 7.20 (m, 6H), 7.32 (m, 3H), 7.43 (m, 3H), 8.56 (m,4H).

Synthesis of Compound 28
A solution of 20.0 g (86 mmol) of meso-2,3-diphenylsuccinonitrile in 350 mL (345 mmol) of BH$_3$-THF (1.0M in THF) was heated at reflux for 18 hours. The solution was cooled to 0° C., To this solution was added dropwise 100 mL of 3N HCl and stirred for 20 minutes. The solution was reflux for 2 hours and stirred at room temperature for 3 hours. The resulting white precipitate, (19.0 g) was collected by filtration and dried.
$^1$H NMR (DMSO-d$_6$)δ2.7 (brd, 2H), 2.8 (m$_{brd}$, 4H), 7.5 (m, 10H), 7.9 (brd, 4H). MS(APCI): 240 (M+1).

Synthesis of Compound 29
Same procedure as described for the synthesis of compound 3.
$^1$H NMR (CDCl$_3$)δ 1.3 (s, 18H), 1.4 (s, 18H), 3.2 (m, 2H), 3.3 (m, 2H), 3.5 (m, 2H), 7.2 (m, 2H), 7.3 (m, 8H), 7.9, (t, 2H). MS(APCI): 724 (M+1).

Synthesis of Compound 30
Same procedure as described for the synthesis of compound 6, except 5-hydroxypentylamine was used.
$^1$H NMR (CDCl$_3$)δ 1.40 (s, 9H), 1.45 (s, 9H), 1.50 (s, 9H), 1.60 (m, 6H), 3.15 (m, 5H), 3.35 (m, 1H), 3.50 (m, 2H), 3.65 (t, 2H), 4.95 (t, 1H), 7.3 (m, 10H), 7.65 (t, 1H), 7.90 (t, 1H).

Synthesis of Compound 31
Same procedure as described for the synthesis of compound 7.
$^1$H NMR (DMSO-d$_6$)δ 1.1 (m, 2H), 1.2 (m, 4H), 2.8 (brd, 4H), 3.2 (m, 4H), 3.8 (brd, 6H), 7.2 (m, 10H), 7.3 (s, 1H), 7.4 (s, 1H), 8.2 (brd, 2H), 8.7 (brd, 1H), 10.0 (brd, 1H).

By use of the methodology shown in Examples 1–6, the following compounds are

53
-continued
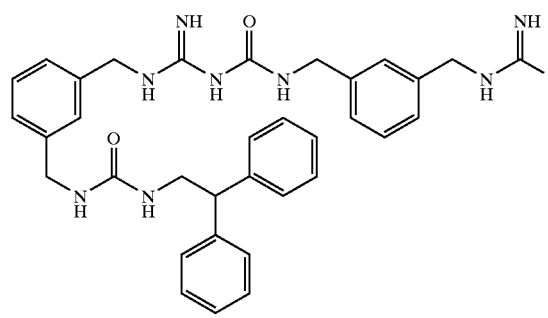
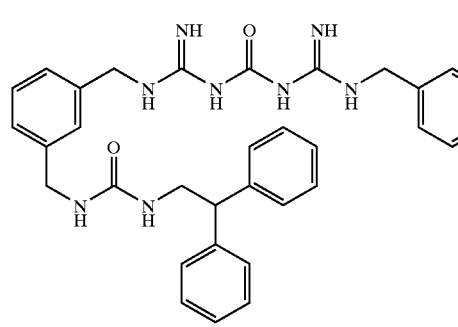
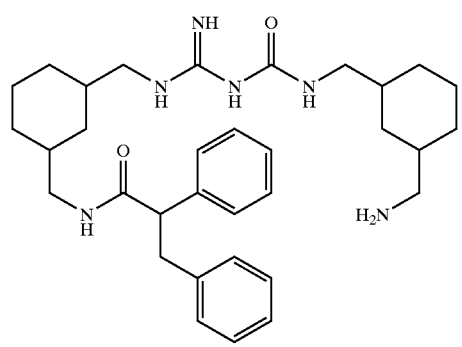
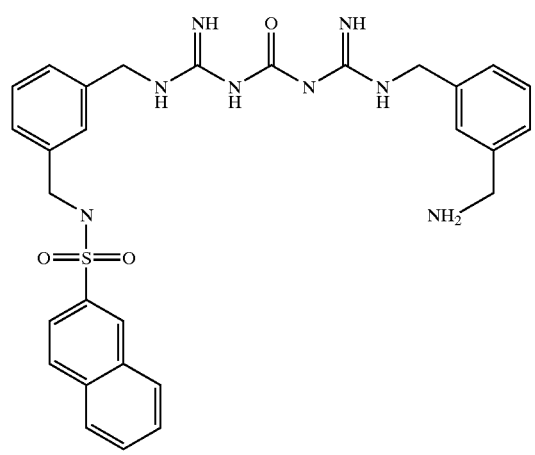
54
-continued
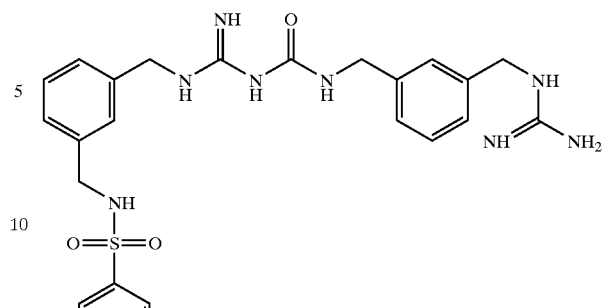
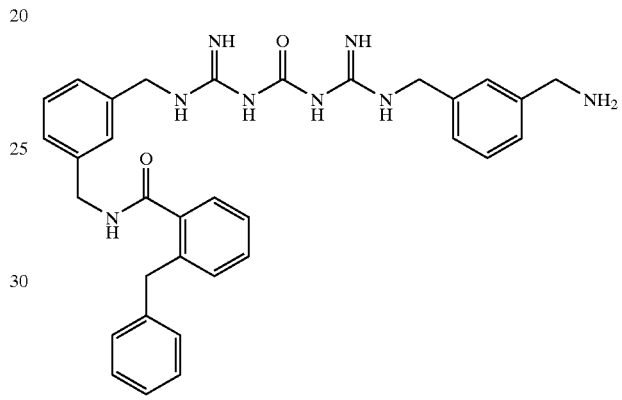
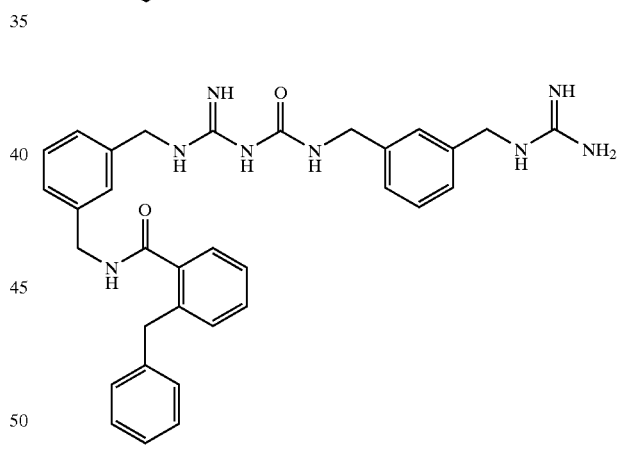
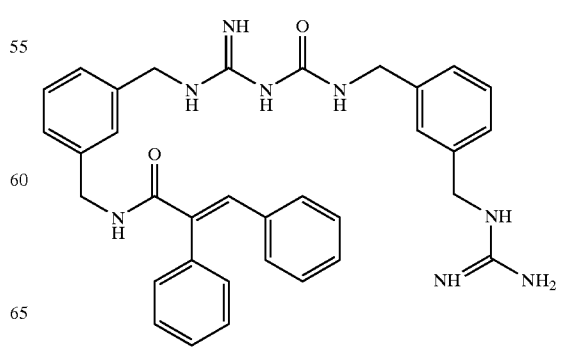

55
-continued
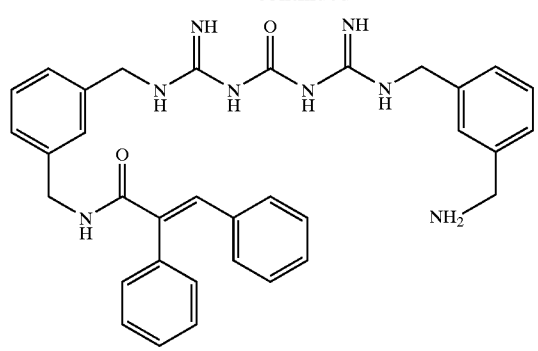
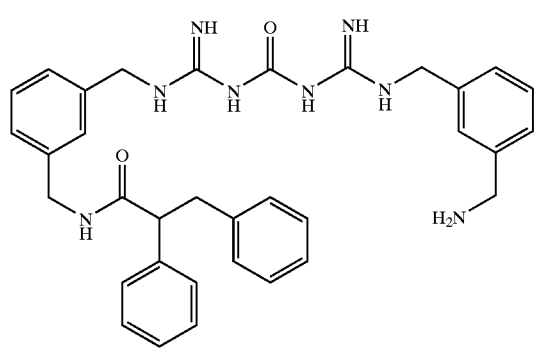
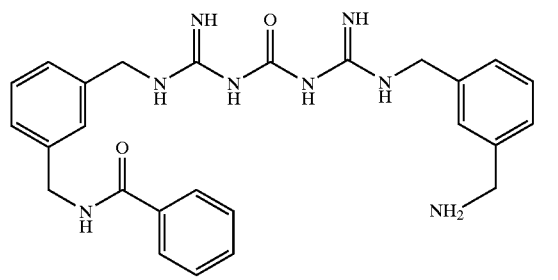
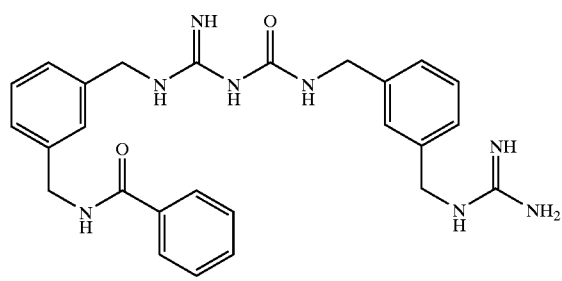
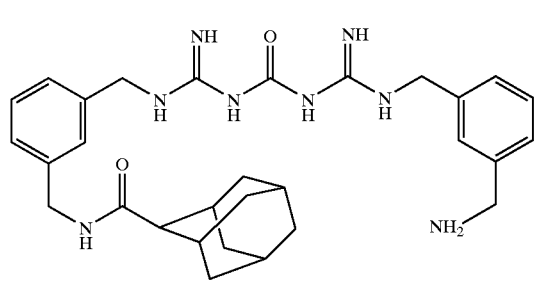
56
-continued
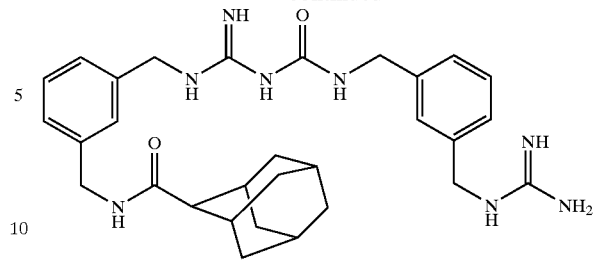
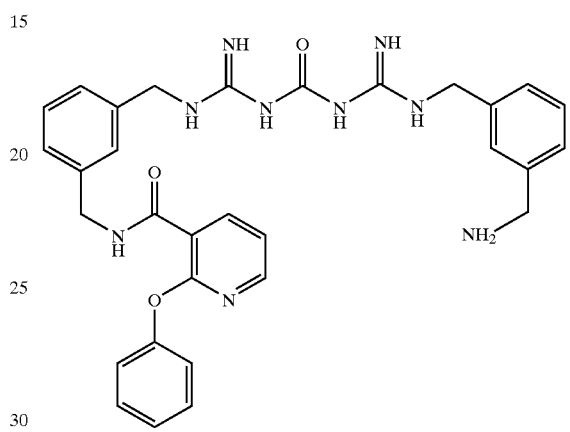
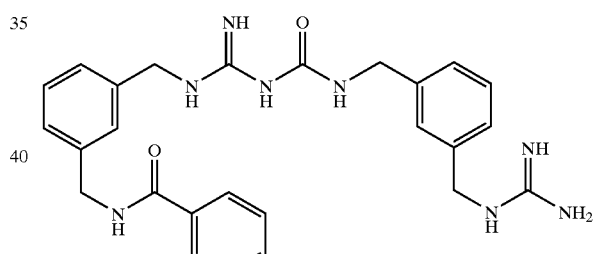
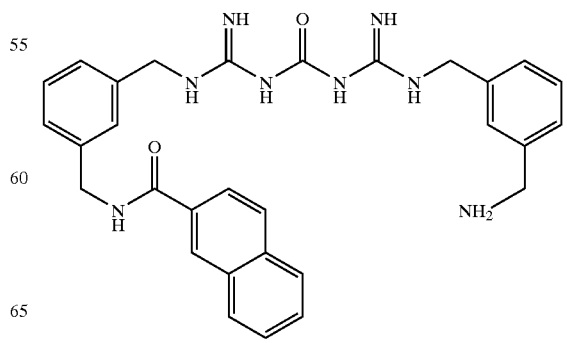

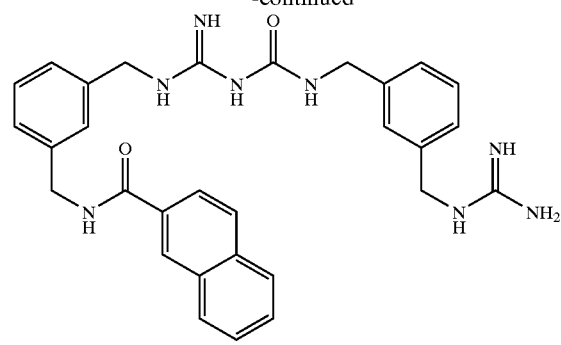
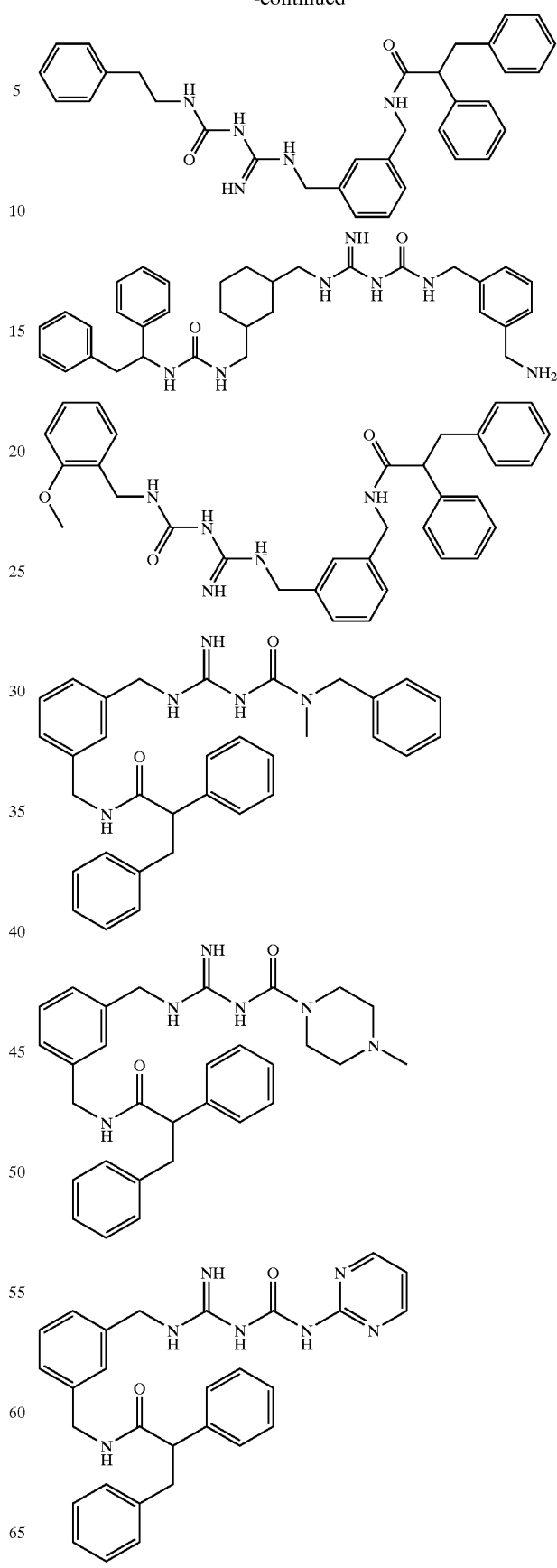

59
-continued
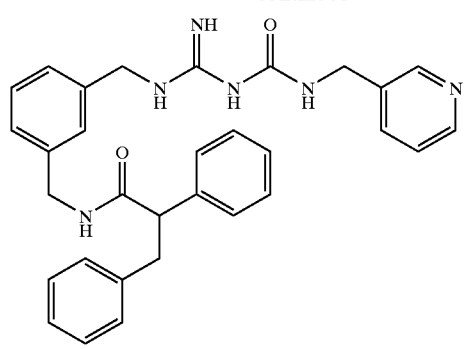
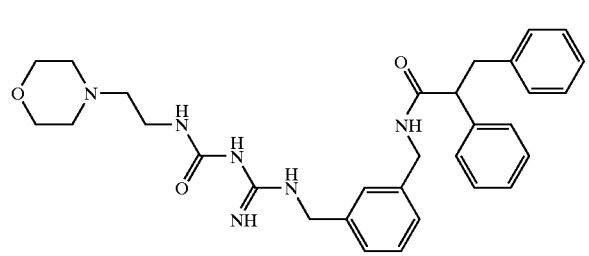
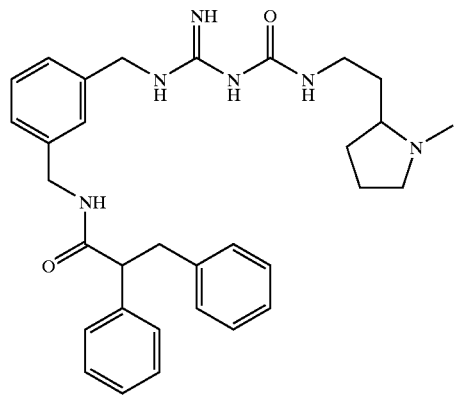
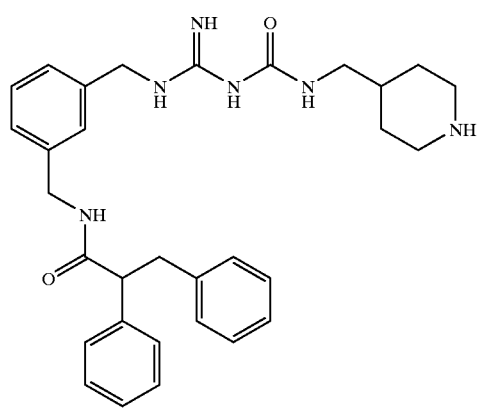
60
-continued
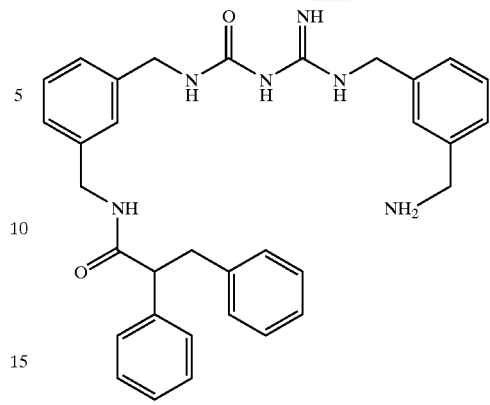
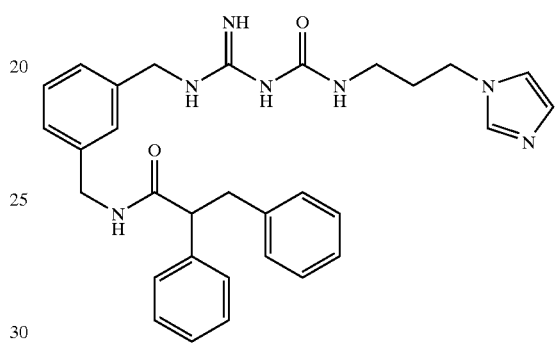
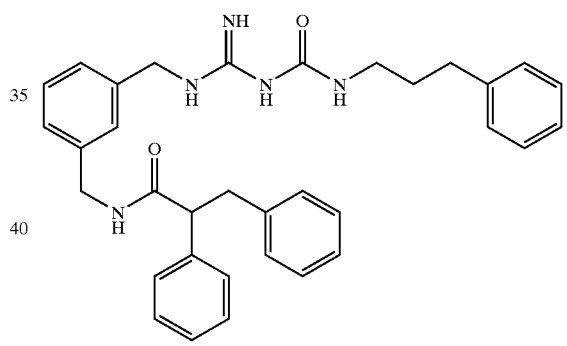
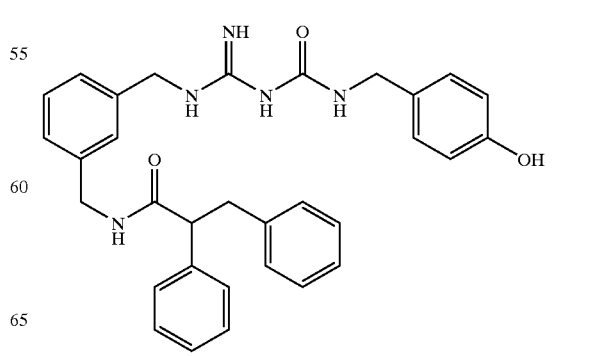

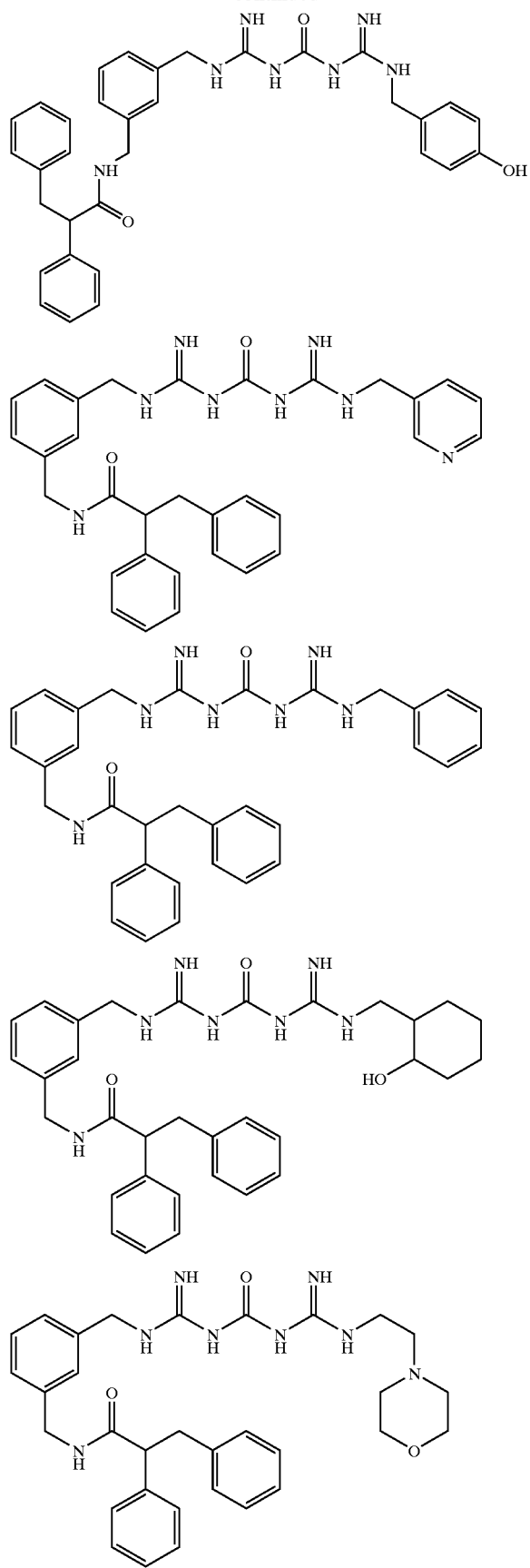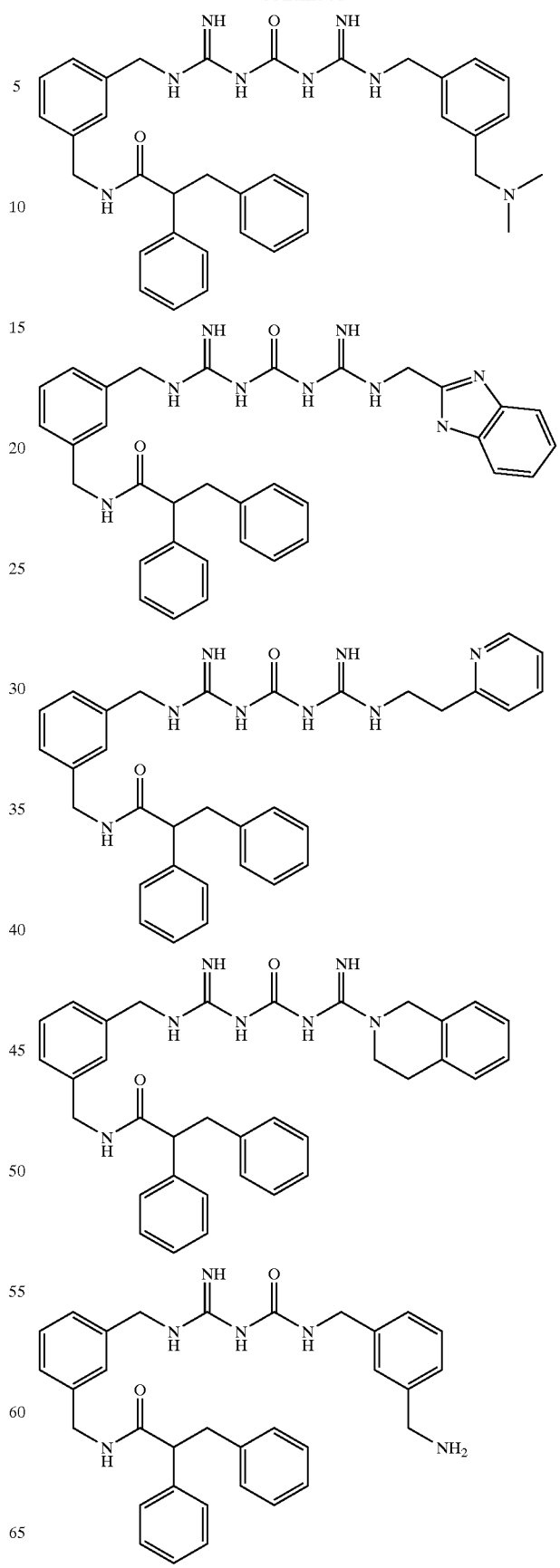

63
-continued
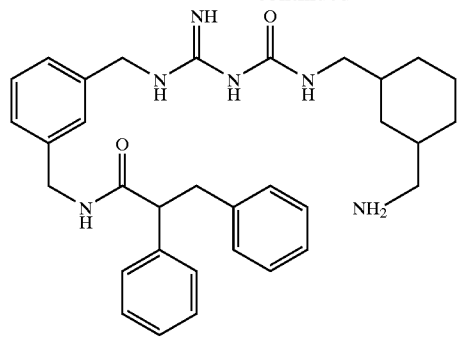
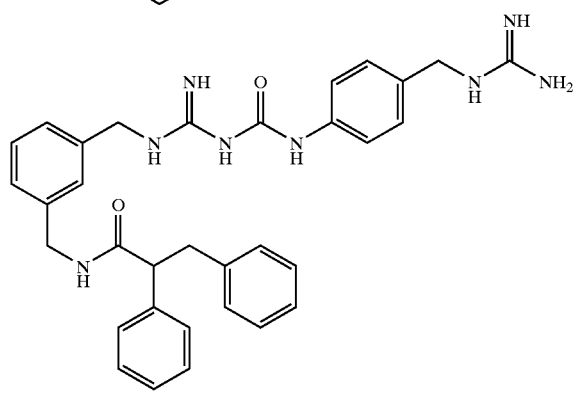
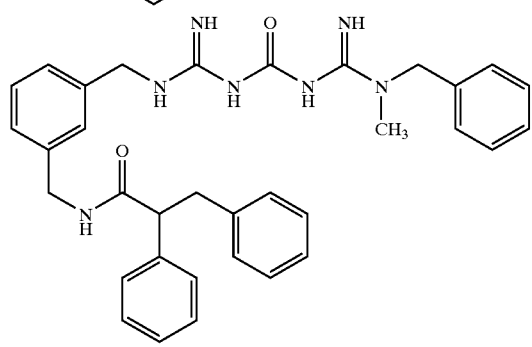
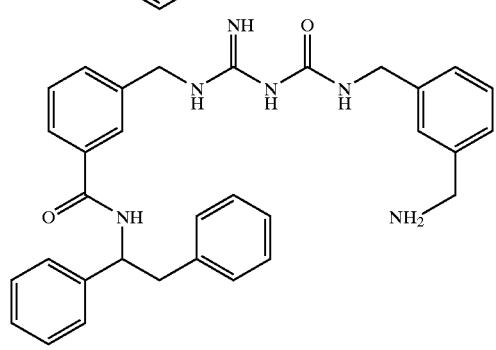
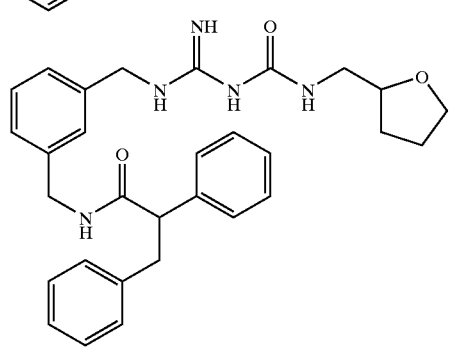
64
-continued
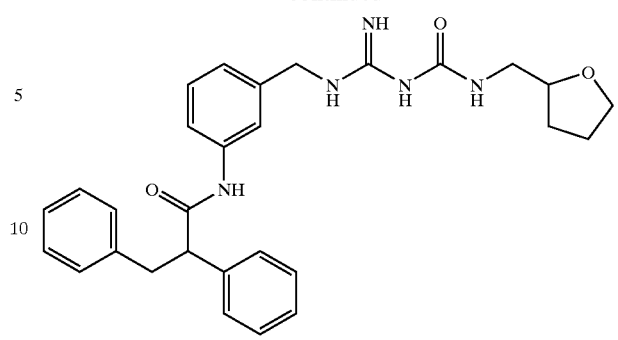
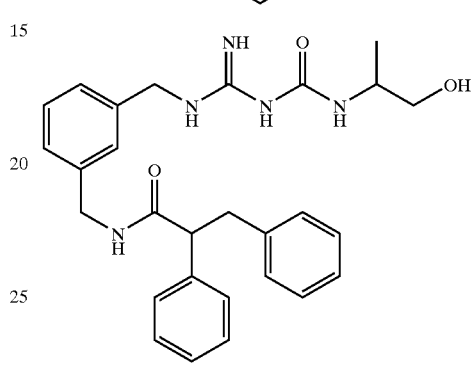
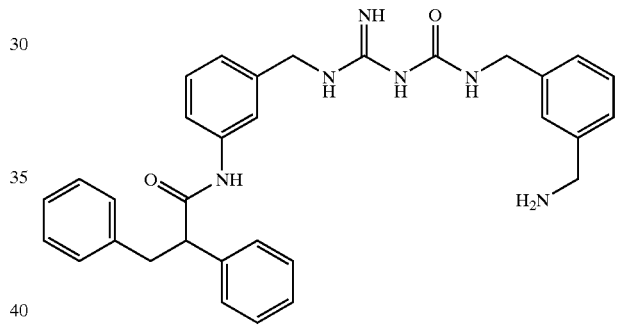
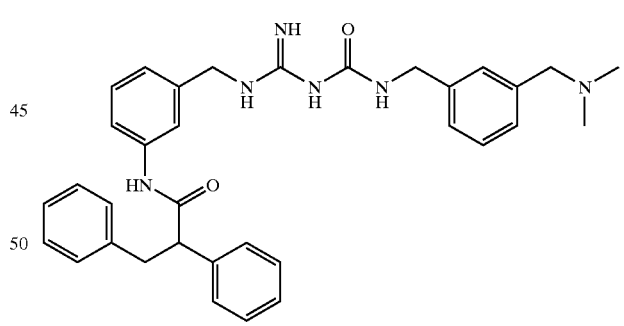
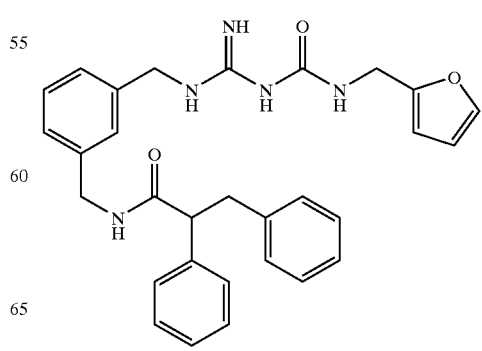

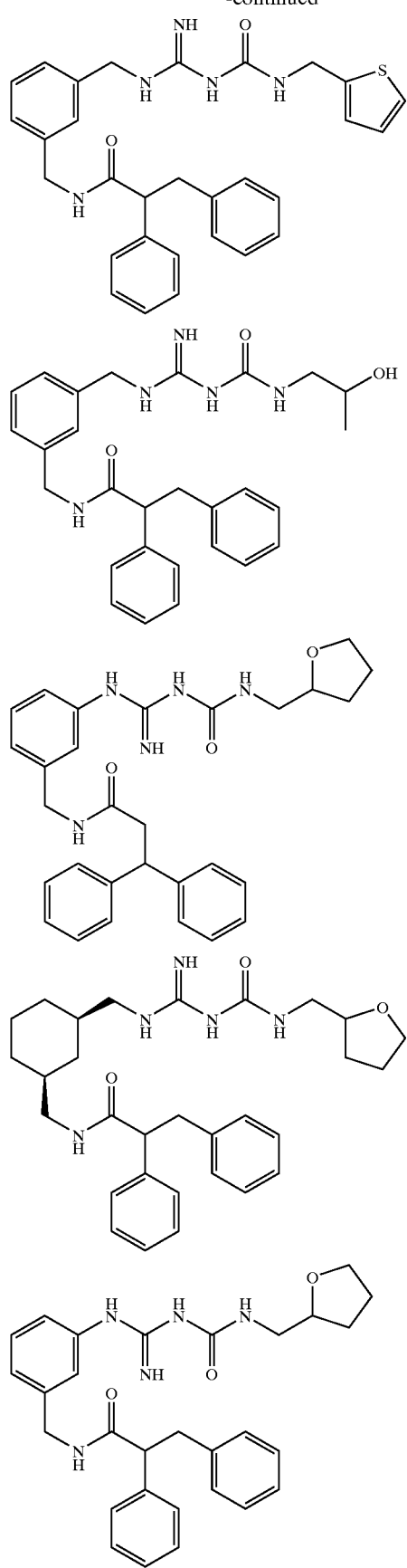
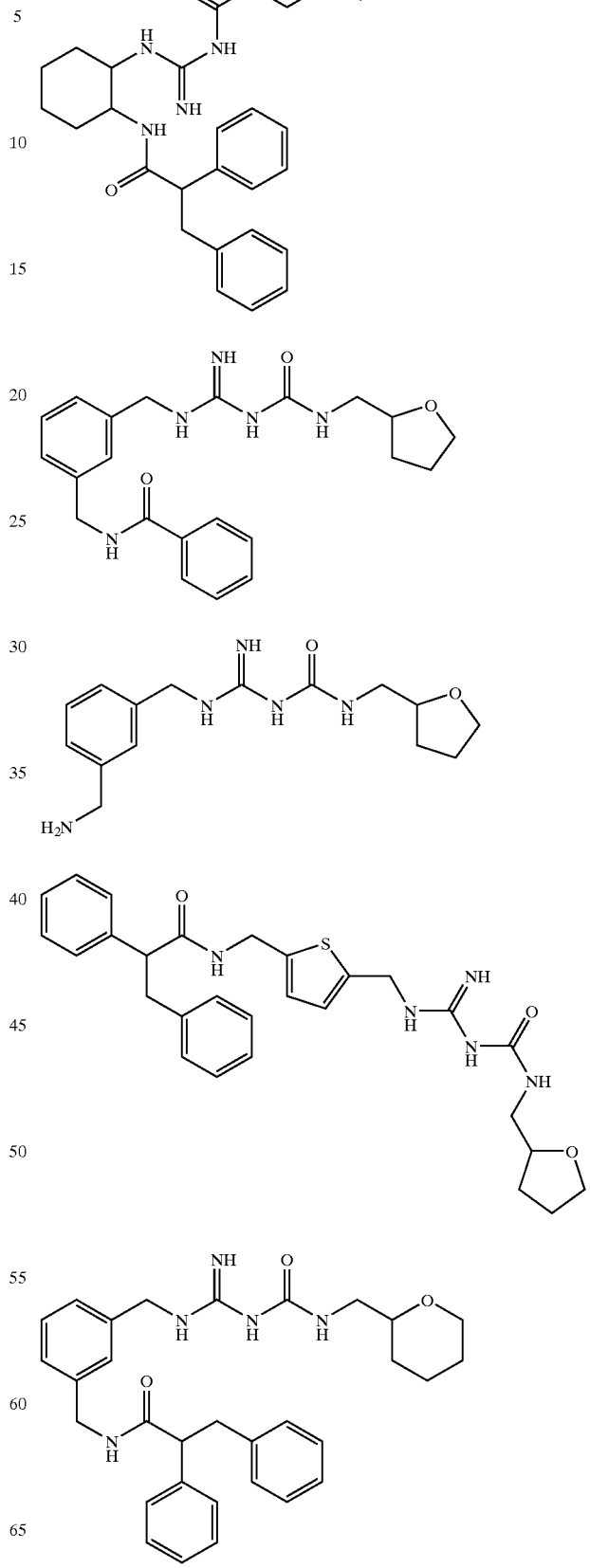

67
-continued
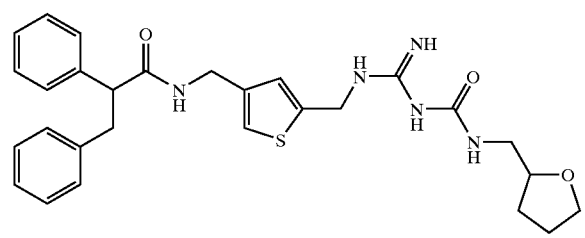
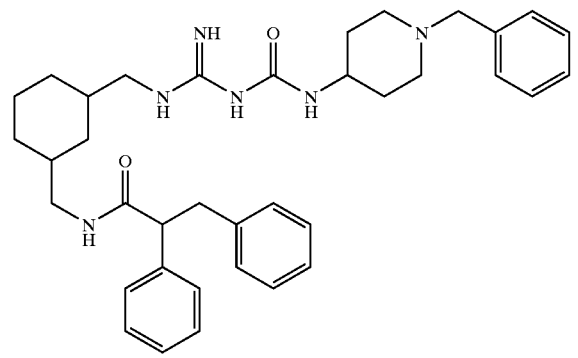
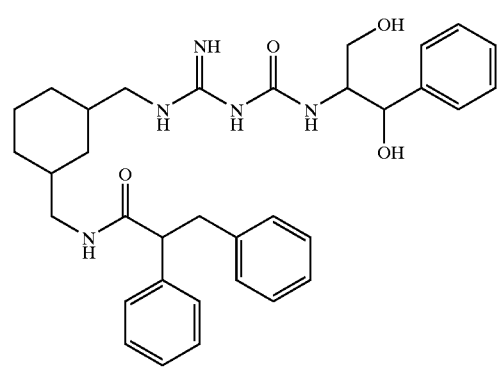
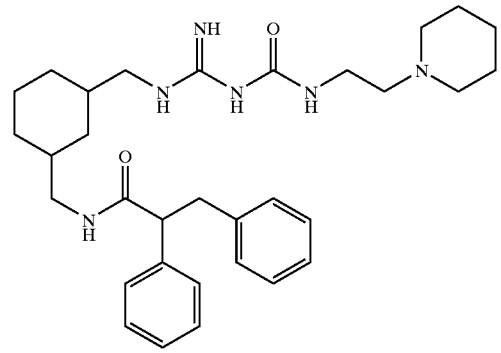
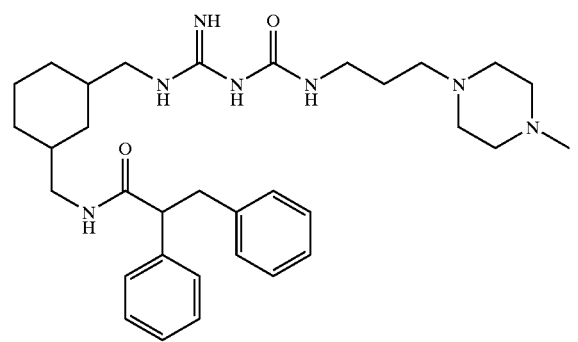
68
-continued
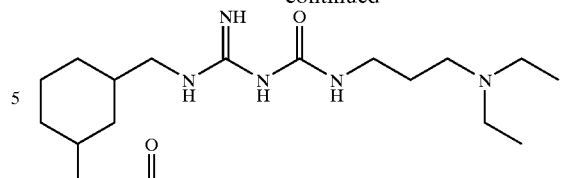
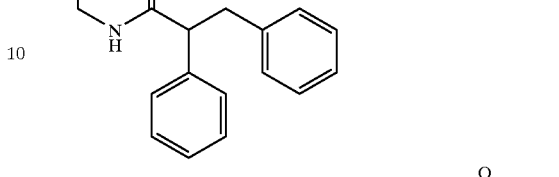
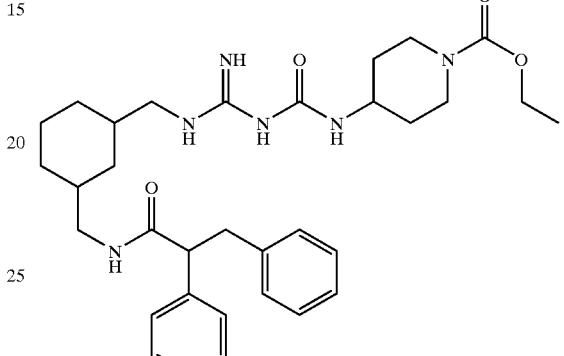
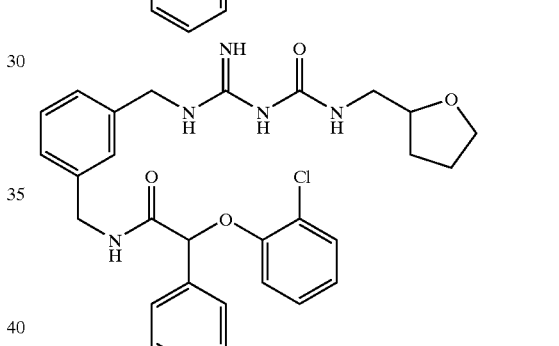
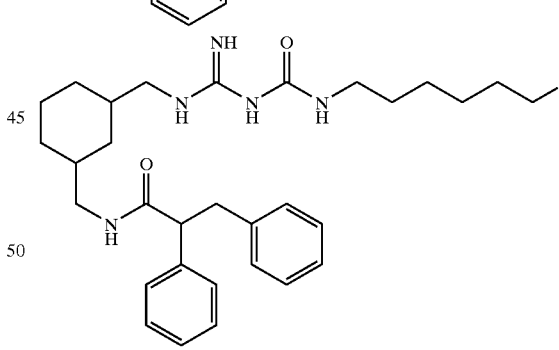
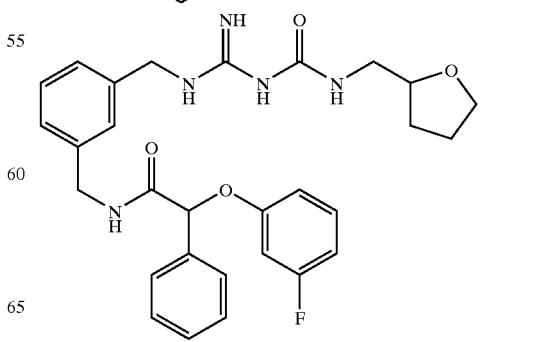

EXAMPLE 7

Radioligand Binding Assay

The activity of the compounds at NPY receptors was assessed by determining their ability to inhibit the binding of $^{125}$I-labeled Peptide YY ($^{125}$I-PYY) to NPY receptors in membranes derived from clonal cell lines. PYY was radio-iodinated using Chloramine T and the product was purified by reverse phase HPLC. The source of the membranes was the human neuroblastoma cell line SK-N-MC. Briefly, SK-N-MC cells were harvested with an EDTA-containing saline solution, resuspended in a hypotonic buffer and homogenized with a Polytron tissue disrupter, the homogenate was centrifuged at 1000×g for 10 minutes at 4° C. The resulting supernatant was centrifuged at 48000×g for 20 min at 4° C. The membranes were washed by centrifugation and resuspension, and the final pellet stored at −70° until use. The binding of $^{125}$I-PYY (30–50 pM)±test compounds to thawed membranes was performed in a buffer consisting of 25 mM HEPES pH 7.4, 2 nmM MgCl$_2$, 2.5 mM CaCl$_2$, 5 mM KCl, 135 mM NaCl, and 0.1% bovine serum albumin (BSA) and 100 μg/ml bacitracin. The assays were incubated for 90 min at 37°, and were terminated by rapid filtration over glass fiber filters that had been pre-soaked with 0.1% polyethylenimine. $^{125}$I-PYY binding was quantitated with either a Packard TopCount scintillation or Packard Cobra gamma counter. Dose-response data were analyzed by non-linear regression using the computer program Prism (GraphPad Software, San Diego, Calif.). IC$_{50}$ values representing the concentration of drug that produced a 50% displacement of the binding of $^{125}$I-PYY are given.

Biological Activity

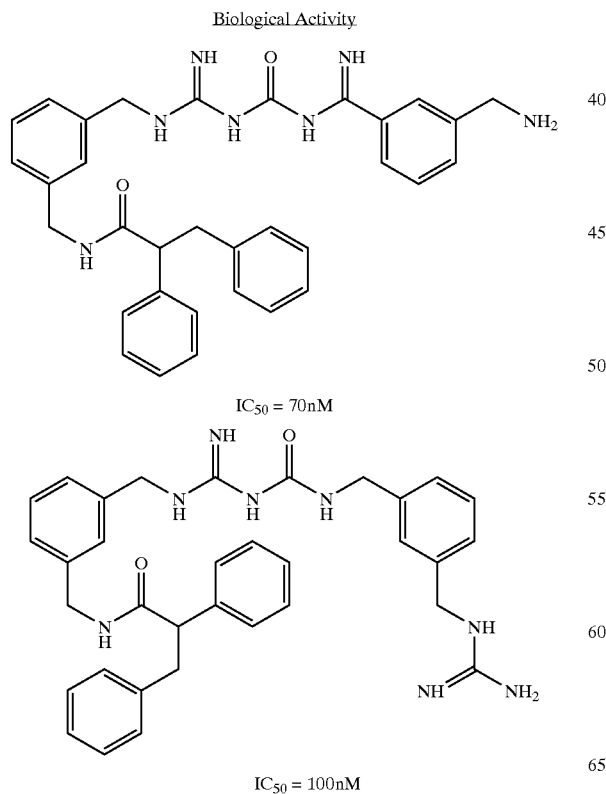

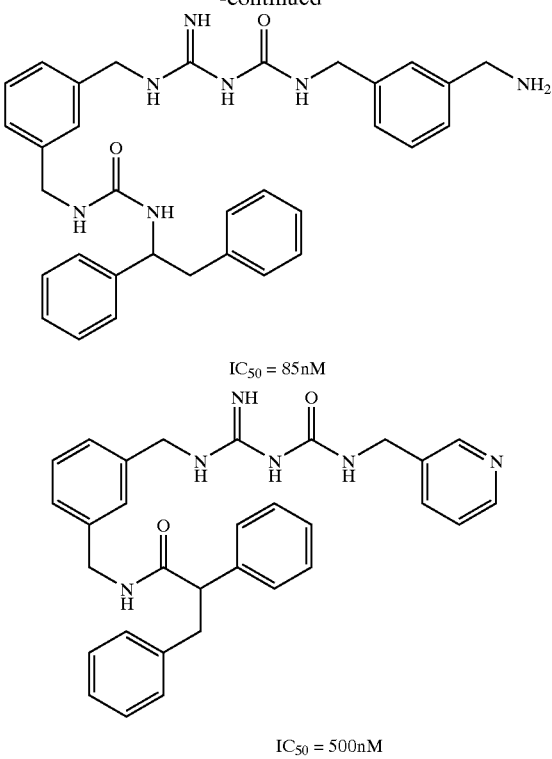

What is claimed is:
1. A compound of the formula

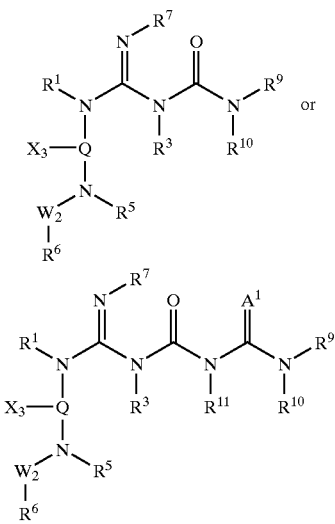

wherein:
  W2 is not present or is selected from the group consisting of C=O, SO2, SO, and C(O)NH;
  A1 is selected from the group consisting of O, S, NH, N-lower alkyl, and N-aryl;
  R1 and R3 are each independently selected from the group consisting of: H; and cyclic or acyclic straight- or branched-chain, saturated or unsaturated C1–C14 alkyl groups, which are unsubstituted or substituted with one or more substituents selected from the group consisting of hydroxy, lower alkoxy, alkylthio, aryloxy, and arylthio groups, where the aryl-bearing groups are each unsubstituted or substituted with one or more substituents selected from the group consisting of halogen, lower alkyloxy, alkylthio, lower alkyl, trifluorometoxy, trifluoroethoxy, and trifluoromethyl groups, and the alkyl-bearing groups are unsubstituted or substituted with one or more substituents selected from the group consisting of cyclic structures having a ring size of from 3 to 10 atoms and aryl and heteroaryl groups unsubstituted or substituted with one or more substituents selected from the group consisting of lower alkyl, alkoxy, amino, lower alkylamino, lower acytamino, halogen, trifluoromethyl and trifluoromethoxy groups;

R5, R7, R9, and R11 (where present) are each independently selected from the group consisting of: H; cyclic or acyclic straight- or branched-chain, saturated or unsaturated C1–C14 alkyl groups, which are unsubstituted or substituted with one or more substituents selected from the group consisting of non-aromatic cyclic structures having from 3 to 14 ring atoms, aromatic and heteroaromatic structures, and heterocyclic rings having from 4 to 12 ring atoms, the aromatic and heteroaromatic structures being unsubstituted or substituted with one or more substituents selected from the group consisting of lower alkyl, alkoxy, amino, lower alkylamino, lower acylamido, halogen, perfluoroalkyl, perfluoro-lower alkoxy, and aryl and heteroaryl groups, the aryl and heteroaryl groups being unsubstituted or substituted with one or more substituents selected from the group consisting of halogen, lower alkoxy, alkylthio, lower alkyl, trifluoromethoxy and trifluoromethyl groups; and aryl and heteroaryl groups unsubstituted or substituted with one more substituents selected from the group consisting of halogen, lower alkoxy, alkylthio, lower alkyl, trifluoromethoxy, and trifluoromethyl groups;

R6 is selected from the group consisting of H, R6', R6'—NH, and R6'—N-lower alkyl, where R6' is selected from the group consisting of: cyclic or acyclic straight- or branched-chain, saturated or unsaturated C1–C14 alkyl; aryl; heteroaryl; aryl-lower alkyl; heteroaryl-lower alkyl; condensed aryl-lower alkyl; condensed heteroaryl-lower alkyl; bis-aryl-lower alkyl; bis-heteroaryl-lower alkyl; heteroaryl-lower alkyl-aryl; and partially or fully saturated derivatives thereof;

R10 is selected from the group consisting of: H; and cyclic or acyclic straight- or branched-chain, saturated or unsaturated C1–C12 alkyl groups; aryl groups unsubstituted or substituted with one or more substituents selected from the group consisting of halogen, lower alkyl, alkoxy, aminoalkyl, di(lower alkyl)-amino-lower alkyl, and hydroxy; arylalkyl; aryloxyalkyl; 2-tetrahydrofuryl; 3-tetrahydrofuryl; terminal hydroxyalkyl; and amidoalkyl;

or R9 and R10 together with the nitrogen to which they are bonded form a 3- to 10-membered ring;

Q is selected from: —(CH2—)z, where z is an integer of from 1 to 12, unsubstituted or substituted with one or more substituents selected from the group consisting of lower alkyl, aryl, and heteroaryl, and where when z is >1, one or more —CH2- each is optionally replaced by an atom selected from O, S, and N, with N being optionally substituted with lower alkyl, aryl, or heteroarylalkyl; —(CH2)m— (CH2)x — CH2)l —, where l and m are each independently an integer of from 0 to 5 and x is an integer from 3 to 12, where —(CH2)x— is a 3- to 12-membered saturated carbocyclic or heterocyclic ring unsubstituted or substituted with one or more substituents selected from the group consisting of lower alkyl, cycloalkyl, aryl, and heteroaryl, where when the ring is heterocyclic, one or more of the ring —CH2- units is replaced by a heteroatom selected from O, S, Se, and N, with N being unsubstituted or substituted with lower alkyl, aryl, or heteroaryl; and —(CH2)m— (—CH=CH—)y —(CH2)l—, where l and m are each independently an integer of from 0 to 5 and y is 2 or 3, and where—(—CH=CH—)y—is a 4- to 6-membered aromatic carbocyclic or heterocyclic ring unsubstituted or substituted with one or more substituents selected form the group consisting of saturated or unsaturated, straight- or branched-chain alkyl groups, lower alkoxy groups, and halogens, where when the ring is heterocyclic, one or more of the ring —CH— or —CH=CH— units is replaced by a heteroatom selected from O, S, Se, and N, with N being optionally substituted with lower alkyl, aryl, or heteraryl; and X3 is selected from the group consisting of H, lower alkyl, aryl, lower alkoxy, hydroxy, and trifluoromethyl;

or a pharmaceutically acceptable salt thereof.

2. A composition comprising a compound or a pharmaceutically acceptable salt according to claim 1 and a pharmaceutically acceptable carrier.

3. A compound according to claim 1 of formula:

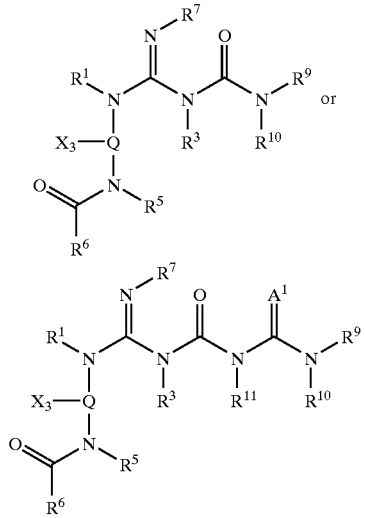

wherein the variables are as previously defined, or a pharmaceutically acceptable salt thereof.

4. A compound or a pharmaceutically acceptable salt thereof according to claim 3, wherein Q is selected from the group consisting of:

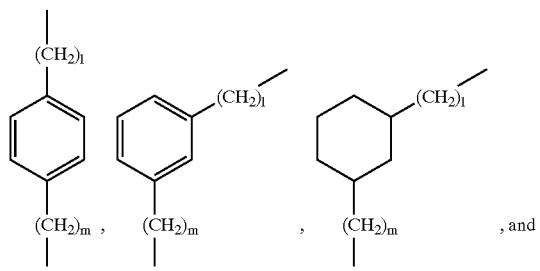

73

-continued

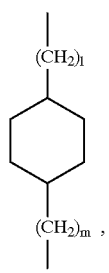

wherein l and m are each independently 0 or 1.

5. A compound or a pharmaceutically acceptable salt thereof according to claim 1, wherein Q is selected from the group consisting of:

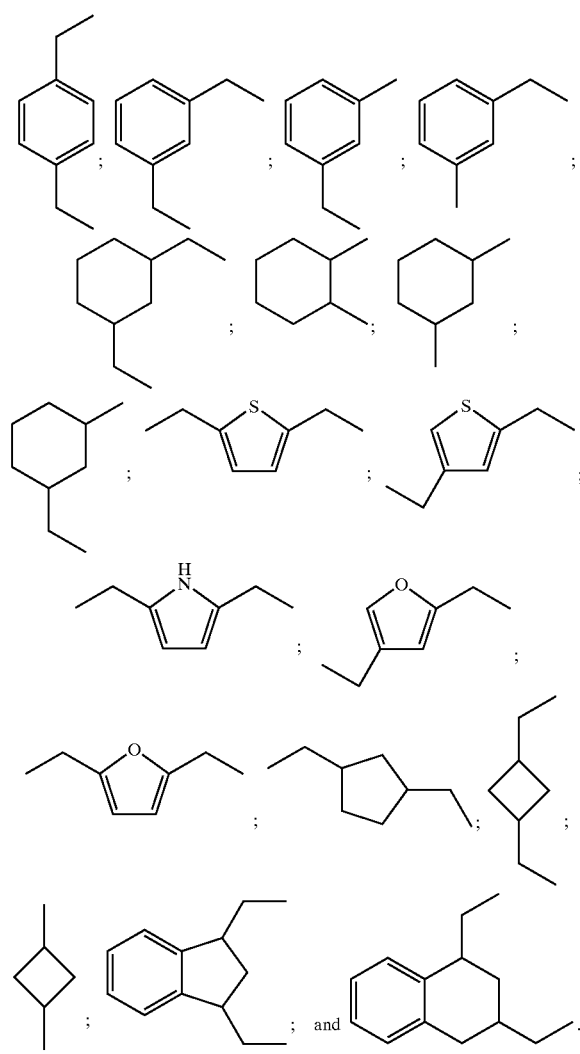

6. A compound or a pharmaceutically acceptable salt thereof according to claim 1, wherein the compound is of the formula:

74

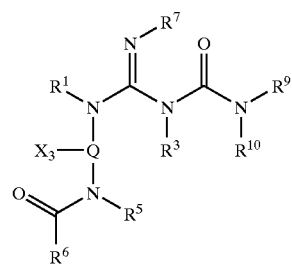

wherein the variables are as previously defined.

7. A compound or a pharmaceutically acceptable salt thereof according to claim 1, wherein R6 is select from the group consisting of aryl, heteroaryl, aryl-lower alkyl, heteroaryl-lower alkyl, condensed aryl-lower alkyl, condensed heteroaryl-lower alkyl, bis-aryl-lower alkyl, bis-heteroaryl-lower alkyl, heteroaryl-lower alkyl-aryl, and partially or fully saturated derivatives thereof.

8. A compound or a pharmaceutically acceptable salt thereof according to claim 1, wherein R6 is selected from the group consisting of:

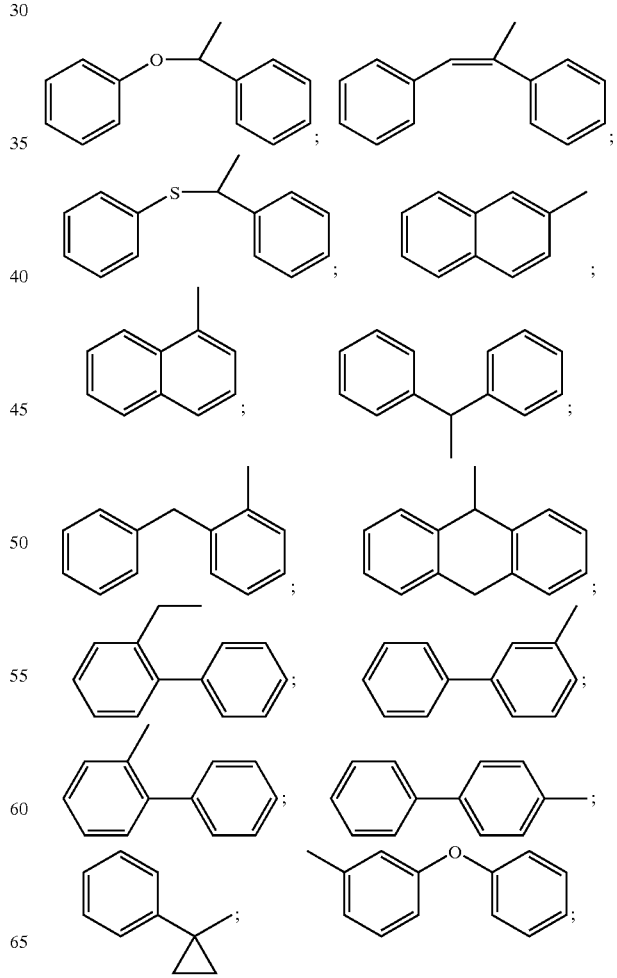

75
-continued

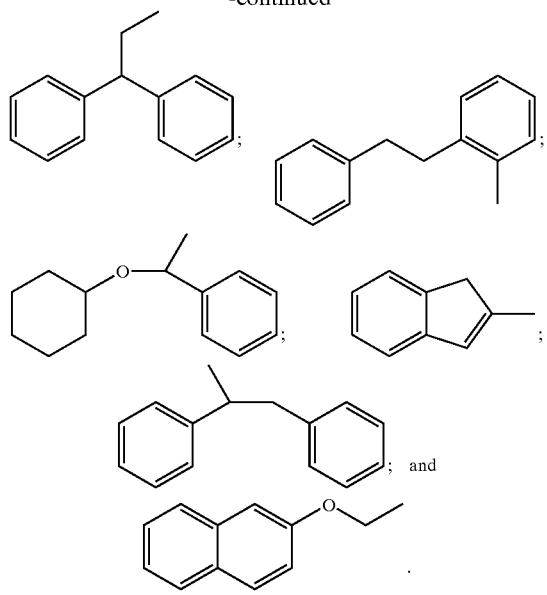

9. A compound or a pharmaceutically acceptable salt thereof according to claim 1, wherein R10 is selected from the group consisting of: cyclic or acyclic straight- or branched-chain, saturated or unsaturated C1–C12 alkyl; aryl unsubstituted or substituted with one or more substituents selected from the group consisting of halogen, lower alkyl, alkoxy, aminoalkyl, di-(lower alkyl amino-lower alkyl, and hydroxy groups; arylalkyl; aryloxyalkyl; 2-tetrahydrofuryl; 3-tetrahydrofuryl; terminal hydroxyalkyl; and amidoalkyl.

10. A compound or a pharmaceutically acceptable salt thereof according to claim 1, wherein R10 is selected from the group consisting of:

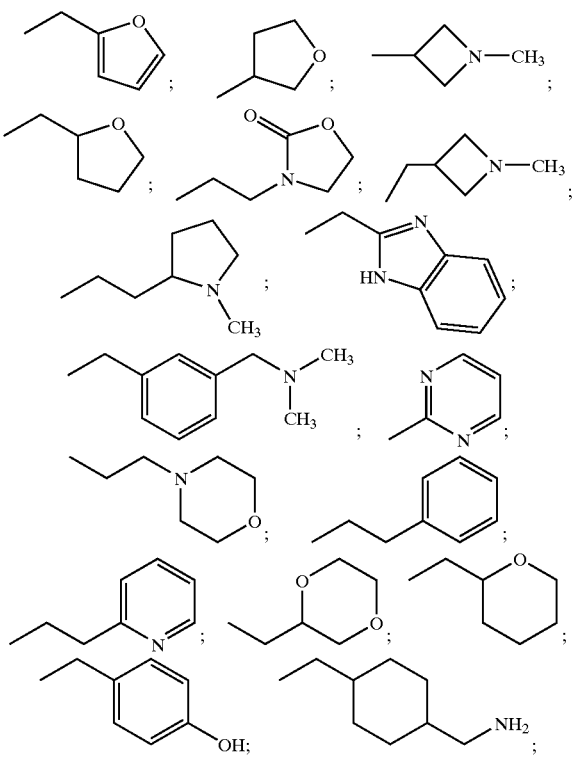

76
-continued

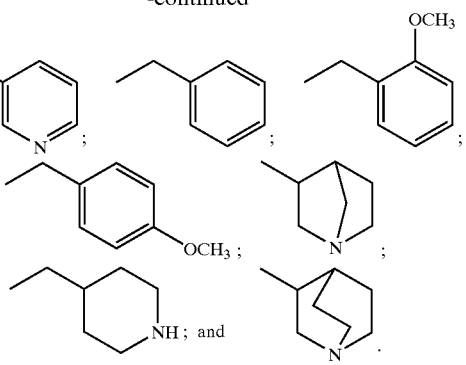

11. A compound according to claim 1 of the formula:

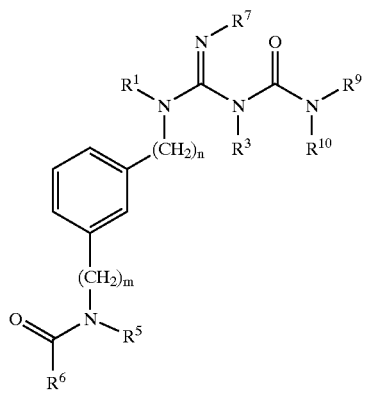

wherein the variables are as previously defined, or a pharmaceutically acceptable salt thereof.

12. A compound or pharmaceutically acceptable salt according to claim 11, wherein R1, R3, R5, R7, and R10 are each H.

13. A compound or a pharmaceutically acceptable salt thereof according to claim 3, wherein R1, R3, R5, R7, and R9 are each H; R11 (where present) is H or methyl; and A1 is NH.

14. A compound according to claim 1 having the formula:

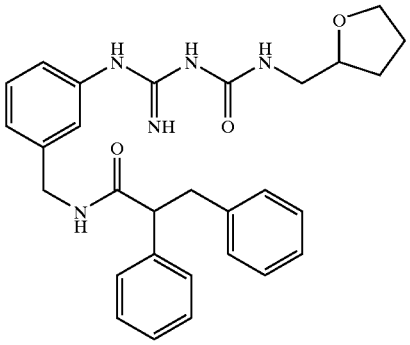

or a pharmaceutically acceptable salt thereof.

* * * * *